(12) United States Patent
Smallheer et al.

(10) Patent No.: US 11,180,490 B2
(45) Date of Patent: Nov. 23, 2021

(54) CYCLOPROPYL UREA FORMYL PEPTIDE 2 RECEPTOR AND FORMYL PEPTIDE 1 RECEPTOR AGONISTS

(71) Applicant: BRISTOL-MYERS SQUIBB COMPANY, Princeton, NJ (US)

(72) Inventors: Joanne M. Smallheer, Yardley, PA (US); Nicholas R. Wurtz, Pennington, NJ (US); Meriah Neissel Valente, Bedminister, NJ (US); Karen A. Rossi, Newtown, PA (US); Ellen K. Kick, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 50 days.

(21) Appl. No.: 16/619,961

(22) PCT Filed: Jun. 8, 2018

(86) PCT No.: PCT/US2018/036635
§ 371 (c)(1),
(2) Date: Dec. 6, 2019

(87) PCT Pub. No.: WO2018/227067
PCT Pub. Date: Dec. 13, 2018

(65) Prior Publication Data
US 2020/0199113 A1   Jun. 25, 2020

Related U.S. Application Data

(60) Provisional application No. 62/517,259, filed on Jun. 9, 2017.

(51) Int. Cl.
*C07D 207/273* (2006.01)
*C07D 401/12* (2006.01)
*C07D 401/14* (2006.01)
*C07D 403/12* (2006.01)
*C07D 407/12* (2006.01)
*C07D 413/12* (2006.01)
*C07D 413/14* (2006.01)
*C07D 417/12* (2006.01)
*C07D 471/04* (2006.01)
*C07D 405/12* (2006.01)
*C07D 405/14* (2006.01)
*C07D 409/12* (2006.01)

(52) U.S. Cl.
CPC ....... *C07D 413/14* (2013.01); *C07D 207/273* (2013.01); *C07D 401/12* (2013.01); *C07D 403/12* (2013.01); *C07D 405/12* (2013.01); *C07D 405/14* (2013.01); *C07D 409/12* (2013.01); *C07D 417/12* (2013.01); *C07D 471/04* (2013.01)

(58) Field of Classification Search
CPC ............. C07D 207/273; C07D 401/12; C07D 401/14; C07D 403/12; C07D 407/12; C07D 417/12; C07D 471/04
See application file for complete search history.

(56) References Cited

U.S. PATENT DOCUMENTS

| | | | |
|---|---|---|---|
| 9,822,069 B2 | 11/2017 | Takahashi et al. | |
| 10,029,983 B2 | 7/2018 | Takahashi et al. | |
| 10,252,992 B2 | 4/2019 | Takahashi et al. | |
| 10,464,891 B2 | 11/2019 | Takahashi et al. | |

FOREIGN PATENT DOCUMENTS

| | | |
|---|---|---|
| EP | 3075726 B1 | 11/2017 |
| WO | WO2014111465 A1 | 7/2014 |
| WO | WO2015079692 A1 | 6/2015 |
| WO | WO2016189876 A1 | 12/2016 |
| WO | WO2016189877 A1 | 12/2016 |
| WO | WO2017091496 A1 | 6/2017 |
| WO | WO2017100390 A1 | 6/2017 |
| WO | WO2018227058 A9 | 12/2018 |
| WO | WO2018227061 A1 | 12/2018 |
| WO | WO2018227065 A1 | 12/2018 |
| WO | WO2019173182 A1 | 9/2019 |

OTHER PUBLICATIONS

Garcia et al. JACC : B asic to Tr anslationa l S c i e n c e vol. 4 , No. 8, 2 01 9, p. 905-920 (Year: 2019).*
Allen, Jr., Loyd V., "Remington: The Science and Practice of Pharmacy, vol. I and vol. II. Twenty-second edition", Pharmaceutical Press, 2012, p. 2724, pp. 220-221 provided.
Bertus et al., "A Direct Synthesis of 1-Aryl- and 1 Alkenylcyclopropylamines from Aryl and Alkenyl Nitriles", J. Org. Chem. 2003, 68, 7133-7136.

(Continued)

*Primary Examiner* — Emily A Bernhardt
(74) *Attorney, Agent, or Firm* — Hong Liu

(57) ABSTRACT

The disclosure relates to compounds of formula (I), which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, and related diseases.

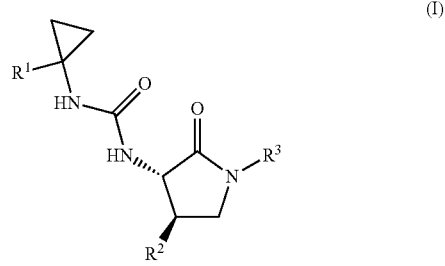

12 Claims, No Drawings

(56) References Cited

OTHER PUBLICATIONS

Chandrasekharan et al., "Lipoxins: nature's way to resolve inflammation", Journal of Inflammation Research, 2015:8 181-192.
Fredman et al., "Targeted nanoparticles containing the proresolvingpeptide Ac2-26 protect against advancedatherosclerosis in hypercholesterolernic mice", Sci. Trans. Med., 2015, 7(275); pp. 275ra20).
Gavins, Felicity N.E., "Are formyl peptide receptors novel targets for therapeutic intervention ischaemia-reperfusion injury?" Trends in Pharmacological Sciences, vol. 31(6), pp. 266-276 (2010).
Kain et al., "Resolvin D1 activates the inflammation resolving response at splenic and ventricular site following myocardial infarction leading to improved ventricular function", Journal of Molecular and Cellular Cardiology, vol. 84, pp. 24-35 (2015).
Liu et al., "Lipoxin A4 ameliorates ischemia/reperfusion induced spinal cord injury in rabbit model", Int. J. Clin.Exp. Medicine, Vo. 8(8), pp. 12826-12833 (2015.
Perretti, et al., "Resolution Pharmacology:Opportunities for Therapeutic Innovationin Inflammation", Trends in Pharmacological Sciences,vol. 36(11) 2015.
Petri et al., "The role of the FPR2/ALX receptor in atherosclerosis development and plaque stability", Cardiovascular Research, vol. 105, pp. 65-74 (2015).
Romano et al., "Lipoxins and aspirin-triggered lipoxinsin resolution of inflammation", European Journal of Pharmacology vol. 760 pp. 49-63 (2015).
Ye et al., "International Union of Basic and Clinical Pharmacology. LXXIII. Nomenclature for the Formyl Peptide Receptor (FPR) Family", Pharmacological Reviews, vol. 61(2), 2009.

\* cited by examiner

CYCLOPROPYL UREA FORMYL PEPTIDE 2 RECEPTOR AND FORMYL PEPTIDE 1 RECEPTOR AGONISTS

CROSS-REFERENCE TO RELATED APPLICATION

This application is a 371 application of PCT/US2018/036635 filed Jun. 8, 2018, which claims the benefit of U.S. Provisional Application Ser. No. 62/517,259 filed on Jun. 9, 2017, which is hereby incorporated by reference in its entirety.

BACKGROUND OF THE INVENTION

The present invention relates to novel compounds which are formyl peptide 2 (FPR2) receptor agonists and/or formyl peptide 1 (FPR1) receptor agonists, compositions containing them, and methods of using them, for example, for the treatment of atherosclerosis, heart failure, chronic obstructive pulmonary disease (COPD), and related diseases.

Formyl peptide receptor 2 (FPR2) belongs to small group of seven-transmembrane domain, G protein-coupled receptors that are expressed mainly by mammalian phagocytic leukocytes and are known to be important in host defense and inflammation. FPR2 shares significant sequence homology with FPR1 and FPR3. Collectively, these receptors bind large number of structurally diverse group of agonists, including N-formyl and nonformyl peptides which act as chemo attractants and activate phagocytes. The endogenous anti-inflammatory peptide Annexin A1 and its N-terminal fragments also bind human FPR1 and FPR2. Importantly, anti-inflammatory eicosanoid lipoxin A4, which belongs to newly discovered class of small pro-resolution mediators (SPMs), has been identified as a specific agonist for FPR2 (Ye R D., et al., Pharmacol. Rev., 2009, 61, 119-61).

Endogenous FPR2 pro-resolution ligands, such as lipoxin $A_4$ and Annexin A1 bind to the receptor triggering a wide array of cytoplasmatic cascades such as Gi coupling, $Ca^{2+}$ mobilization and β-arrestin recruitment. Activation of FPR2 by lipoxin A4 modifies the effects of peptidic agonists, such as serum amyloid A (SAA), and has alternative effects on phosphorylation pathways depending on the cell type. Lipoxins regulate components of both innate and adaptive immune systems including neutrophils, macrophages, T-, and B-cells. In neutrophils, lipoxins modulate their movement, cytotoxicity and life span. In macrophages, lipoxins prevent their apoptosis and enhance efferocytosis. In most inflammatory cells, lipoxins also down-regulate expression of several pro-inflammatory cytokines, such as IL-6, IL-1β and IL-8 as well as up-regulate expression of anti-inflammatory cytokine IL-10 (Chandrasekharan J A, Sharma-Walia N., J. Inflamm. Res., 2015, 8, 181-92). The primary effects of lipoxin on neutrophils and macrophages are termination of inflammation and initiation of resolution of inflammation. The latter is primarily responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischaemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive lost of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q, et al., Int. J. Clin. Exp. Med., 2015, 8, 12826-33).

In addition to beneficial effects of targeting the FPR2 with novel pro-resolution agonists for treatment of I/R induced injury therapeutic, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, occular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

DESCRIPTION OF THE INVENTION

The invention encompasses compounds of formula I, which are formyl peptide 2 (FPR2) receptor agonists and/or formyl peptide 1 (FPR1) receptor agonists, compositions containing them, and methods of using them, for example, in the treatment of atherosclerosis, heart failure, chronic obstructive pulmonary disease (COPD), and related diseases.

One aspect of the invention is a compound of formula I

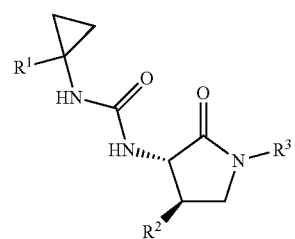

where
$R^1$ is phenyl, biphenyl, dihydrobenzofuranyl, benzodioxolyl, chromenyl, naphthalenyl, pyrrolyl, furanyl, thienyl, pyrazolyl, isoxazolyl, isothiazolyl, imidazolyl, oxazolyl, thiazolyl, (phenyl)thiazolyl, triazolyl, oxadiazolyl, thiadiazolyl, pyridinyl, pyridazinyl, pyrimidinyl, pyrazinyl, indolyl, azaindolyl, benzofuranyl, benzothiophenyl, indazolyl, benzimidazolyl, benzoxazolyl, benzothiazolyl, pyrrolopyridinyl, furopyridinyl, thienopyridinyl, oxazolopyridinyl, thiazolopyridinyl, quinolinyl, isoquinolinyl, or naphthyridinyl, and is substituted with 0-3 substituents selected from cyano, halo, alkyl, benzyl, haloalkyl, alkoxy, haloalkoxy, phenylcyclohexyloxy, (trifluoroalkoxy)alkoxy, tetrahydronaphthylalkoxy, bicyclo[4.2.0]octa-1,3,5-trien-7-ylalkoxy, naphthylalkoxy, phenylalkoxy, biphenylalkoxy, (2,3-dihydro-1H-inden-2-yl)methoxy, (cycloalkyl)alkoxy, ((phenyl)alkoxy)alkoxy, and phenoxy;

$R^2$ is phenyl, pyridinyl, or dihydrobenzofuranyl, and is substituted with 0-3 substituents selected from cyano, halo, alkyl, haloalkyl, cycloalkyl, alkoxy, deuteroalkoxy, and haloalkoxy; and $R^3$ is hydrogen, alkyl, hydroxyalkyl, alkoxyalkyl, haloalkyl, (cycloalkyl)alkyl, cyanoalkyl, arylalkyl or heteroarylalkyl; or a pharmaceutically acceptable salt thereof.

Another aspect of the invention is a compound of formula I where:

$R^1$ is phenyl, benzodioxolyl, chromenyl, naphthalenyl, oxazolyl, thiazolyl, (phenyl)thiazolyl, pyridinyl, pyridazinyl, pyrimidinyl, pyrazinyl, benzothiophenyl, benzoxazolyl, benzothiazolyl, indazolyl, pyrrolopyridinyl, quinolinyl, isoquinolinyl, or naphthyridinyl, and is substituted with 0-3 substituents selected from cyano, halo, alkyl, haloalkyl, alkoxy, and haloalkoxy;

$R^2$ is phenyl, pyridinyl, or dihydrobenzofuranyl and is substituted with 1-3 substituents selected from halo and alkoxy; and $R^3$ is hydrogen, alkyl, hydroxyalkyl, haloalkyl, cycloalkylalkyl, cyanoalkyl, arylalkyl or heteroarylalkyl; or a pharmaceutically acceptable salt thereof.

Another aspect of the invention is a compound of formula I where $R^1$ is phenyl, dihydrobenzofuranyl, benzodioxolyl, chromenyl, naphthalenyl, oxazolyl, thiazolyl, (phenyl)thiazolyl, pyridinyl, pyridazinyl, pyrimidinyl, pyrazinyl, benzothiophenyl, azindolyl, indazolyl, benzoxazolyl, benzothiazolyl, pyrrolopyridinyl, quinolinyl, isoquinolinyl, or naphthyridinyl, and is substituted with 0-3 substituents selected from cyano, halo, alkyl, haloalkyl, alkoxy, and haloalkoxy;

$R^2$ is phenyl or dihydrobenzofuranyl, and is substituted with 1-3 substituents selected from cyano, halo, alkyl, haloalkyl, alkoxy, and haloalkoxy; and $R^3$ is hydrogen, alkyl, hydroxyalkyl, haloalkyl, cycloalkylalkyl, cyanoalkyl, arylalkyl or heteroarylalkyl; or a pharmaceutically acceptable salt thereof.

Another aspect of the invention is a compound of formula I where $R^1$ is phenyl, pyrrolyl, furanyl, thienyl, pyrazolyl, isoxazolyl, isothiazolyl, imidazolyl, oxazolyl, thiazolyl, (phenyl)thiazolyl, triazolyl, oxadiazolyl, thiadiazolyl, pyridinyl, pyridazinyl, pyrimidinyl, or pyrazinyl, and is substituted with 0-3 substituents selected from cyano, halo, alkyl, haloalkyl, alkoxy, and haloalkoxy.

Another aspect of the invention is a compound of formula I where $R^1$ is dihydrobenzofuranyl, benzodioxolyl, chromenyl, naphthalenyl, indolyl, benzofuranyl, benzothiophenyl, indazolyl, benzimidazolyl, benzoxazolyl, benzothiazolyl, pyrrolopyridinyl, furopyridinyl, thienopyridinyl, oxazolopyridinyl, thiazolopyridinyl, quinolinyl, isoquinolinyl, or naphthyridinyl, and is substituted with 0-3 substituents selected from cyano, halo, alkyl, haloalkyl, alkoxy, and haloalkoxy.

Another aspect of the invention is a compound of formula I where $R^1$ is phenyl, dihydrobenzofuranyl, benzodioxolyl, chromenyl, naphthalenyl, oxazolyl, thiazolyl, (phenyl)thiazolyl, pyridinyl, pyridazinyl, pyrimidinyl, pyrazinyl, benzothiophenyl, indazolyl, benzoxazolyl, benzothiazolyl, pyrrolopyridinyl, quinolinyl, isoquinolinyl, or naphthyridinyl, and is substituted with 0-3 substituents selected from cyano, halo, alkyl, haloalkyl, alkoxy, and haloalkoxy.

Another aspect of the invention is a compound of formula I where $R^1$ is phenyl, naphthyl, pyridinyl, pyridazinyl, pyrimidinyl, pyrazinyl, quinolinyl, isoquinolinyl, thienyl, benzothiophenyl, benzthiazolyl, benzoxazolyl, indolyl, indazolyl, azaindolyl, naphthyridinyl, 2,2-difluorobenzo[d][1,3]dioxolyl, pyrrolyl, furanyl, pyrazolyl, isoxazolyl, isothiazolyl, imidazolyl, oxazolyl, thiazolyl, triazinyl, oxadiazolyl, or thiadiazolyl, and is substituted with 0-3 substituents selected from cyano, halo, alkyl, haloalkyl, alkoxy, haloalkoxy, alkylthio, phenyl, and $SO_2R^3$.

Another aspect of the invention is a compound of formula I where $R^1$ is selected from phenyl, 4-methylphenyl, 3,5-dimethylphenyl, 3,4-dichlorophenyl, 4-chlorophenyl, 3-methoxyphenyl, 2-fluorophenyl, 3-fluorophenyl, 4-fluorophenyl, 4-cyanophenyl, 3-trifluoromethylphenyl, 3-methylphenyl, 4-methoxyphenyl, 3-chlorophenyl, 3,5-dichlorophenyl, 3-fluoro-5-trifluoromethylphenyl, 3,5-ditrifluoromethylphenyl, 3-trifluoromethoxyphenyl, 4-chloro-3-methylphenyl, 3,4-dichlorophenyl, 3-chloro-4-trifluoromethoxyphenyl, 3-chloro-4-methylphenyl, 2-naphthyl, 3-chloro-4-trifluoromethylphenyl, 6-methoxy-2-naphthyl, 3-methyl-5-trifluoromethylphenyl, 4-chloro-3-fluorophenyl, 3-methyl-5-trifluoromethoxyphenyl, 3-chloro-5-trifluoromethoxy, 2-pyridyl, 6-chloro-2-pyridyl, 5-chloro-2-pyridyl, 6-methyl-2-pyridyl, 6-methyl-2-pyridyl, 4-methyl-2-pyridyl, 5-trifluoromethyl-2-pyridyl, 6-fluoro-2-pyridyl, 4,6-dimethyl-2-pyridinyl, 6-methyl-2-pyrdiyl, 5-methyl-2-pyridyl, 6-chloro-4-methyl-2-pyridyl, 5-chloro-6-methyl-2-pyridyl, 6-chloro-2-pyridyl, 2-chloro-4-pyridinyl, 1,5-naphthyridin-2-yl, benzoxazol-2-yl, 5-methyl-2-oxazolyl, 4-methoxy-2-benzthiazolyl, 2-quinolinyl, 4,6-dimethyl-2-pyrimidinyl, 3-isoquinolinyl, 3-pyridazinyl, 6-methoxy-2-benzthiazolyl, 1,7-naphthyridin-2-yl, 6-methyl-2-pyrazinyl, 1-methyl-1H-pyrrolo[3,2-b]pyridin-5-yl, 5-benzothiophenyl, 2,2-difluoro-2H-1,3-benzodioxol-5-yl, 2-benzoxazolyl, 6-chloro-2-quinolinyl, 2-chloro-4-pyridinyl, 6-chloro-2-benzoxazolyl, 2-benzthiazolyl, 1-methyl-1H-pyrrolo[2,3-b]pyridin-3-yl, 1-methyl-1H-indazol-6-yl, 5-chloro-2-benzoxazolyl, 5-phenyl-2-thiazolyl, 6-benzthiazolyl, 2-methyl-4-thiazolyl, 4-methyl-2-thiazolyl, 1-(2,2-dimethyl-2H-chromen-6-yl), 5-trifluoromethoxy-2-benzoxazolyl, 6-trifluoromethyl-2-benzoxazolyl, 5-methyl-2-benzoxazolyl, and ethoxycarbonyl.

Another aspect of the invention is a compound of formula I where $R^2$ is phenyl, pyridinyl, pyridazinyl, pyrimidinyl, pyrazinyl, thienyl, benzofuranyl, dihydrobenzofuranyl, indolinyl, indanyl, indanonyl, chromanyl and is substituted with 1-3 substituents selected from cyano, halo, alkyl, deuteroalkoxy, haloalkyl, alkoxy, and haloalkoxy.

Another aspect of the invention is a compound of formula I where $R^2$ is phenyl or dihydrobenzofuranyl, and is substituted with 1-3 substituents selected from cyano, halo, alkyl, haloalkyl, alkoxy, and haloalkoxy.

Another aspect of the invention is a compound of formula I where $R^2$ is selected from 2,6-difluoro-4-methoxyphenyl, 3-fluoro-5-methoxy-2-pyridinyl, 6-fluoro-2,3-dihydrobenzofuran-5-yl, 2,6-difluoro-4-(methoxy-d3)phenyl, 2,6-difluoro-4-difluoromethoxyphenyl, 4-bromo-2,6-difluorophenyl, and 2,4,6-trifluorophenyl.

Another aspect of the invention is a compound of formula I where $R^3$ is hydrogen, alkyl, hydroxyalkyl, haloalkyl, cycloalkylalkyl, cyanoalkyl, arylalkyl or heteroarylalkyl;

Another aspect of the invention is a compound of formula I where $R^3$ is hydrogen, alkyl, hydroxyalkyl, or alkoxyalkyl;

Another aspect of the invention is a compound of formula I where $R^3$ is hydrogen, alkyl, or hydroxyalkyl;

Another aspect of the invention is a compound of formula I where $R^3$ is hydrogen, methyl, propyl, cyclopropylmethyl, 3,3,3-trifluoropropyl, 2-hydroxyethyl, isobutyl, 1,1-dimethyl-2-hydroxyethyl, 2-hydroxy-2-methylpropyl, or 5-methyl-1,3,4-oxadiazol-2-yl.

For a compound of Formula I, the scope of any instance of a variable substituent, including $R^1$, $R^2$, and $R^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon group having 6 to 12 carbon atoms. Bicyclic ring systems can consist of a phenyl group fused to a aromatic or non-aromatic carbocyclic ring. Representative examples of aryl groups include but are not limited to phenyl, indanyl, indenyl, naphthyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

Heteroaryl includes N-substituted pyridinonyl:

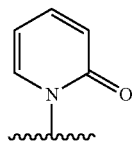 [SMILES: *n1ccccc1=O]

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, Ca2+ mobilization and transcription. The family interacts with a diverse set of ligands that includes proteins, polypeptides and fatty acid metabolites which activate both pro-inflammatory and pro-resolution downstream responses.

The FPR2 receptor binds multiple ligands to invoke both inflammatory and anti-inflammatory responses. Inflammation mediator release by FPR2 is promoted by endogenous protein ligands such as Serum amyloid A (SAA) and Amyloid β (1-42), whereas resolution of inflammation is induced by ligands that include arachidonic acid metabolites, lipoxin A4 (LXA4) and Epi-lipoxin (ATL), and a docosahexaenoic acid metabolite, resolvin D1 (RvD1). The pro-resolving fatty acid metabolites mediate inhibition and resolution of inflammation through the FPR2 receptor by stimulating phagocytosis of apototic neutrophils by macrophages. Removal of the apototic neutrophils induce the release of cytokines that activate pro-resolution pathways.

The FPR1 receptor was originally isolated as a high affinity receptor for N-Formylmethionine containing peptides, such as N-Formylmethionine-leucyl-phenylalanine (FMLP). The protein directs mammalian phagocytic and blood leukocyte cells to sites of invading pathogens or inflamed tissues and activates these cells to kill pathogens or to remove cellular debris.

FPR2 and FPR1 Cyclic Adenosine Monophosphate (cAMP) Assays. A mixture of forskolin (5 μM final for FPR2 or 10 μM final for FPR1) and IBMX (200 μM final) were added to 384-well Proxiplates (Perkin-Elmer) pre-dotted with test compounds in DMSO (1% final) at final concentrations in the range of 1.7 nM to 100 μM. Chinese Hamster Ovary cells (CHO) overexpressing human FPR1 or human FPR2 receptors were cultured in F-12 (Ham's) medium supplemented with 10% qualified FBS, 250 μg/ml zeocin and 300 μg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 µM to 0.1 pM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The exemplified Examples disclosed below were tested in the FPR2 and FPR1 cAMP assay described above and found having FPR2 and/or FPR1 agonist activity. A range of $IC_{50}$ values of ≤1 µM (1000 nM) in one of the assays was observed. Table 1 below lists $EC_{50}$ values in the FPR2 and FPR1 cAMP assays measured for the following examples.

TABLE 1

| Compound | hFPR1 cAMP EC50 (µM) | hFPR2 cAMP2 EC50 (µM) |
|---|---|---|
| 1 | 0.82 | 0.0083 |
| 2 | 0.66 | 0.033 |
| 4 | 1.0 | 0.11 |
| 8 | 0.066 | 0.0057 |
| 19 | 2.3 | 0.049 |
| 26 | 0.32 | 0.0064 |
| 47 | 0.27 | 0.0023 |
| 48 | 0.14 | 0.0097 |
| 50 | 0.20 | 0.0017 |
| 53 | 0.43 | 0.012 |
| 63 | 1.5 | 0.034 |
| 67 | 0.70 | 0.063 |
| 85 | 1.6 | 0.012 |
| 94 | 0.026 | 0.0015 |
| 95 | 0.019 | 0.0017 |
| 96 | 0.12 | 0.0020 |
| 110 | 0.15 | 0.014 |
| 115 | 0.28 | 0.025 |
| 131 | 1.0 | 0.004 |

The following Examples were tested in the hFPR2 Assay described above and found having FPR2 agonist activity with $EC_{50}$ values of <0.01 µM (10 nM): 1, 17, 21, 22, 30, 32, 35, 36, 37, 38, 43, 44, 47, 48, 54, 61, 86, 94-108, and 128-132.

The following Examples were tested in the hFPR2 Assay described above and found having FPR2 agonist activity with $EC_{50}$ values between 0.01 µM and 0.1 µM: 2, 4, 5, 6, 10, 11, 13, 14, 16, 18, 19, 24, 25, 28, 31, 34, 39, 40, 41, 42, 45, 46, 49, 50, 51, 53, 58, 59, 62, 65, 66, 67, 68, 72, 73, 74, 76, 79, 81, 82, 84, 85, 87, 88, 89, 90, 92, 109-123 and 133-140.

The following Examples were tested in the hFPR2 Assay described above and found having FPR2 agonist activity with $EC_{50}$ values between 0.1 µM and 1 µM: 3, 7, 8, 9, 12, 15, 20, 23, 26, 27, 29, 33, 52, 55, 56, 60, 63, 64, 69, 70, 71, 75, 78, 80, 81, 91, 93, 124-127 and 141-142.

Pharmaceutical Compositions and Methods of Use

The compounds of the present invention may be administered to patients for the treatment of a variety of conditions and disorders, including atherosclerosis, heart failure, lung diseases including asthma, COPD, cystic fibrosis, neuroinflammatory diseases including multiple sclerosis, Alzheimer's disease, stroke, and chronic inflammatory diseases such as inflammatory bowel disease, rheumatoid arthritis, psoriasis, sepsis, and kidney fibrosis.

Another aspect of the invention is a pharmaceutical composition comprising a therapeutically effective amount of a compound of formula I in combination with a pharmaceutical carrier.

Another aspect of the invention is a pharmaceutical composition comprising a therapeutically effective amount of a compound of formula I in combination with at least one other therapeutic agent and a pharmaceutical carrier.

Unless otherwise specified, the following terms have the stated meanings. The term "patient" means a subject suitable for therapy as determined by practitioners in the field and encompasses all suitable mammalian species including humans that could potentially benefit from treatment with a FPR2 and/or FPR1 agonist as understood by practioners in this field. Common risk factors include, but are not limited to, age, sex, weight, family history, sleep apnea, alcohol or tobacco use, physical inactivity arrthymia or signs of insulin resistance such as acanthosis *nigricans*, hypertension, dyslipidemia, or polycystic ovary syndrome (PCOS). "Treating" or "treatment" encompass the treatment of a patient as understood by practitioners in the art and include inhibiting the disease-state, i.e., arresting it development; relieving the disease-state, i.e., causing regression of the disease state; and/or preventing the disease-state from occurring in a patient. "Therapeutically effective amount" is intended to include an amount of a compound that is effective or beneficial as understood by practitioners in this field.

"Pharmaceutical composition" means a composition comprising a compound of the invention in combination with at least one additional pharmaceutically acceptable carrier. A "pharmaceutically acceptable carrier" refers to media for the delivery of biologically active agents as understood by practitioners in the art, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents, and dispensing agents. Pharmaceutically acceptable carriers are formulated according to a number of factors known to those of ordinary skill in the art. These include, without limitation, the type and nature of the active agent being formulated; the subject to which the agent-containing composition is to be administered; the intended route of administration of the composition; and the therapeutic indication being targeted. Descriptions of suitable pharmaceutically acceptable carriers and factors involved in their selection are are known in the art in such references as Allen, L. V., Jr. et al., *Remington: The Science and Practice of Pharmacy* (2 Volumes), 22nd Edition, Pharmaceutical Press (2012).

Solid compositions are normally formulated in dosage units and compositions providing form about 1 to 1000 mg of the active ingredient per dose are preferred. Some examples of dosages are 1 mg, 10 mg, 100 mg, 250 mg, 500 mg, and 1000 mg.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

Another aspect of the invention is a method for treating heart disease comprising administering a therapeutically effective amount of a compound of formula I to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

Another aspect of the invention is a method for treating heart disease wherein the treatment is post myocardial infarction.

Another aspect of the invention is the method wherein the heart disease is associated with chronic heart failure.

Another aspect of the invention is the method wherein the treatment is to improve myocardial wound healing.

Another aspect of the invention is the method wherein the treatment is to improve diminish myocardial fibrosis.

The invention encompasses all conventional modes of administration; oral and parenteral methods are preferred. Generally, the dosing regimen will be similar to other cardiovascular agents used clinically. The dosage regimen and mode for administration for the compounds of the present invention will depend on known factors known by practitioners in the art and include age, sex, health, medical condition, and weight of the recipient; the nature and extent of the symptoms; the kind of concurrent treatment; the frequency of treatment; the route of administration, and the effect desired. Typically, the daily dose will be 0.1-100 mg/kg body weight daily. Generally, more compound is required orally and less parenterally. The specific dosing regimen, however, will be determined by a physician using sound medical judgment.

Another aspect of the invention is a method for treating heart disease comprising administering a therapeutically effective amount of a compound of formula I to a patient in conjuction with at least one other therapeutic agent.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with one or more, preferable one to three, of the following heart failure agents selected from loop diuretics, Angiotensin converting enzyme (ACE) inhibitors, Angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists and cardiotonic agents. These agents include, but are not limited to furosemide, bumetanide, torsemide, sacubitrial-valsartan, thiazide diruetics, captopril, enalapril, lisinopril, carvedilol, metopolol, bisprolol, serelaxin, spironolactone, epierenone, ivabradine, candesartan, eprosartan, irbestarain, losartan, olmesartan, telmisartan, and valsartan.

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

Chemical Methods

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| Ac | Acetic |
|---|---|
| AcOH | acetic acid |
| ACN (or MeCN) | acetonitrile |
| BINAP | 2,2'-bis(diphenylphosphino)-1,1'-binaphthyl |
| Bn | benzyl |
| Boc | tert-butyl carbonyl |
| Boc$_2$O | Di-tert-butyl dicarbonate |
| Bu | butyl |
| dba (Pd$_2$(dba)$_3$) | dibenzylideneacetone |
| DCM | dichloromethane |
| DEAD | diethyl azodicarboxylate |
| DIAD | diisopropyl azodicarboxylate |
| DIEA | diisopropylethylamine |
| DMAP | 4-dimethylaminopyridine |
| DME | Dimethoxyethane |
| DMF | dimethylformamide |

| | |
|---|---|
| DMSO | dimethyl sulfoxide |
| dppf | 1,1'-bis(diphenylphosphino)ferrocene |
| Et | ethyl |
| EtOH | ethanol |
| EtOAc | ethyl acetate |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| i-Bu | isobutyl |
| i-Pr | isopropyl |
| LAH | lithium aluminum hydride |
| Me | methyl |
| MeOH | methanol |
| NMM | N-methylmorpholine |
| NMP | N-Methylpyrrolidone |
| Ph | phenyl |
| Pr | propyl |
| t-Bu | tert-butyl |
| TBDMS-Cl | t-butyldimethylchlorosilane |
| TBDMS | t-butyldimethylsilyl |
| TBDPS | t-butyldiphenylsilyl |
| TBDPS-Cl | t-butyldiphenylchlorosilane |
| TEA | Triethylamine |
| TFA | Trifluoroacetic acid |
| THF | tetrahydrofuran |
| Ts | tosyl |

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

Compounds having the general Formula I: wherein $R^1$, and $R^2$ are defined above, can be prepared by the following one or more of the synthetic Schemes.

Cyclopropylurea compounds of this invention can be prepared by the general routes outlined in Scheme 1. Carboxylic acids of formula 1a can undergo a Curtius rearrangement in the presence of imidazole via Route A to provide imidazolecarboxamide intermediates 1b. Reaction of 1b with the appropriate cyclopropylamines 1c or the corresponding cyclopropylamine hydrochlorides in the presence of TEA in a suitable solvent such as DMF at from 25-60° C. provides urea compounds of this invention of formula (I). Alternately via route B, amines 1d can be activated with CDI by stirring at rt in DCM, and the cyclopropylamines 1c added without isolation of the activated amine to form the target cyclopropylureas. The intermediate isocyanates formed in the Curtius reaction of 1a can be also reacted in situ with cyclopropylamines to give the target ureas in one pot as illustrated by Route C.

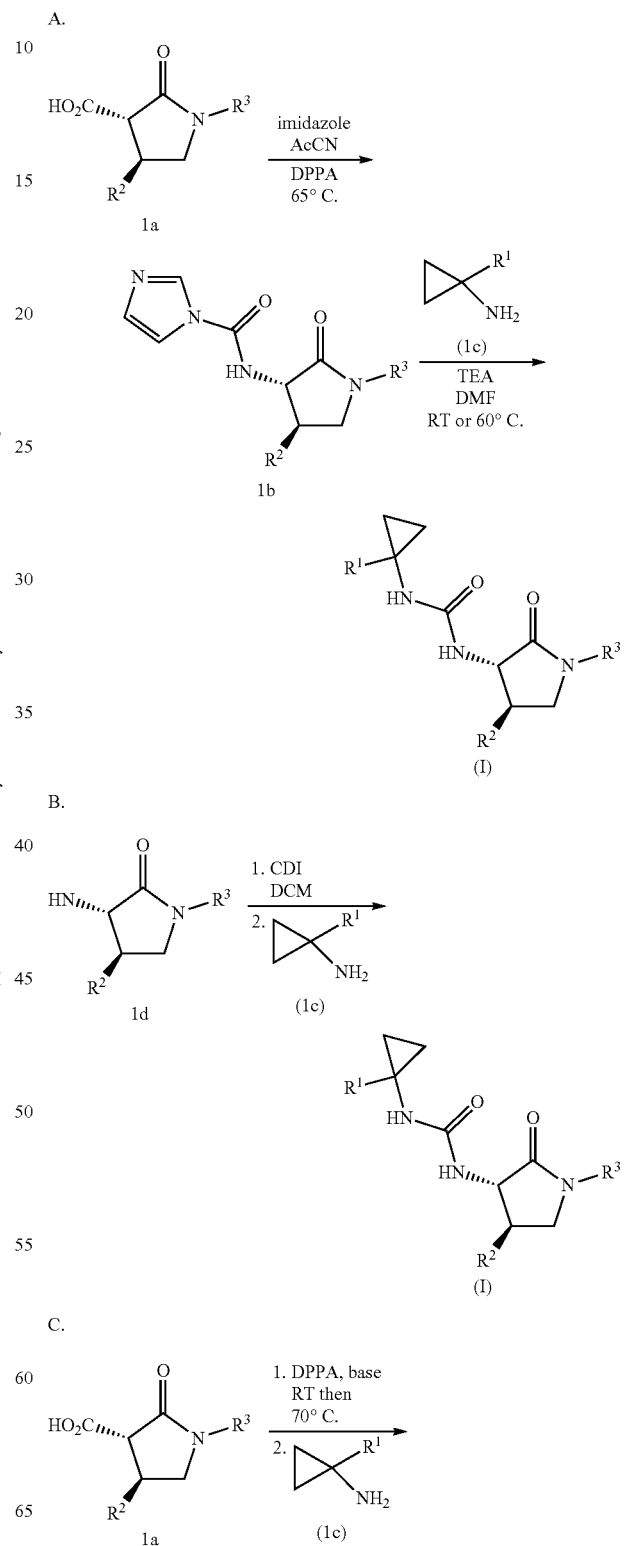

Scheme 1

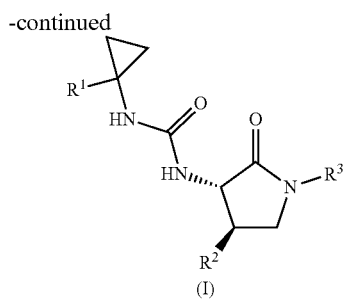

Carboxylic acid intermediates 1a can be prepared as outlined in Scheme 2 and as described in WO2015/079692 which is incorporated herein in its entirety. An aryl or heteroarylaldehyde is condensed with nitromethane to provide a nitroalkene 2b, which is then condensed with dimethylmalonate to give intermediate 2c. Reduction of the nitro group with NiCl/NaBH$_4$ provides the corresponding amine which cyclizes to the lactam 2d. Hydrolysis of the ester then provides acid intermediate 1a. Acid intermediates of formula 1a can be further converted to amine intermediates 1d via a Curtius rearrangement wherein the intermediate isocyanate is trapped in situ with benzyl alcohol. Hydrogenolysis of the resulting benzylcarbamate gives the amine intermediate, 1d.

Treatment of aryl or heteroaryl nitriles 3a with ethylmagnesium bromide in the presence of titanium isopropoxide, followed by boron trifluoride etherate according to the method of Bertus and Szymoniak (*J. Org. Chem.* 2003, 68, 7133-7136) provides the requisite cyclopropyl amines 1c as outlined in Scheme 2, Route A. Aryl and heteroaryl nitrile starting materials are either commercially available or can be obtained from the corresponding bromides by direct displacement with copper cyanide or via palladium-catalyzed cyanation using methods known to one skilled in the art. Bromides that are not commercially available can be obtained from the corresponding aryl or heterarylamines by a Sandmeyer reaction with potassium or copper bromide under standard conditions known to one skilled in the art of organic synthesis.

Alternately, the cyclopropyl amines can be obtained from the corresponding aryl or heteroaryl cyclopropyl carboxylic acids of formula 3d using a Curtius rearrangement as outlined in Scheme 3, Route B. In addition to these general methods, additional heteroaryl cyclopropylamines useful for synthesis of compounds of this invention can be prepared starting from a suitably protected 1-aminocyclopropyl-1-carboxylic acid or nitrile as illustrated in Scheme 2, Routes C-G and in the examples which follow. Suitable amine protecting groups for these transformation include Boc or Cbz.

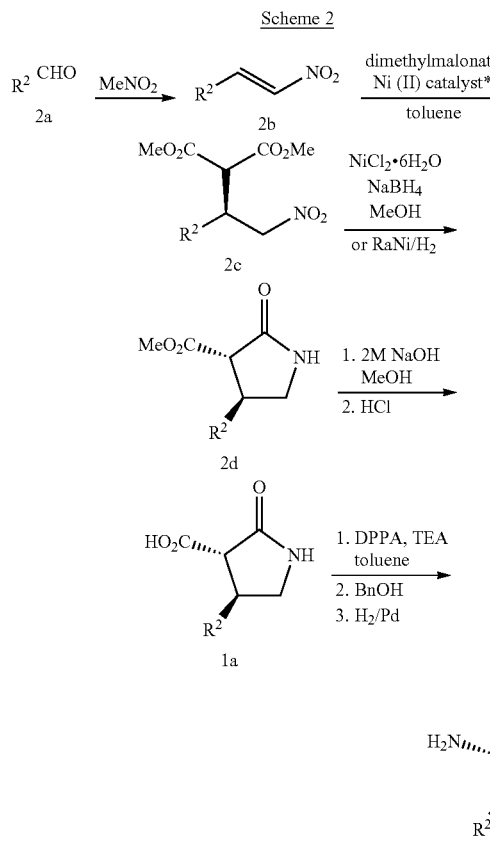

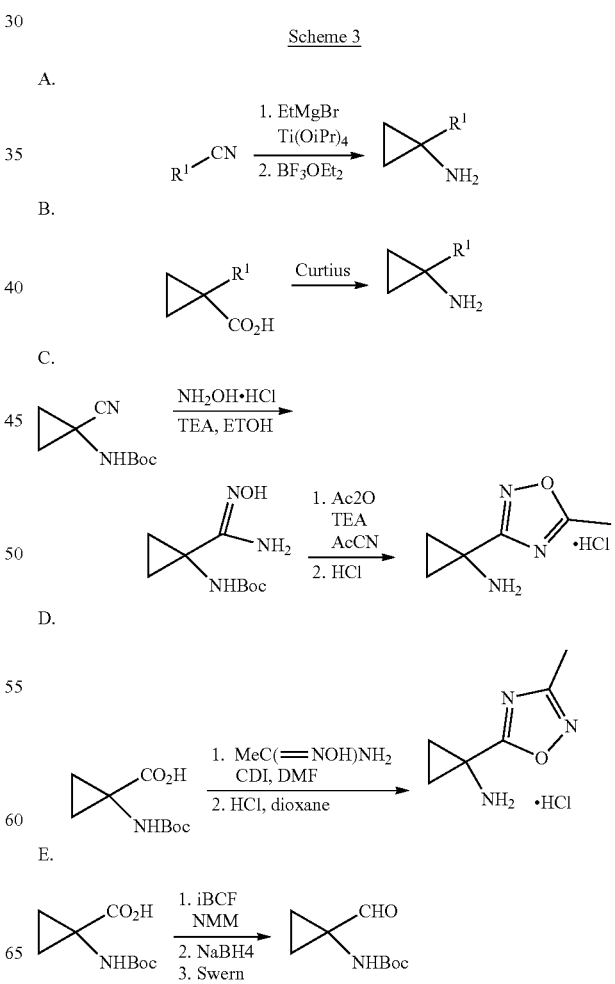

Cyclopropylamines of formula 1c are either commercially available or can be prepared by various known methods, representative examples of which are shown in Scheme 3.

-continued

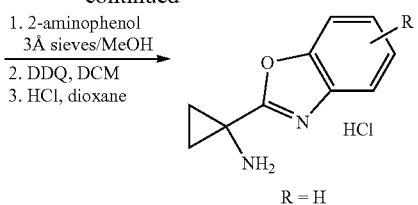

F.

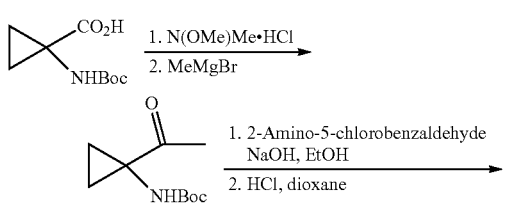

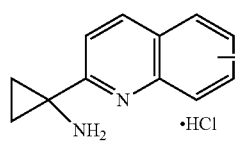

G.

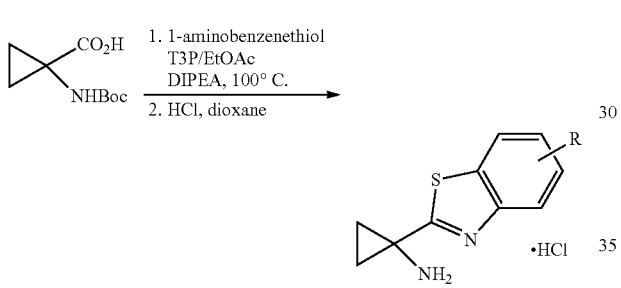

-continued

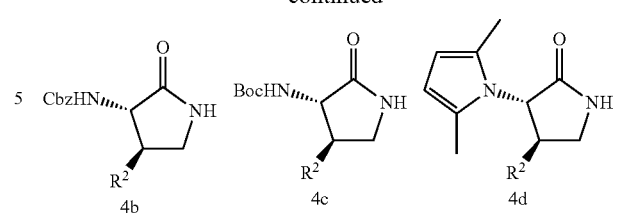

  

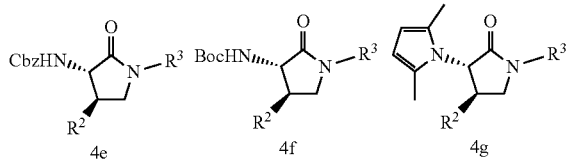

  

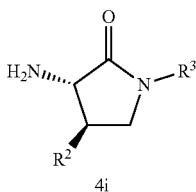

Compounds of this invention where $R^3$ is an alkyl or substituted alkyl group can be prepared as outlined in Scheme 4 wherein the amino group of a compound of formula 4a is first protected using a suitable protecting group such as Boc, Cbz or 2,5-dimethylpyrrole or phthalimide to provide compounds of formula 4b, 4c, and 4d, respectively. The lactam nitrogen is alkylated with an alkyl bromide or chloride in the presence of a base such as sodium hydride or potassium hexamethylsilazide at a temperature from 0° C. to rt to provide intermediates 4e, 4f and 4g. Removal of the protecting group then provides amine intermediate 4i which can be converted to compounds of this invention following the steps outlined in Scheme 1 for the conversion of amine 1d to compounds of formula (I).

Scheme 4

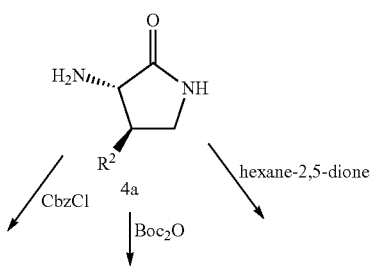

The following methods were used in the exemplified Examples, except where noted otherwise. Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (95% water, 5% ACN, 0.1% TFA) and Solvent B (5% water, 95% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 2% water, 10 mM $NH_4OAc$) or with gradients of Solvent A (98% water, 2% ACN, 0.1% $NH_4OH$) and Solvent B (98% ACN, 2% water, 0.1% $NH_4OH$).

LC/MS Methods Employed in Characterization of Examples. Reverse phase analytical HPLC/MS was performed on a Waters Acquity system coupled with a Waters MICROMASS® ZQ Mass Spectrometer.

Method A: Linear gradient of 0 to 100% B over 3 min, with 0.75 min hold time at 100% B;
  UV visualization at 220 nm
  Column: Waters BEH C18 2.1×50 mm
  Flow rate: 1.0 mL/min
  Solvent A: 0.1% TFA, 95% water, 5% acetonitrile
  Solvent B: 0.1% TFA, 5% water, 95% acetonitrile
Method B: Linear gradient of 0 to 100% B over 3 min, with 0.75 min hold time at 100% B;
  UV visualization at 220 nm
  Column: Waters BEH C18 2.1×50 mm
  Flow rate: 1.0 mL/min
  Solvent A: 10 mM ammonium acetate, 95% water, 5% acetonitrile
  Solvent B: 10 mM ammonium acetate, 5% water, 95% acetonitrile
Analytical HPLC: Methods Employed in Characterization of Examples Products were analyzed by reverse phase analytical HPLC: carried out on a Shimadzu Analytical HPLC: system running Discovery VP software. RT=retention time.
Method A: SunFire C18 column (3.5 µm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.
Method B: XBridge Phenyl column (3.5 µm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.
Method C: Ascentis Express C18, 2.1×50 mm, 2.7-µm particles; Solvent A: 95% water, 5% acetonitrile, 0.05% TFA; Solvent B: 95% acetonitrile, 5% water, 0.1% TFA; Temperature: 50° C.; Gradient: 0-100% B over 4 minutes, then a 1-minute hold at 100% B; Flow: 1.1 mL/min.
Method D: Ascentis Express C18, 2.1×50 mm, 2.7-µm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min.
NMR Employed in Characterization of Examples. $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). 1H NMR spectra were collected in d6-DMSO using a water suppression sequence, which effectively suppresses the water signal and any proton peaks in the same region usually between 3.30-3.65 ppm. Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

The following examples demonstrate a partial scope of the invention and are not meant to be limiting of the scope of the invention.

Intermediate 1. (3S,4R)-4-(2,6-difluoro-4-methoxyphenyl)-2-oxopyrrolidine-3-carboxylic Acid

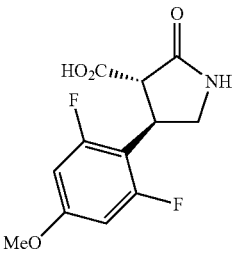

Step A. (E)-1,3-difluoro-5-methoxy-2-(2-nitrovinyl)benzene

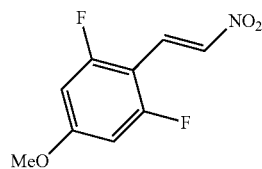 [SMILES: COc1cc(F)c(/C=C/[N+](=O)[O-])c(F)c1]

A solution of NaOH (0.244 g, 6.10 mmol) in water (1.50 mL) was added dropwise at −5° C. to a solution of 2,6-difluoro-4-methoxybenzaldehyde (1.00 g, 5.81 mmol) and nitromethane (0.313 mL, 5.81 mmol) in MeOH (25 mL). The solution was stirred at −5° C. for 1 h. The reaction mixture was quenched by addition of 1.5 N HCl at 0° C. (10 mL), and stirred for 10-15 min. The mixture was diluted with water and extracted with EtOAc (3×200 mL). The combined extracts were washed with brine, dried over $Na_2SO_4$, filtered and evaporated to provide 1-(2,6-difluoro-4-methoxyphenyl)-2-nitroethanol (1.25 g, 5.36 mmol, 92% yield) as a yellow gummy liquid. This was taken up in dry DCM (20 mL) and methanesulfonyl chloride (0.481 mL, 6.18 mmol) was added at 0° C. followed by TEA (1.44 mL, 10.3 mmol). The reaction mixture was stirred at 0° C. for 1 hr, then diluted with DCM, and washed with water and brine, dried over $Na_2SO_4$, filtered and evaporated. Purification by silica gel chromatography provided (E)-1,3-difluoro-5-methoxy-2-(2-nitrovinyl)benzene (0.9 g, 81% yield) as a yellow solid.

Step B. (R)-diethyl 2-(1-(2,6-difluoro-4-methoxyphenyl)-2-nitroethyl)malonate

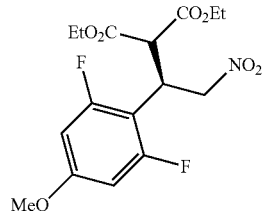 [SMILES: CCOC(=O)C(C(=O)OCC)[C@@H](C[N+](=O)[O-])c1c(F)cc(OC)cc1F]

To a solution of the compound of Step A (1.10 g, 5.11 mmol) in dry toluene (15 mL) was added diethyl malonate (0.936 mL, 6.14 mmol), and Nickel (II) bis [S,S]-N,N-dibenzylcyclohexan-1,2-diamine] bromide (0.411 g, 0.511 mmol) at 0° C., and the reaction mixture was stirred at rt ON. The solvent was removed in vacuo, and the crude was purified by silica gel chromatography to provide (R)-diethyl 2-(1-(2,6-difluoro-4-methoxyphenyl)-2-nitroethyl)malonate (1.70 g, 4.53 mmol, 89% yield) as a gummy liquid.

Step C. (3S,4R)-ethyl 4-(2,6-difluoro-4-methoxyphenyl)-2-oxopyrrolidine-3-carboxylate

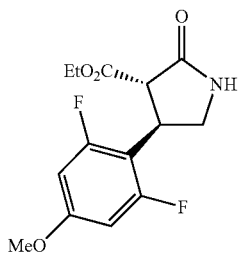

A solution of the compound of Step B (19.0 g, 50.6 mmol) in dry MeOH (250 mL) was charged to an autoclave flask and Raney nickel (13.0 g, 152 mmol) was added. The reaction mixture was kept under 15 Kg Hydrogen pressure with stirring at rt ON. The reaction mixture was filtered through a pad of celite, and solids washed with MeOH. The filtrate was then evaporated. The crude was purified by silica gel chromatography to provide (3S,4R)-ethyl 4-(2,6-difluoro-4-methoxyphenyl)-2-oxopyrrolidine-3-carboxylate (11.2 g, 74% yield) as an off white gummy solid.

Intermediate 1

To a solution of the compound of Step C (8.00 g, 26.7 mmol) in EtOH (80 mL) and THF (32 mL) was added 1M NaOH (1.28 g, 32.1 mmol) at 0° C. After completion of addition, the reaction mixture was stirred at 0° C. for 1 hr, than at rt for an additional 3-4 hrs. The solvent was removed, and the residue was diluted with water (100 mL). The aqueous solution was washed with MTBE (2×200 mL), then acidifed with 1.5N HCl at 0° C. to pH 1. The white solid which precipitated was collected and dried to provide the title compound (5.00 g, 66% yield) as a white solid.

Intermediate 2. N-((3S,4R)-4-(2,6-difluoro-4-methoxyphenyl)-2-oxopyrrolidin-3-yl)-1H-imidazole-1-carboxamide

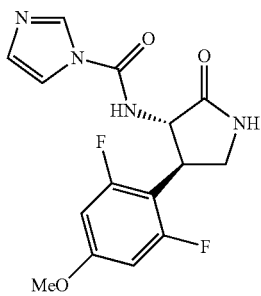 [SMILES: COc1cc(F)c([C@@H]2CNC(=O)[C@H]2NC(=O)n2ccnc2)c(F)c1]

To Intermediate 1 (300 g, 1.11 mol) was added acetonitrile (900 mL) and imidazole (226 g, 3.32 mol) at 21° C. to 26° C. The obtained mixture was heated at 32° C. to give a homogenous solution. The obtained homogenous solution was added dropwise to a solution of diphenyl phosphoryl azide (548 g, 1.99 mol) in acetonitrile (450 mL) at 65° C. over 2 hours and 50 minutes. After completing the dropping, the wall of dropping funnel was washed with acetonitrile (150 mL), the washing solution was added to the reaction solution, and the reaction solution was stirred at 65° C. for 50 minutes. The reaction mixture was cooled, triethylamine (448 g, 4.43 mol) was added thereto at 28° C. to 30° C. After a crystal therein arose, the mixture was stirred at 28° C. to 29° C. for 30 minutes. Water (1.50 L) was added to the obtained mixture at 28° C. to 29° C., and the mixture was stirred at 28° C. to 29° C. for 30 minutes. The mixture was cooled and stirred at 3° C. to 10° C. for 30 minutes. The precipitated solid was isolated on a filter and washed with water (1.50 L), and the solvent was removed. The obtained wet crystal was dried in vacuo to give the title compound as a white powder (304 g, 82%). MS(ESI) m/z: 337 (M+H). 1H NMR (500 MHz, DMSO-d6) δ 3.38 (1H, t, J=9.7 Hz), 3.54 (1H, t, J=9.2 Hz), 3.74 (3H, s), 3.93 (1H, q, J=9.8 Hz), 4.66 (1H, dd, J=11.1, 8.4 Hz), 6.76 (2H, d, J=10.7 Hz), 7.03 (1H, t, J=1.1 Hz), 7.61 (1H, t, J=1.5 Hz), 8.19 (1H, t, J=1.1 Hz), 8.33 (1H, s), 8.92 (1H, d, J=8.4 Hz).

Intermediate 3. (3S,4R)-3-Amino-4-(2,6-difluoro-4-methoxyphenyl)pyrrolidin-2-one

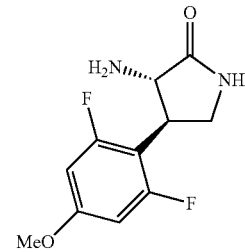 [SMILES: COc1cc(F)c([C@@H]2CNC(=O)[C@H]2N)c(F)c1]

Step A. (−)-[(3S*,4R*)-4-(4-Methoxyphenyl)-2-oxopyrrolidin-3-yl]carbamic Acid Benzyl Ester

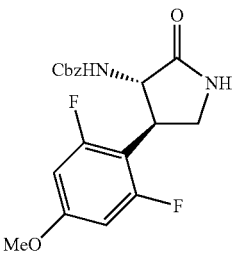 [SMILES: COc1cc(F)c([C@@H]2CNC(=O)[C@H]2NC(=O)OCc2ccccc2)c(F)c1]

Triethylamine (4.0 mL) and diphenylphosphorylazide (6.2 mL) were added to a solution of Intermediate 1 (6.04 g) in toluene (128 mL), and the reaction mixture was stirred at rt for 4.5 hours, followed by heating at 80° C. for 30 minutes. Benzyl alcohol (13.3 mL) was added, and the reaction mixture was stirred at 120° C. for 5 hours. The resulting solution was concentrated, and the residue was purified by silica gel column chromatography to obtain the title compound as a white solid (6.3 g). ¹HNMR (400 MHz, CDCl₃) δ 3.36 (1H, t, J=9.1 Hz), 3.49-3.70 (2H, m), 3.80 (3H, s), 4.42 (1H, dd, J=11.5, 8.5 Hz), 5.07 (2H, s), 20 5.16 (1H, brs), 5.98 (1H, brs), 6.89 (2H, d, J=7.9 Hz), 7.22 (2H, d, J=7.9 Hz), 7.20-7.40 (5H, m). $[\alpha]_D^{27}$=−79 (c 0.17, EtOH).

Intermediate 3. 10% Palladium on carbon (81 mg) was added to a solution of the compound of Step A (810 mg) in ethanol (30 mL). The reaction mixture was stirred under a hydrogen atmosphere for 2 hours. Catalyst was removed by filtration over Celite, and the solvent was removed under reduced pressure. The residue was purified by silica gel column chromatography to obtain the title compound as a white solid (520 mg). ¹H-NMR (400 MHz, DMSO-d₆) δ 3.22 (1H, t, J=8.0 Hz), 3.34-3.43 (2H, m), 3.47 (1H, d, J=9.8 Hz), 3.76 (3H, s), 6.74 (2H, d, J=11.020 Hz), 7.88 (1H, s). $[\alpha]_D^{24}$=−90 (c 0.11, EtOH).

Intermediate 4. tert-butyl ((3S,4R)-4-(2,6-difluoro-4-methoxyphenyl)-2-oxopyrrolidin-3-yl)carbamate

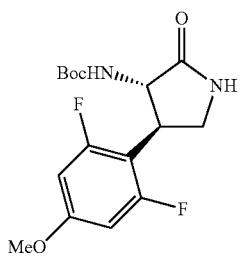

Step A. (3S,4R)-3-amino-4-(2,6-difluoro-4-methoxyphenyl)pyrrolidin-2-one

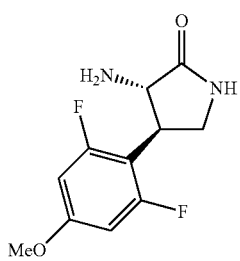

Intermediate 2 (2.78 g, 8.29 mmol) was dissolved in 1 N HCl (16.6 mL, 16.6 mmol), and the solution was heated at 70° C. for 5 h. The mixture was cooled to rt, and 5.6 g of solid NaCl was added, followed by enough water to just dissolve the salt. The reaction mixture was then made alkaline by addition of NaOH solution. The white solid was collected by filtration, washed with water and dried under vacuum to give the amine product (1.73 g, 86%) which was used without further purification.

Intermediate 4. The compound of Step A (1.25 g, 5.15 mmol) was dissolved in THF (20 ml), and TEA (1.44 ml, 10.3 mmol) and Boc₂O (1.79 ml, 7.72 mmol) were added. The mixture was stirred overnight under nitrogen at room temperature. The reaction mixture was diluted with EtOAc and water. The aqueous layer was re-extracted with EtOAc, and the combined extracts were washed with 5% aq. citric acid and brine, then dried over Na₂SO₄, filtered and evaporated. The residue was purified by flash chromatography to provide Intermediate 4 (1.53 g, 87%). MS (ESI) m/z 243.4 (M+H). ¹H NMR (400 MHz, DMSO-d₆) δ 7.87 (s, 1H), 6.85-6.62 (m, 2H), 3.77 (s, 3H), 3.52-3.45 (m, 1H), 3.45-3.32 (m, 2H), 3.26-3.19 (m, 1H), 1.74 (br s, 2H).

General Procedure for Synthesis of Cyclopropyl Amines 1c from Aryl or Heteroarylnitriles:

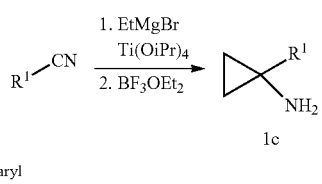

R¹ = aryl or heteroaryl

The aryl or heteroarylnitrile (1 eq) was dissolved in Et₂O, and titanium(IV) isopropoxide (1.1 eq.) was added. The mixture was cooled to −50° C., then a solution of 3.0 M ethylmagnesium bromide in ether (2.2 eq.) was added dropwise. The cooling bath was removed, and the reaction warmed to rt and stirred for 1h. Boron trifluoride etherate (2.2 eq.) was then added carefully dropwise, and stirring was continued ON at rt. The reaction mixture was diluted with additional Et₂O, quenched with ~10 mL 1M HCl and stirred until all solids were dissolved. Phases were separated, and the ether layer was washed with additional 1M HCl. The combined aqueous layers were adjusted to pH 12 with 10% aq. NaOH, then extracted 3× with EtOAc. The combined EtOAc layers were washed with brine, dried over Na₂SO₄, filtered and evaporated. The crude amines were typically used without further purification.

Example 1. 3-[1-(6-chloropyridin-2-yl)cyclopropyl]-1-[(3S,4R)-4-(2,6-difluoro-4-methoxyphenyl)-2-oxopyrrolidin-3-yl]urea

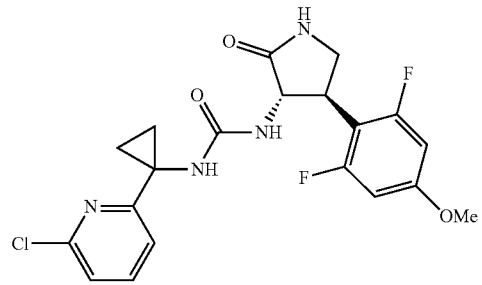 [SMILES: COc1cc(F)c([C@@H]2CNC(=O)[C@H]2NC(=O)NC2(c3cccc(Cl)n3)CC2)c(F)c1]

A mixture of 1-(6-chloropyridin-2-yl)cyclopropanamine, HCl (36.6 mg, 0.178 mmol) and Intermediate 2 (30.0 mg, 0.0890 mmol) in DMF (0.5 mL) were stirred overnight in DMF (0.5 mL) at 60° C. Purification by RP HPLC provided the title compound (25.9 mg, 67%) MS (ESI) m/z 437.3 (M+H). ¹NMR (500 MHz, DMSO-d6) δ 7.94 (br. s., 1H), 7.66 (t, J=7.7 Hz, 1H), 7.23-7.12 (m, 2H), 7.02 (br. s., 1H), 6.73 (d, J=10.9 Hz, 2H), 6.41 (d, J=8.4 Hz, 1H), 4.44 (t, J=9.0 Hz, 1H), 3.74 (m, 4H), 3.52-3.32 (m, 1H), 3.32-3.22 (m, 1H), 1.33 (br. s., 2H), 1.09 (br. s., 2H). Analytical HPLC retention time: 1.38 min (Method B).

Example 2. 1-[(3S,4R)-4-(2,6-difluoro-4-methoxy-phenyl)-2-oxopyrrolidin-3-yl]-3-[1-(4-methylphenyl)cyclopropyl]urea

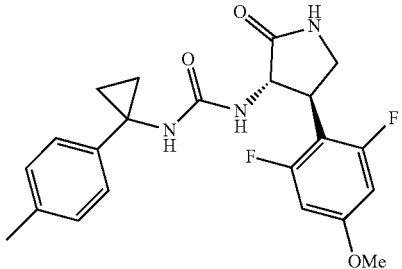 [SMILES: COc1cc(F)c([C@@H]2CNC(=O)[C@H]2NC(=O)NC2(c3ccc(C)cc3)CC2)c(F)c1]

2A. 1-(p-tolyl)cyclopropanamine

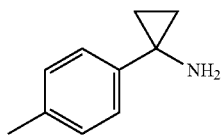

To a suspension of 1-(p-tolyl)cyclopropanecarboxylic acid (100 mg, 0.567 mmol) in DMF (0.284 mL) was added TEA (0.870 mL, 0.624 mmol) followed by dropwise addition of diphenylphosphoryl azide (0.135 mL, 0.624 mmol), and the mixture stirred ON at rt. The reaction mixture was heated to 100° C. and water (12 mL) and 1N HCl (2.5 mL) were added dropwise, and the resulting mixture stirred at 100° C. for 2 h. The reaction mixture was cooled to rt and extracted with EtOAc. The aqueous layer was neutralized with a 10% solution of sodium hydroxide to pH 10, and then extracted with ethyl acetate. The combined EtOAc extracts were washed with brine, dried over Na$_2$SO$_4$ and evaporated to give 2A (20 mg, 24%). MS (ESI) m/z 148 (M+H).
Example 2. Example 2 was prepared from Intermediate 2 and 2A using the procedure described for Example 1. MS (ESI) m/z 416.3 (M+H). $^1$H NMR (500 MHz, DMSO-d6) δ 7.92 (br. s., 1H), 6.98 (d, J=7.4 Hz, 2H), 6.92-6.77 (m, 3H), 6.72 (d, J=10.8 Hz, 2H), 6.19 (d, J=8.2 Hz, 1H), 4.45 (br t, J=9.5 Hz, 1H), 3.76 (s, 4H), 3.43-3.35 (m, 1H), 3.28 (br t, J=9.5 Hz, 1H), 2.22 (s, 3H), 1.15-0.92 (m, 4H). Analytical HPLC retention time: 1.46 min (Method D).

Example 3. 1-[(3S,4R)-4-(2,6-difluoro-4-methoxy-phenyl)-2-oxopyrrolidin-3-yl]-3-[1-(3,5-dimethylphenyl)cyclopropyl]urea

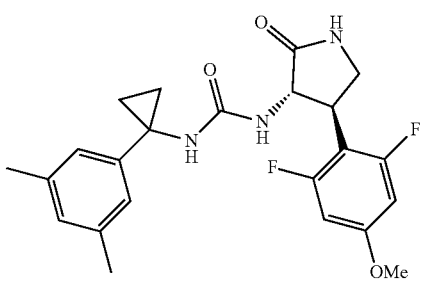 [SMILES: COc1cc(F)c([C@@H]2CNC(=O)[C@H]2NC(=O)NC2(c3cc(C)cc(C)c3)CC2)c(F)c1]

3A. 1-(3,5-dimethylphenyl)cyclopropanamine

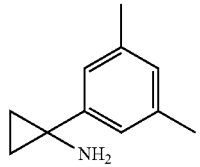

To a solution of 3,5-dimethylbenzonitrile (250 mg, 1.91 mmol) and titanium(IV) isopropoxide (0.614 mL, 2.10 mmol) in Et$_2$O (8.74 mL) was slowly added a 3M solution of EtMgBr in Et$_2$O (1.40 mL, 4.19 mmol) at −50° C. under nitrogen. The mixture was warmed up to rt for 1 hr. BF$_3$.OEt$_2$ (0.483 mL, 3.81 mmol) was then added slowly. The mixture was stirred at rt ON. The reaction was quenched by dropwise addition of −10 mL of 1N HCl. Ether (150 mL) was added to extract the aqueous layer. The organic layer was again washed with 1N HCl. The combined aqueous layers were neutralized with 10% wt NaOH to pH=12, then extracted with EtOAc. The solvent was removed to give 3A as a yellow oil (179 mg, 58%). MS (ESI) m/z 162.1 (M+H).
Example 3. Example 3 was prepared from Intermediate 2 and 3A as described for Example 1. MS (ESI) m/z 430.1 (M+H). $^1$H NMR (500 MHz, DMSO-d6) δ 7.89 (br. s., 1H), 6.78 (s, 1H), 6.75-6.64 (m, 3H), 6.61 (s, 2H), 6.18 (d, J=8.2 Hz, 1H), 4.44 (br t, J=9.5 Hz, 1H), 3.74 (s, 3H), 3.61-3.58 (m, 1H), 3.58 (br s, 1H), 3.40 (br t, J=9.0 Hz, 1H), 3.27 (br t, J=9.6 Hz, 1H), 2.16 (s, 6H), 1.05 (br. s., 4H). Analytical HPLC Retention time: 1.66 min (Method D).

Example 4. 1-[(3S,4R)-4-(2,6-difluoro-4-methoxy-phenyl)-2-oxopyrrolidin-3-yl]-3-[1-(1,5-naphthyridin-2-yl)cyclopropyl]urea

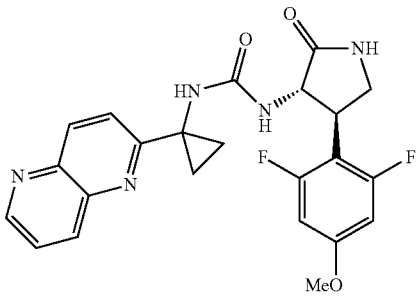 [SMILES: COc1cc(F)c([C@@H]2CNC(=O)[C@H]2NC(=O)NC2(c3ccc4ncccc4n3)CC2)c(F)c1]

4A. tert-butyl (1-(methoxy(methyl)carbamoyl)cyclopropyl)carbamate

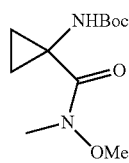

A mixture of 1-((tert-butoxycarbonyl)amino)cyclopropanecarboxylic acid (0.50 g, 2.5 mmol), HATU (1.13 g, 2.98 mmol), N,O-dimethylhydroxylamine hydrochloride (0.267 g, 2.73 mmol) and DIPEA (2.17 mL, 12.4 mmol) in DMF (5.0 ml) was stirred at rt under nitrogen for ~2h. The reaction was diluted with EtOAc and poured into 1M NaOH. The phases were separated, and the aqueous layer was extracted with EtOAc (2×). The combined extracts were washed with water and brine, dried over $Na_2SO_4$, filtered and evaporated. The residue was purified by flash chromatography to provide 4A as a colorless, crystalline solid. (0.472 g, 78%). MS (ESI) m/z 245.5 (M+H).

4B. tert-butyl (1-acetylcyclopropyl)carbamate

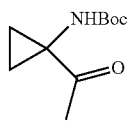

4A (0.245 g, 1.00 mmol) was dissolved in THF, and the solution cooled to 0° C. in an ice/salt water bath under nitrogen. A solution of methylmagnesium bromide, 3M in ether (1.00 mL, 3.01 mmol) was added dropwise, and the reaction mixture was allowed to slowly assume rt then stirred ON. The reaction mixture was quenched with saturated aq. $NH_4Cl$ and extracted with EtOAc (3×). The combined extracts were washed with brine, then dried over $Na_2SO_4$, filtered and evaporated. The residue was purified by flash chromatography to provide 4B as a white crystalline solid, (0.128 g, 64% yield). MS (ESI) m/z 200.4 (M+H).

4C. tert-butyl (1-(1,5-naphthyridin-2-yl)cyclopropyl)carbamate

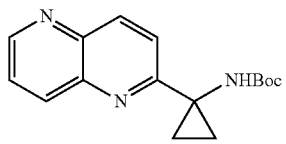 [SMILES: CC(C)(C)OC(=O)NC1(c2ccc3ncccc3n2)CC1]

Freshly powdered NaOH (10.6 mg, 0.265 mmol) was dissolved in ethanol (1.0 mL) and stirred at rt under nitrogen. A solution of tert-butyl (1-acetylcyclopropyl)carbamate (23.0 mg, 0.115 mmol) and 3-aminopicolinaldehyde (14.4 mg, 0.118 mmol) in ethanol (1.0 mL) was then added, and the reaction mixture was stirred at rt. The reaction mixture was evaporated. The residue was purified by flash chromatography to provide 4C (22 mg, 67%) MS (ESI) m/z 286.5 (M+H).

4D. 1-(1,5-naphthyridin-2-yl)cyclopropanamine, 2 HCl

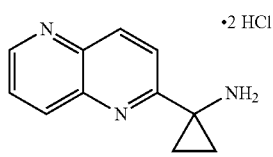 [SMILES: NC1(c2ccc3ncccc3n2)CC1]

4C (22 mg, 0.077 mmol) was dissolved in dioxane (0.5 mL), and a solution of 4N HCl in dioxane (0.50 mL, 2.0 mmol) was added. A thick gelatinous precipitate formed which prevented stirring of the mixture. The reaction was diluted with a little MeOH (~1 mL) to obtain a clear solution, which was then stirred at rt for 2.5 h. The reaction mixture was diluted with a little additional MeOH and evaporated to provide 4D as an off-white solid which was dried ON in vacuo and used without further purification (20 mg, 100%). MS (ESI) m/z 186.4 (M+H). Example 4 was prepared from Intermediate 2 and 4D as described for Example 1. MS (ESI) m/z: 454.4 (M+H). $^1$H NMR (500 MHz, DMSO-d6) δ 8.87 (d, J=3.05 Hz, 1H), 8.20 (t, J=8.54 Hz, 2H), 7.92 (br s, 1H), 7.69 (dd, J=8.54, 3.97 Hz, 1 H), 7.16 (s, 1H) 7.58-7.65 (m, 1H), 6.72 (br d, J=10.99 Hz, 2H), 6.46 (br d, J=8.54 Hz, 1H), 4.47 (br t, J=9.77 Hz, 1H), 3.57-3.65 (m, 1H) 3.74 (s, 3H), 3.36-3.44 (m, 1H), 3.30 (br t, J=9.46 Hz, 1H), 1.59 (br d, J=18.01 Hz, 2H), 1.19 (br s, 2H). Analytical HPLC retention time: 0.96 min (Method A).

Example 5. 3-[1-(1,3-benzoxazol-2-yl)cyclopropyl]-1-[(3S,4R)-4-(2,6-difluoro-4-methoxyphenyl)-2-oxopyrrolidin-3-yl]urea

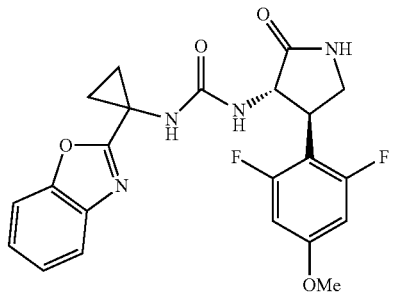 [SMILES: COc1cc(F)c([C@@H]2CNC(=O)[C@H]2NC(=O)NC2(c3nc4ccccc4o3)CC2)c(F)c1]

5A. Tert-Butyl (1-(hydroxymethyl)cyclopropyl)carbamate

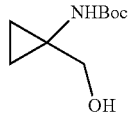

1-((tert-butoxycarbonyl)amino)cyclopropanecarboxylic acid (1.00 g, 4.97 mmol) was dissolved in DME (10 mL) under nitrogen with stirring. N-methylmorpholine (0.546 mL, 4.97 mmol) was added, and the mixture was cooled to −15° C. Isobutyl chloroformate (0.653 mL, 4.97 mmol) was added dropwise. The reaction mixture was stirred for 10 min, then filtered into a 100 mL flask cooled in an ice/salt water bath. Solids were washed with 2 small portions of DME, then a solution of $NaBH_4$ (0.282 g, 7.45 mmol) in water (2.0 mL) was added rapidly to the stirred mixture. Stirring was continued at 0° C. for 20 min, then the reaction was quenched with water and extracted with EtOAc (3×). The combined extracts were washed with brine, dried over $Na_2SO_4$, filtered and evaporated. 5A was obtained as a clear oil that crystallized on standing (0.86 g, 92% yield) and was used without further purification. MS (ESI) m/z 188.4 (M+H).

5B. Tert-Butyl (1-formylcyclopropyl)carbamate

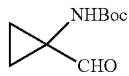

A solution of DMSO (0.391 mL, 5.51 mmol) in DCM (2.4 mL) was added dropwise to a solution of oxalyl chloride (0.482 mL, 5.51 mmol) in DCM (12 mL) at −70° C. with stirring under nitrogen. The mixture was stirred for 5 min, then a solution of 5A (0.860 g, 4.59 mmol) in DCM (2.4 mL) was added dropwise. The mixture was stirred at −70° C. for 15 min, and then TEA (3.20 mL, 23.0 mmol) was added. After an additional 5 min at −70° C., the cooling bath was removed, and the reaction mixture was allowed to slowly warm to rt. Stirring was continued for 1 h. The reaction was quenched with water and poured into DCM. The phases were separated, and the aq. layer was extracted with DCM (2×). The combined extracts were washed with brine, dried over $Na_2SO_4$ and filtered. The filtrate was evaporated, and the residue was purified by flash chromatography to provide 5B as a white crystalline solid (0.513 g, 60%) was obtained. MS (ESI) m/z 186.4 (M+H).

5C. Tert-Butyl (1-(benzo[d]oxazol-2-yl)cyclopropyl)carbamate

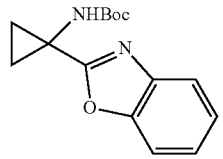 [SMILES: CC(C)(C)OC(=O)NC1(c2nc3ccccc3o2)CC1]

To a mixture of 5B (0.15 g, 0.81 mmol) and 2-aminophenol (0.093 g, 0.85 mmol) in MeOH (2.5 mL) in a pressure-rated vial was added 3A molecular sieves (~10-12 pellets). The vial was flushed with nitrogen, capped and heated in a pie block at 45° C. ON with gentle stirring. The sieves were removed by filtration, and the filtrate was evaporated. The residue was taken up in DCM (2.5 mL), and DDQ (0.20 g, 0.89 mmol) was added. The mixture was stirred for 1 h under nitrogen at rt, then quenched by addition of saturated aq. $NH_4Cl$ and diluted with additional DCM. This mixture was transferred to separatory funnel, and phases separated. The aqueous layer was extracted with DCM (2×), and the combined extracts were washed with brine, dried over $Na_2SO_4$, filtered and evaporated. The residue was purified by flash chromatography to provide 5C as a dark brown oil (0.053 g, 24% yield). MS (ESI) m/z 275.5 (M+H).

5D. 1-(benzo[d]oxazol-2-yl)cyclopropanamine, HCl

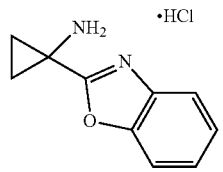 [SMILES: Cl ; NC1(c2nc3ccccc3o2)CC1]

5C (0.053 g, 0.19 mmol) was taken up in dioxane (1.0 mL) and 4N HCl in dioxane (1.0 mL) was added. The reaction mixture was stirred at rt for 2h, diluted with a little MeOH and evaporated to dryness to provide 5D which was dried in vacuo and used without purification in the next step. (ESI) m/z 175.4 (M+H). Example 5. A mixture of Intermediate 2 (25 mg, 0.074 mmol), 5D (16 mg, 0.074 mmol) and TEA (0.031 mL, 0.22 mmol) in DMF (0.85 mL) was stirred at rt ON. Purification by RP-HPLC provided the title compound (7.3 mg, 21%). MS (ESI) m/z: 443.3 (M+H). $^1$H NMR (500 MHz, DMSO-d6) δ 7.93 (s, 1H), 7.46-7.63 (m, 2H), 7.26-7.36 (m, 2H), 7.15 (s, 1H), 6.67 (br d, J=10.99 Hz, 2H), 6.49 (br d, J=8.24 Hz, 1H), 4.45 (br t, J=9.61 Hz, 1H), 3.73-3.80 (m, 1H), 3.32-3.45 (m, 1H) 3.71 (s, 3H), 3.26 (br t, J=9.46 Hz, 1H), 1.51 (br s, 2H), 1.18-1.33 (m, 2H). Analytical HPLC retention time: 1.39 min (Method C).

Example 6. 1-[(3S,4R)-4-(2,6-difluoro-4-methoxyphenyl)-2-oxopyrrolidin-3-yl]-3-[1-(5-methyl-1,3-oxazol-2-yl)cyclopropyl]urea

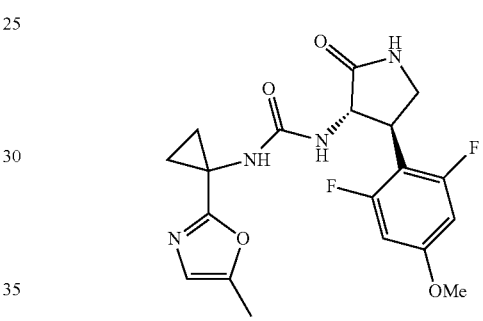

6A. tert-butyl (1-((2-hydroxypropyl)carbamoyl)cyclopropyl)carbamate

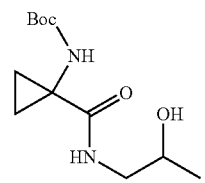 [SMILES: CC(O)CNC(=O)C1(NC(=O)OC(C)(C)C)CC1]

1-((tert-butoxycarbonyl)amino)cyclopropanecarboxylic acid (0.200 g, 0.994 mmol) was dissolved in DMF (5 mL) with stirring under nitrogen, and TBTU (0.383 g, 1.19 mmol) and TEA (0.180 mL, 1.29 mmol) were added. The mixture was stirred for 1 h at rt. 1-aminopropan-2-ol (0.084 mL, 1.1 mmol) was then added and stirring continued at rt ON. The reaction mixture was diluted with water and extracted with EtOAc (3×). The combined extracts were washed with water (2×), saturated aq $NaHCO_3$ and brine, dried over $Na_2SO_4$, filtered and evaporated. The crude product 6A was used without purification in next step (0.119 g, 46%). MS (ESI) m/z 257.5 (M+H).

6B. tert-butyl (1-((2-oxopropyl)carbamoyl)cyclopropyl)carbamate

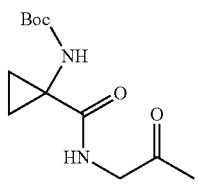 [SMILES: CC(=O)CNC(=O)C1(NC(=O)OC(C)(C)C)CC1]

6A (0.119 g, 0.461 mmol) was dissolved in DCM (4 mL), and Dess-Martin periodinane (0.293 g, 0.691 mmol) was added. The mixture was stirred at rt for 1 h. The reaction was quenched with saturated aq NaHCO₃ and additional DCM was added. The phases were separated, and the aq. layer was extracted with DCM (2×). The combined extracts were washed with brine, dried over Na₂SO₄, filtered and evaporated to provide 6B (0.118 g, 100%), which was used without further purification. MS (ESI) m/z 257.5 (M+H).

6C. tert-butyl (1-(5-methyloxazol-2-yl)cyclopropyl)carbamate

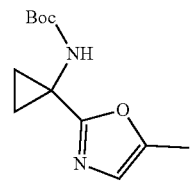 [SMILES: Cc1cnc(C2(NC(=O)OC(C)(C)C)CC2)o1]

6B (0.118 g, 0.460 mmol) was dissolved in THF (2.0 ml) in a 5 mL microwave vial, and Burgess reagent (0.132 g, 0.552 mmol) was added. The vial was flushed with nitrogen and capped. The vial was placed in a preheated pie-block at 100° C. and heated for 5-10 min. An additional aliquot of Burgess reagent (0.132 g, 0.552 mmol) was added. The vial was recapped and again heated at 100° C. for an additional 10-15 min. The reaction was cooled to rt and diluted with DCM, washed with water and brine. The organic layer was dried over Na₂SO₄, filtered and evaporated. The residue was purified by flash chromatography to provide 6C (63 mg, 57% yield). MS (ES) m/z 239.1 (M+H).

6D 1-(5-methyloxazol-2-yl)cyclopropanamine, HCl

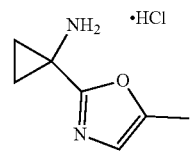

6D was prepared from 6C using the procedure described for 50D. MS (ES) m/z 139.1 (M+H).
Example 6 was prepared from Intermediate 2 and 6D as described for Example 1. MS (ESI) m/z 407.1 (M+H). ¹H NMR (500 MHz, DMSO-d6) δ 7.93 (s, 1H), 6.96 (s, 1H), 6.69 (br d, J=10.99 Hz, 2H), 6.59 (s, 1H), 6.33 (br d, J=8.24 Hz, 1H), 4.44 (br t, J=9.61 Hz, 1H), 3.67-3.77 (m, 1H) 3.74 (s, 3H), 3.33-3.46 (m, 1 H), 3.25 (br t, J=9.61 Hz, 1H), 2.16 (s, 3H), 1.18-1.32 (m, 2H), 0.94-1.12 (m, 2H). Analytical HPLC retention time: 1.24 min (Method B).

Example 7. 1-[(3S,4R)-4-(2,6-difluoro-4-methoxyphenyl)-2-oxopyrrolidin-3-yl]-3-[1-(4-methoxy-1,3-benzothiazol-2-yl)cyclopropyl]urea

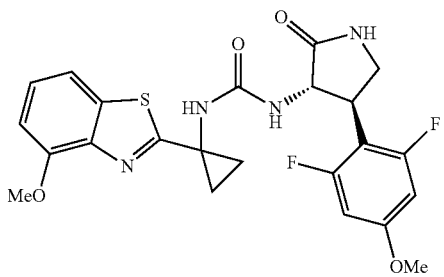 [SMILES: COc1cc(F)c([C@@H]2CNC(=O)[C@H]2NC(=O)NC2(c3nc4c(OC)cccc4s3)CC2)c(F)c1]

7A. 2-bromo-4-methoxybenzo[d]thiazole

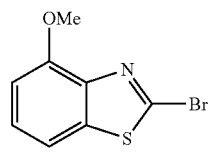 [SMILES: COc1cccc2sc(Br)nc12]

To a suspension of 4-methoxybenzo[d]thiazol-2-amine (0.620 g, 3.40 mmol) and p-TSA monohydrate (1.96 g, 10.3 mmol) in acetonitrile (20 mL) at 10° C. was added dropwise a solution of NaNO₂ (0.475 g, 6.88 mmol) and KBr (1.13 g, 9.46 mmol) in water (5 mL) over a period of 25 min. The reaction was stirred at 10° C. for 10 min, and then allowed to warm up to rt and stirred for 2.0 h. To the reaction mixture was added sodium bicarbonate (pH to 9.0), water and EtOAc. The organic layer was collected, washed with water, saturated aq Na₂S₂O₃, water, brine, and dried over Na₂SO₄. After evaporation of solvent, the crude product was purified by flash chromatography to give 7A (0.56 g, 67% yield) as a slightly yellow solid. MS (ESI) m/z: 244.0/246.0 (M+H). ¹H NMR (500 MHz, CCCl₃) δ 7.40-7.37 (m, 2H), 6.92 (dd, J=6.3, 2.5 Hz, 1H), 4.06 (s, 3H).

7B. 4-methoxybenzo[d]thiazole-2-carbonitrile

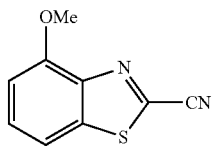 [SMILES: COc1cccc2sc(C#N)nc12]

A microwave vial was charged with copper(I) cyanide (89 mg, 0.99 mmol) and 7A (220 mg, 0.91 mmol) in DMF (0.45 mL). The mixture was heated to 200° C. for 30 mins in a microwave reactor. The resulting black solution was diluted with EtOAc (~100 mL) and filtered, and the filtrated was washed with water and brine, then dried over Na₂SO₄. The residue was purified by flash chromatography to provide 7B (68 mg, 40%). MS (ESI) m/z 191.0 (M+H).

7C. 1-(4-methoxybenzo[d]thiazol-2-yl)cyclopropan-amine

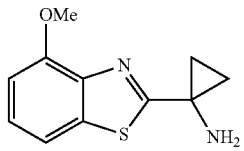 [SMILES: COc1cccc2sc(C3(N)CC3)nc12]

7C was prepared from 7B following the general procedure for synthesis of cyclopropyl amines described above. To a solution of 7B (68.0 mg, 0.360 mmol) and Ti(OiPr)$_4$ (115 μl, 0.393 mmol) in Et$_2$O (1640 μl) was slowly added a 3M solution of EtMgBr in Et$_2$O (262 μl, 0.786 mmol) at −50° C. under nitrogen. The mixture was then warmed up to rt for 1 hr. BF$_3$.OEt$_2$ (91.0 μl, 0.720 mmol) was then added slowly. The mixture was stirred at rt for 3 days. The reaction was quenched by dropwise addition of ~10 mL of 1N HCl. Additional ether was added to extract the aqueous layer. The organic layer was again washed with 1N HCl. The combined aqueous layers were neutralized with 10% aq. NaOH to pH=12, then extracted with EtOAc. The solvent was removed from the latter extract to give 7C which was used without further purification, (28.5 mg, 36% yield). MS (ESI) m/z 221.0 (M+H).

Example 7. The title compound was prepared from Intermediate 2 and 7C using the procedure described for Example 1. MS (ESI) m/z 489.06 (M+H). $^1$H NMR (500 MHz, DMSO-d$_6$) δ 7.95 (br s, 1H), 7.48 (br d, J=7.9 Hz, 1H), 7.40 (s, 1H), 7.29 (t, J=8.1 Hz, 1H), 6.97 (d, J=7.9 Hz, 1H), 6.71 (br d, J=10.7 Hz, 2H), 6.50 (br d, J=8.2 Hz, 1H), 4.60-4.44 (m, 1H), 3.89 (s, 3H), 3.81-3.74 (m, 1H), 3.72 (s, 3H), 3.61-3.36 (m, 1H), 3.30 (br t, J=9.5 Hz, 1H), 1.65-1.47 (m, 2H), 1.33-1.17 (m, 2H). Analytical HPLC Retention Time: 1.32 min (Method D).

Example 8. 1-[(3S,4R)-4-(2,6-difluoro-4-methoxyphenyl)-1-methyl-2-oxopyrrolidin-3-yl]-3-[1-(quinolin-2-yl)cyclopropyl]urea

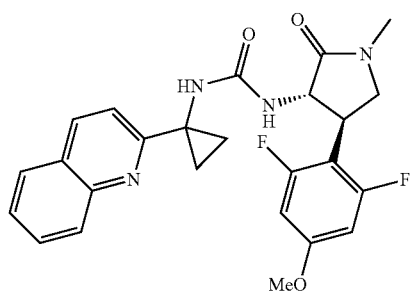 [SMILES: COc1cc(F)c([C@@H]2CN(C)C(=O)[C@H]2NC(=O)NC2(c3ccc4ccccc4n3)CC2)c(F)c1]

8A. tert-butyl ((3S,4R)-4-(2,6-difluoro-4-methoxyphenyl)-2-oxopyrrolidin-3-yl)carbamate

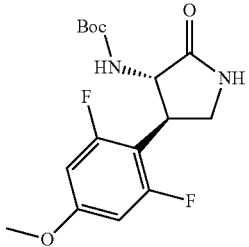 [SMILES: COc1cc(F)c([C@@H]2CNC(=O)[C@H]2NC(=O)OC(C)(C)C)c(F)c1]

Intermediate 3 (0.40 g, 1.6 mmol) was dissolved in THF (8.3 mL), and TEA (0.92 mL, 6.6 mmol) and Boc$_2$O (0.54 g, 2.5 mmol) were added. The mixture was stirred ON under nitrogen at rt. The reaction mixture was diluted with EtOAc and water. The aq. layer was extracted with EtOAc, and the combined extracts were washed with 5% aq. citric acid and brine, then dried over Na$_2$SO$_4$, filtered and evaporated. The residue was purified by flash chromatography to provide 8A as a white foam. (0.51 g, 90%). MS (ESI) m/z 343.3 (M+H).

8B. tert-butyl ((3S,4R)-4-(2,6-difluoro-4-methoxyphenyl)-1-methyl-2-oxopyrrolidin-3-yl)carbamate.

8A (0.51 g, 1.5 mmol) was dissolved in THF (7.5 mL) under nitrogen, and the solution was cooled to 0° C. A solution of 1M KHMDS in THF (1.5 mL, 1.5 mmol) was added dropwise with stirring, followed after ~5 min by dropwise addition of MeI (0.14 mL, 2.2 mmol). The reaction mixture was stirred at 0° C. for ~1 h, then ON at rt. The reaction mixture was diluted with water and extracted with EtOAc (3×). The combined extracts were washed with brine, dried over Na$_2$SO$_4$, filtered and evaporated. The residue was purified by flash chromatography to provide 8B (0.39 g, 73%) contaminated with a little dimethylated product. The product was used without further purification. MS (ESI) m/z 357.3 (M+H).

8C. (3S,4R)-3-amino-4-(2,6-difluoro-4-methoxyphenyl)-1-methylpyrrolidin-2-one

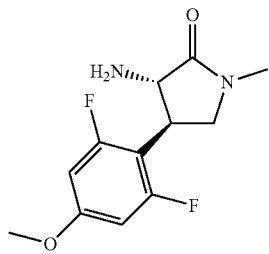

8B (0.16 g, 0.45 mmol) was dissolved in a mixture of dioxane (1.0 mL) and 4N HCl in dioxane (1.0 mL, 4.0 mmol). The solution was stirred at rt for 2.5 h. The reaction mixture was diluted with MeOH and evaporated. The residue was redissoved in DCM and stirred with 1.5 M aq. $K_2HPO_4$ solution for 1 h. The phases were separated, and aq. layer was extracted with DCM (3×). The combined organic layers were dried over $Na_2SO_4$, filtered and evaporated to provide 8C as a white solid which was used without further purification. MS (ESI) m/z 257.2 (M+H).

8D. 1-(quinolin-2-yl)cyclopropanamine

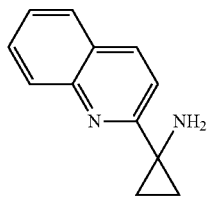 [SMILES: NC1(c2ccc3ccccc3n2)CC1]

To a solution of quinoline-2-carbonitrile (250 mg, 1.62 mmol) and titanium(IV) isopropoxide (0.523 mL, 1.78 mmol) in $Et_2O$ (7.4 mL) was slowly added a solution of 3M EtMgBr in $Et_2O$ (0.119 mL, 3.57 mmol) at −50° C. under nitrogen. The mixture was warmed up to rt for 1 h. $BF_3 \cdot OEt2$ (0.411 mL, 3.24 mmol) was added slowly. The mixture was stirred at rt ON. The reaction was quenched by dropwise addition of ~10 mL of 1N HCl, and 150 mL of ether was added to extract the aqueous layer. The organic layer was again washed with 1N HCl. The combined aqueous layers were neutralized with 10% wt NaOH to pH=12, then extracted with EtOAc. The solvent was evaporated to give the crude product 8D as a dark brown oil residue (235 mg, 79%). MS (ESI) m/z 185.2 (M+H).

Example 8. CDI (14 mg, 0.086 mmol) was added to a solution of 8C (20 mg, 0.078 mmol) in DCM (0.2 mL), and the mixture was stirred for ~5 min at rt under nitrogen. A solution of 8D (16 mg, 0.087 mmol) in DCM (0.10 mL) was then added along with an additional 0.10 mL DCM as rinse. Stirring was continued ON at rt. Reaction mixture was evaporated, and the residue purified by RP-HPLC to provide the title compound (6.0 mg, 16%). MS (ESI) m/z: 467.0 (M+H). $^1$H NMR (500 MHz, DMSO-$d_6$) δ ppm 1.15 (br s, 2H) 1.47-1.66 (m, 2H) 2.79 (s, 3H) 3.28-3.48 (m, 1H) 3.48-3.55 (m, 2H) 3.74 (s, 3H) 4.48 (br t, J=9.21 Hz, 1H) 6.52 (br d, J=8.25 Hz, 1H) 6.75 (br d, J=10.94 Hz, 2H) 7.19 (br s, 1H) 7.43 (br d, J=7.32 Hz, 1H) 7.49 (br t, J=7.45 Hz, 1H) 7.67 (br t, J=7.66 Hz, 1H) 7.80 (br d, J=8.33 Hz, 1H) 7.90 (br d, J=8.08 Hz, 1H) 8.17 (br d, J=8.50 Hz, 1H). Analytical HPLC retention time: 1.11 min (Method C).

Example 9. 1-[(3S,4R)-4-(2-fluoro-4-methoxyphenyl)-2-oxopyrrolidin-3-yl]-3-[1-(6-methylpyridin-2-yl)cyclopropyl]urea

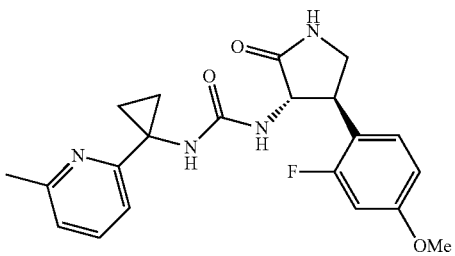 [SMILES: COc1ccc([C@@H]2CNC(=O)[C@H]2NC(=O)NC2(c3cccc(C)n3)CC2)c(F)c1]

9A. (E)-2-fluoro-4-methoxy-1-(2-nitrovinyl)benzene

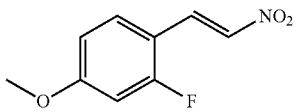

2-fluoro-4-methoxybenzaldehyde (10 g, 65 mmol) was dissolved in 2-hydroxyethanaminium formate (7.0 g, 65 mmol) and nitromethane (11 mL, 0.20 mol) was added. The resulting reaction mixture was stirred at rt for 10h. The reaction mixture was quenched with water and the resulting precipitate was collected by filtration, washed with petroleum ether and dried under vacuum to provide 9A (8.0 g, 63% yield) as an orange solid.

9B. (R)-diethyl 2-(1-(2-fluoro-4-methoxyphenyl)-2-nitroethyl)malonate

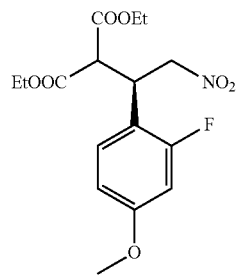 [SMILES: CCOC(=O)C(C(=O)OCC)[C@@H](C[N+](=O)[O-])c1ccc(OC)cc1F]

To a solution of 9A (2.00 g, 10.1 mmol) in dry toluene (10 mL) was added diethyl malonate (1.55 mL, 10.1 mmol) and (3aS,3'aS,7aS,7'aS)-1,1',3,3'-tetrabenzyl-2,2-dibromo-hexadecahydro-2,2'-spirobi[cyclohexa[d]1,3-diaza-2-nickelacyclopentane] (0.407 g, 0.507 mmol) at 0° C., and the reaction mixture was stirred at rt for 15h. Purification by flash chromatography provided 9B (3.0 g, 66% yield).

9C. (3S,4R)-ethyl 4-(2-fluoro-4-methoxyphenyl)-2-oxopyrrolidine-3-carboxylate

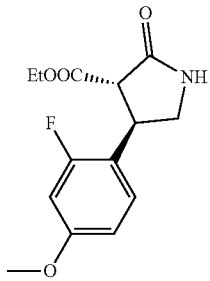 [SMILES: CCOC(=O)[C@@H]1C(=O)NC[C@H]1c1ccc(OC)cc1F]

To a solution of 9B (2.8 g, 7.8 mmol) in methanol (20 mL) was carefully added aluminum-nickel alloy (2.0 g, 24 mmol), and the reaction mixture was stirred at 284 psi hydrogen at rt for 15h. The reaction mixture was filtered through celite bed, and the solids washed with MeOH (100 mL). The filtrate was concentrated, and the residue was purified by silica gel chromatography to provide 9C (2.0 g, 73% yield) as colorless liquid.

9D. (3S,4R)-4-(2-fluoro-4-methoxyphenyl)-2-oxopyrrolidine-3-carboxylic Acid

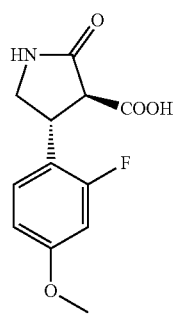

To a solution of 9C (2.0 g, 7.1 mmol) in EtOH (20 mL) and THF (6 mL) was added NaOH (7.1 mL, 7.1 mmol) at 0° C. After completion of addition, the reaction mixture was stirred at 0° C. for 1 hr and then rt for 3-4 hrs. The solvent was removed completely, and the reaction mixture was diluted with water (10 mL), and the aqueous layer was washed with MTBE (2×20 mL). The aqueous layer was then acidified with 1.5 N HCl at 0° C. to pH 1. The white solid which precipitated was collected by filtration and dried under vacuum for 15h to provide 9D (1.2 g, 4.6 mmol, 65% yield) as a white solid. MS (ESI) m/z 254.1 (M+H).

9E. benzyl ((3S,4R)-4-(2-fluoro-4-methoxyphenyl)-2-oxopyrrolidin-3-yl)carbamate

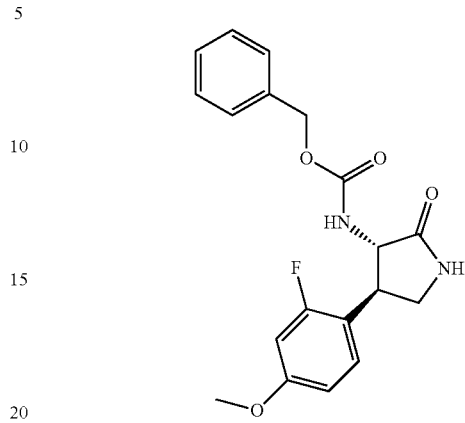

To a solution of 9D (0.80 g, 3.2 mmol) in toluene (30 mL) was added TEA (0.48 mL, 3.5 mmol) and diphenylphosphoryl azide (0.75 mL, 3.5 mmol). The resulting mixture was stirred at rt for 4.5h, then heated at 80° C. for 30 min. The reaction mixture was cooled to rt, and benzyl alcohol (1.6 mL, 16 mmol) was added. The mixture was then heated at 110° C. for 5h. Ethyl acetate was added to the reaction solution, and the mixture was washed with 1 M HCl, water, and brine successively, then dried over $Na_2SO_4$, filtered and evaporated. The residue was purified by RP-HPLC to provide 9E (0.35 g, 26%). MS (ESI) m/z 359.2 (M+H).

9F. (3S,4R)-3-amino-4-(2-fluoro-4-methoxyphenyl)pyrrolidin-2-one

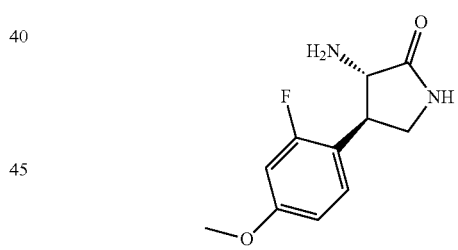

To a nitrogen purged solution of 9E (350 mg, 0.98 mmol) in ethanol (5 mL) was added Pd/C (35 mg, 0.33 mmol), and the mixture was stirred under a hydrogen balloon for 2h. The reaction mixture was filtered through a celite bed, and the solids were washed with methanol. The filtrate was evaporated to give 9F (190 mg, 87%) as an off white solid. MS (ESI) m/z 225.2 (M+H).

Example 9. To a 0° C. cooled solution of 1-(6-methylpyridin-2-yl)cyclopropanamine (60 mg, 0.40 mmol) and TEA (0.34 mL, 2.4 mmol) in THF (3 mL) was added a solution of triphosgene (48 mg, 0.16 mmol) in THF (2 mL) dropwise. The reaction mixture was stirred for 15 min at 0° C. A solution of 9F (50 mg, 0.22 mmol) and DIPEA (0.14 mL, 0.81 mmol) in DCM (2 mL) was then added dropwise and stirring was continued at 0° C. for another 15 min then at rt for 3 h. The reaction mixture was evaporated, and the residue was purified by RP-HPLC to provide the title compound (3.9 mg, 2.3%). MS (ESI) m/z 399.0 (M+H). $^1$H NMR (400 MHz, DMSO-d$_6$) δ 7.84 (s, 1H), 7.48-7.37 (m, 2H), 7.04 (d, J=7.8 Hz, 1H), 6.94 (d, J=7.8 Hz, 1H), 6.86-6.72 (m, 3H), 6.25 (d, J=9.0 Hz, 1H), 4.46 (dd, J=11.1, 8.9 Hz, 1H), 3.75 (s, 3H), 3.68-3.61 (m, 1H), 3.46-3.39 (m, 2H), 2.35 (s, 3H), 1.43-1.31 (m, 2H), 1.02 (s, 2H). Analytical HPLC retention time: 1.11 min (Method B).

Example 10. 3-[1-(3,4-dichlorophenyl)cyclopropyl]-1-[(3S,4R)-4-(2,6-difluoro-4-methoxyphenyl)-1-(2-hydroxyethyl)-2-oxopyrrolidin-3-yl]urea

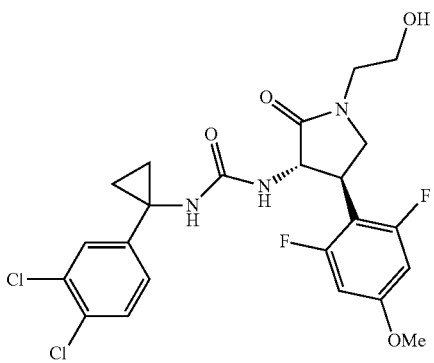 [SMILES: COc1cc(F)c([C@@H]2CN(CCO)C(=O)[C@H]2NC(=O)NC2(c3ccc(Cl)c(Cl)c3)CC2)c(F)c1]

10A. (3S,4R)-4-(2,6-difluoro-4-methoxyphenyl)-3-(2,5-dimethyl-1H-pyrrol-1-yl)pyrrolidin-2-one

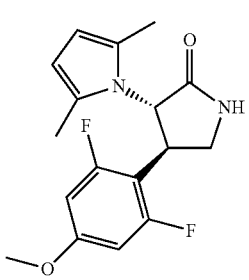 [SMILES: COc1cc(F)c([C@@H]2CNC(=O)[C@H]2n2c(C)ccc2C)c(F)c1]

Intermediate 3 (0.300 g, 1.24 mmol) was dissolved in MeOH (8.0 mL), and the solution was stirred at rt under nitrogen while 2,5-hexanedione (0.146 mL, 1.24 mmol) and acetic acid (0.071 mL, 1.2 mmol) were added dropwise. The resulting reaction mixture was then heated at 50° C. with stirring ON. The reaction solution was evaporated to remove MeOH. 1M NaOH was added to the residue, and the mixture was extracted with DCM (3×). The combined extracts were washed with brine, dried over Na$_2$SO$_4$, filtered and evaporated. The residue was purified by flash chromatography to provide 10A as a white foam. (0.318 g, 80%). MS (ESI) m/z 321.5 (M+H).

10B. (3S,4R)-1-(2-((tert-butyldimethylsilyl)oxy)ethyl)-4-(2,6-difluoro-4-methoxyphenyl)-3-(2,5-dimethyl-1H-pyrrol-1-yl)pyrrolidin-2-one

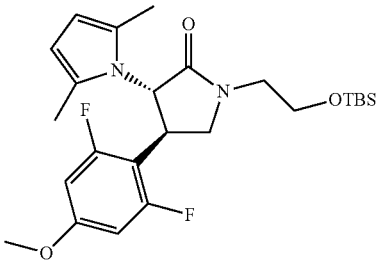 [SMILES: COc1cc(F)c([C@@H]2CN(CCO[Si](C)(C)C(C)(C)C)C(=O)[C@H]2n2c(C)ccc2C)c(F)c1]

10A (0.100 g, 0.312 mmol) was dissolved in DMF (1.1 mL) and added dropwise to a suspension of NaH, (60% in oil, 14.0 mg, 0.343 mmol) in DMF (0.5 mL) at 0° C. The mixture was stirred for 10 min at rt, then recooled to 0-5° C. (2-bromoethoxy)(tert-butyl)dimethylsilane (80.0 µL, 0.375 mmol) was added dropwise, and stirring was continued for 30 min at 0-5° C., then for 3 days at rt. The reaction mixture was diluted with water and extracted with EtOAc (3×). The combined extracts were washed with water (2×) and brine, then dried over Na$_2$SO$_4$, filtered and evaporated. The residue was purified by flash chromatography to provide 10B (0.129 g, 86% yield) as a colorless oil. MS (ESI) m/z 479.7 (M+H).

10C. (3S,4R)-3-amino-1-(2-((tert-butyldimethylsilyl)oxy)ethyl)-4-(2,6-difluoro-4-methoxyphenyl)pyrrolidin-2-one

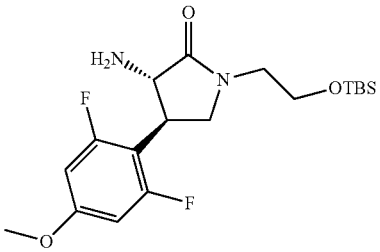 [SMILES: COc1cc(F)c([C@@H]2CN(CCO[Si](C)(C)C(C)(C)C)C(=O)[C@H]2N)c(F)c1]

A mixture of 10B (0.123 g, 0.257 mmol), hydroxylamine hydrochloride (0.179 g, 2.57 mmol) and TEA (0.179 mL, 1.29 mmol) in ethanol (2.0 mL) and water (0.2 mL) was stirred and heated at 78° C. ON. Additional hydroxylamine hydrochloride (0.179 g, 2.57 mmol) and TEA (0.179 mL, 1.29 mmol) were added, and the reaction mixture was again heated ON at 78-80° C. The reaction mixture was diluted with water and EtOAc, and phases were separated. The aqueous layer was extracted with EtOAc (2×), and the combined extracts were washed with brine, dried over Na$_2$SO$_4$, filtered, evaporated and dried in vacuo to provide 10C (94 mg, 91% yield) which was used without further purification. MS (ESI) m/z 401.6 (M+H).

Example 10. 10C (20.0 mg, 0.050 mmol) was dissolved in DCM (0.2 mL) and CDI (8.9 mg, 0.055 mmol) was added. The mixture was stirred at rt for 5-10 min, then a solution of 1-(3,4-dichlorophenyl)cyclopropanamine (12 mg, 0.060 mmol, prepared from 3,4-dichlorobenzonitrile according to general procedure 1) in DCM (0.2 mL) was added. The reaction mixture was stirred for 3 days at rt, then evaporated.

The crude urea product (31 mg, 0.050 mmol) was taken up in 1M TBAF in THF (0.20 mL, 0.20 mmol), and the mixture stirred at rt ON. The reaction mixture was diluted with EtOAc and washed with water and brine, then dried over Na$_2$SO$_4$, filtered and evaporated. The residue was purified by RP-HPLC to provide the title compound (2.6 mg, 10%). MS (ESI) m/z: 514.4 (M+H). $^1$H NMR (500 MHz, DMSO-d$_6$) δ ppm 1.06-1.22 (m, 4H) 2.86-2.96 (m, 1H) 3.17-3.27 (m, 2H) 3.33-3.43 (m, 2H) 3.52 (br d, J=14.65 Hz, 2H) 3.75 (s, 3H) 3.79-3.93 (m, 1H) 4.51 (br t, J=9.46 Hz, 1H) 6.33 (br d, J=8.54 Hz, 1H) 6.69 (br d, J=10.68 Hz, 2H) 6.94 (br d, J=7.93 Hz, 1H) 6.99 (s, 1H) 7.22 (s, 1H) 7.40 (br d, J=8.24 Hz, 1H). HPLC retention time: 1.50 min (Method A).

Example 83. 3-[1-(6-chloro-1,3-benzoxazol-2-yl)cyclopropyl]-1-1(3S,4R)-4-(4-chloro-2,6-difluorophenyl)-2-oxopyrrolidin-3-yl]urea

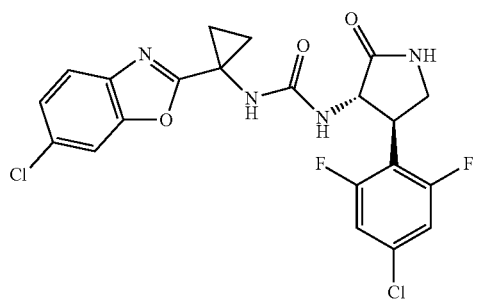 [SMILES: O=C(N[C@@H]1C(=O)NC[C@H]1c1c(F)cc(Cl)cc1F)NC1(c2nc3ccc(Cl)cc3o2)CC1]

83A. Methyl (3S,4R)-4-(4-chloro-2,6-difluorophenyl)-2-oxopyrrolidine-3-carboxylate

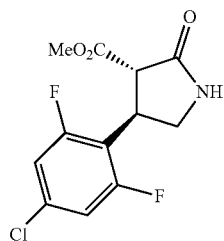 [SMILES: COC(=O)[C@@H]1C(=O)NC[C@H]1c1c(F)cc(Cl)cc1F]

Dimethyl (R)-2-(1-(4-chloro-2,6-difluorophenyl)-2-nitroethyl)malonate (0.643 g, 1.83 mmol, prepared from 4-chloro-2,6-difluorobenzaldehyde as described for Intermediate 1, Steps A and B) was dissolved in MeOH (25 mL), and the solution was cooled to 0° C. with stirring under nitrogen. Nickel(II) chloride hexahydrate (0.348 g, 1.46 mmol) was added, followed by portionwise addition of NaBH$_4$ (0.277 g, 7.31 mmol). Once the addition was complete, the cooling bath was removed, and the reaction mixture was stirred at room temperature for 1.5 h. The reaction mixture was filtered through a Celite pad, and solids washed with MeOH. The filtrate was evaporated. The residue was partitioned between EtOAc and sat'd NH$_4$Cl, and the phases were separated. The organic layer was washed with additional sat'd NH4Cl and brine, then dried over Na$_2$SO$_4$, filtered and evaporated. The residue was purified by flash chromatography to provide 83A (0.386 g, 73% yield) as a white crystalline solid. MS (ESI) m/z 290.0 (M+H).

83B. (3S,4R)-4-(4-chloro-2,6-difluorophenyl)-2-oxopyrrolidine-3-carboxylic Acid

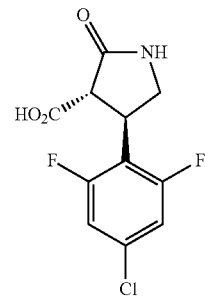

83B (0.347 g, 1.259 mmol, 96% yield) was prepared from 84A following the procedure described for Intermediate 1 MS (ESI) m/z 276.0 (M+H).

Example 83. TEA (0.013 mL, 0.091 mmol) and diphenylphosphoryl azide (0.018 mL, 0.084 mmol) were added to 83B (0.021 g, 0.076 mmol) in toluene (0.7 mL), and the mixture was stirred at room temperature under nitrogen for 1 h, then heated at 90° C. for 1 hr. The reaction mixture was cooled to room temperature, and 1-(6-chlorobenzo[d]oxazol-2-yl)cyclopropan-1-amine, HCl (20.5 mg, 0.0840 mmol, prepared from 2-amino-5-chlorophenol using the procedure described for 5C) was added, followed immediately by TEA (0.013 mL, 0.091 mmol) in ~0.5 mL toluene. The reaction mixture was then heated for 3h at 120° C. The reaction mixture was cooled to rt, diluted with water and extracted 3× with EtOAc. The combined extracts were washed with brine and dried over Na$_2$SO$_4$, filtered and evaporated. Residue purified by RP-HPLC to provide the title compound (11 mg, 29% yield). 1H NMR (500 MHz, DMSO-d$_6$) δ ppm 8.02 (s, 1H) 7.72 (s, 1H) 7.60 (d, J=8.24 Hz, 1H) 7.34-7.41 (m, 1H) 7.29 (br d, J=8.54 Hz, 2H) 7.24 (s, 1H) 6.54 (br d, J=7.93 Hz, 1H) 4.48 (br t, J=9.31 Hz, 1 H) 3.73-3.85 (m, 1H) 3.29 (br t, J=9.46 Hz, 1H) 1.52 (br s, 3H) 1.16-1.32 (m, 2H). MS (ESI) m/z: 481.0 (M+H). Analytical HPLC retention time: 1.58 min (Method C).

Example 94. 1-((3S,4R)-1-(cyclopropylmethyl)-4-(2,6-difluoro-4-methoxyphenyl)-2-oxopyrrolidin-3-yl)-3-(1-(6-methylpyridin-2-yl)cyclopropyl)urea

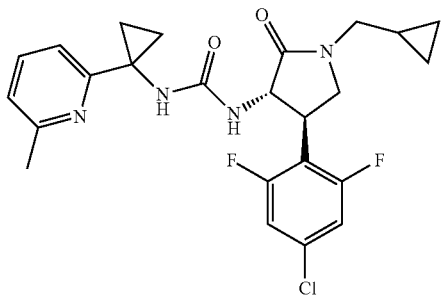 [SMILES: Cc1cccc(C2(NC(=O)N[C@@H]3C(=O)N(CC4CC4)C[C@H]3c3c(F)cc(Cl)cc3F)CC2)n1]

94A. tert-butyl (cyclopropylmethyl)((3S,4R)-1-(cyclopropylmethyl)-4-(2,6-difluoro-4-methoxyphenyl)-2-oxopyrrolidin-3-yl)carbamate

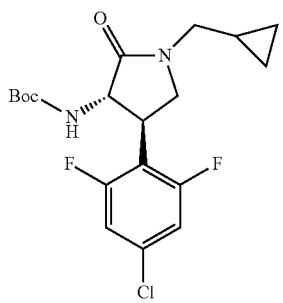 [SMILES: CC(C)(C)OC(=O)N[C@@H]1C(=O)N(CC2CC2)C[C@H]1c1c(F)cc(Cl)cc1F]

Intermediate 4 (100 mg, 0.292 mmol) was dissolved in DMF (2 ml), and NaH, 60% in oil (12.8 mg, 0.321 mmol) was added at 0-5° C. The mixture was stirred for 10 min at room temperature, then recooled to 0-5° C. (Bromomethyl)-cyclopropane was added dropwise, and stirring was continued for 30 min in ice bath, then at rt ON. The reaction mixture was diluted with EtOAc and washed with 10% LiCl. The aq. layer was reextracted with EtOAc, and the combined extracts were washed with brine, then dried over anhydrous sodium sulfate, filtered and evaporated. The residue was purified by flash chromatography to provide 94A. (77.6 mg, 67.0%) MS (ESI) m/z 397.3 (M+H).

94B. (3S,4R)-3-amino-1-(cyclopropylmethyl)-4-(2,6-difluoro-4-methoxyphenyl)pyrrolidin-2-one, TFA

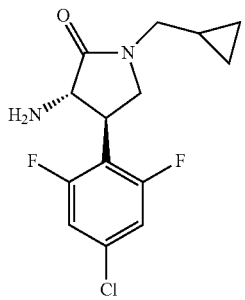 [SMILES: N[C@@H]1C(=O)N(CC2CC2)C[C@H]1c1c(F)cc(Cl)cc1F]

94A (77 mg, 0.19 mmol) was dissolved in a mixture of DCM (0.97 mL) and TFA (75 µl, 0.97 mmol), and the reaction mixture was stirred ON at rt. The reaction mixture was concentrated, and the resulting solid dried under vacuum to provide 94B (58 mg, 75%). MS (ESI) m/z 297.2 (M+H).

Example 94. 94B (28 mg, 0.094 mmol) and TEA (0.013 mL, 0.094 mmol) were dissolved in THF (0.5 mL), and 4-nitrophenyl chloroformate (19.0 mg, 0.094 mmol) was added. The mixture was stirred at room temperature for 30 min, then 1-(6-methylpyridin-2-yl)cyclopropan-1-amine (14.0 mg, 0.094 mmol) and TEA (0.026 mL, 0.189 mmol) were added. The reaction mixture was heated at 50° C. ON. The reaction mixture was diluted with EtOAc, washed with brine, dried over $Na_2SO_4$ and evaporated to give the crude which was purified by RP chromatography to provide the title compound (25 mg, 56% yield). MS (ESI) m/z 471.3 (M+H). $^1$H NMR (500 MHz, DMSO-$d_6$) δ 7.30 (t, J=7.8 Hz, 1H), 6.84 (d, J=7.0 Hz, 1H), 6.77 (d, J=7.6 Hz, 1H), 6.72 (s, 1H), 6.56 (d, J=11.0 Hz, 2H), 6.21 (d, J=8.5 Hz, 1H), 4.34 (t, J=9.5 Hz, 1H), 3.64-3.50 (m, 4H), 3.40 (t, J=9.0 Hz, 1H), 3.36-3.19 (m, 1H), 3.07 (dd, J=13.9, 6.9 Hz, 1H), 2.83-2.73 (m, 1H), 2.16 (s, 3H), 1.27-1.05 (m, 2H), 0.90-0.78 (m, 2H), 0.76-0.66 (m, 1H), 0.33-0.22 (m, 2H), 0.02 (dd, J=11.3, 4.6 Hz, 2H). Analytical HPLC retention time: 2.14 min (Method D).

Example 128. 1-[(3S,4R)-4-(2,6-difluoro-4-methoxyphenyl)-2-oxopyrrolidin-3-yl]-3-(1-{3-[(1,2,3,4-tetrahydronaphthalen-2-yl)methoxy]phenyl}cyclopropyl)-urea

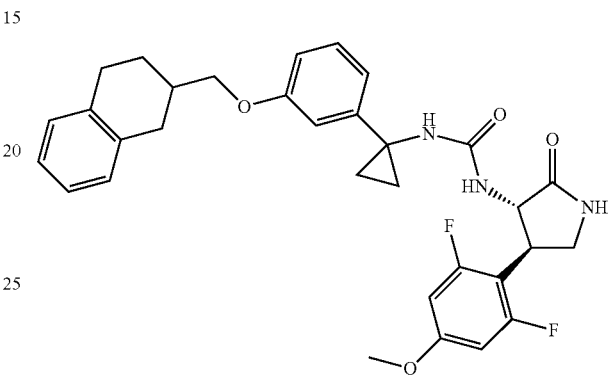

128A. 3-((1,2,3,4-tetrahydronaphthalen-2-yl)methoxy)benzonitrile

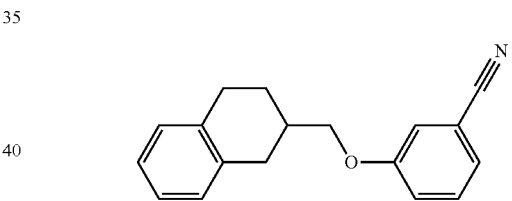

3-hydroxybenzonitrile (0.100 g, 0.839 mmol) and (1,2,3,4-tetrahydronaphthalen-2-yl)methanol (0.204 g, 1.26 mmol) were dissolved in THF (4.20 ml) under nitrogen. The mixture was stirred at room temperature, and triphenylphosphine (0.440 g, 1.68 mmol) was added, followed by dropwise addition of DIAD (0.326 ml, 1.68 mmol). Stirring was continued overnight at room temperature. The reaction mixture was concentrated, and residue was purified by flash chromatography to provide 128A (0.170 g, 77%). MS (ESI) m/z 264.0 (M+H).

Example 128. Nitrile 128A was converted into the cyclopropyl amine using the general procedure described above, and the amine was condensed with Intermediate 2 as described for Example 1. Purification by RP HPLC followed by chiral SFC (Chiralpak AD column eluted with 65% $CO_2$/35% IPA with 0.1% DEA) provided the title compound as the first eluting diastereomer. MS (ESI) m/z: 562.3 (M+H). $^1$H NMR (500 MHz, DMSO-$d_6$) δ 7.76 (br s, 1H), 7.12-7.07 (m, 2H), 7.07 (s, 3H), 6.74 (s, 1H), 6.72-6.67 (m, 2H), 6.66-6.56 (m, 3H), 6.11 (d, J=8.2 Hz, 1H), 4.42 (t, J=9.4 Hz, 1H), 3.90 (br d, J=6.2 Hz, 2H), 3.76 (br d, J=9.9 Hz, 1H), 3.72 (s, 3H), 3.28 (t, J=9.4 Hz, 1H), 2.93-2.86 (m, J=16.5, 4.7 Hz, 1H), 2.81-2.74 (m, 2H), 2.60-2.55 (m, 1H), 2.16 (br d, J=4.7 Hz, 1H), 2.02 (br d, J=14.2 Hz, 1H), 1.57-1.40 (m, 1H), 1.16-1.00 (m, 4H). One proton on the lactam not obscured by water suppression. Analytical HPLC retention time: 2.15 min (Method C).

Example 130. 1-[(3S,4R)-4-(2,6-difluoro-4-methoxyphenyl)-2-oxopyrrolidin-3-yl]-3-(1-{6-[(naphthalen-2-yl)methoxy]pyridin-2-yl}cyclopropyl)urea

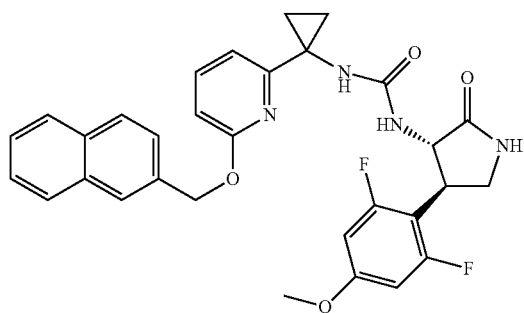 [SMILES: COc1cc(F)c([C@@H]2CNC(=O)[C@H]2NC(=O)NC2(c3cccc(OCc4ccc5ccccc5c4)n3)CC2)c(F)c1]

130 A. 6-(naphthalen-2-ylmethoxy)picolinonitrile

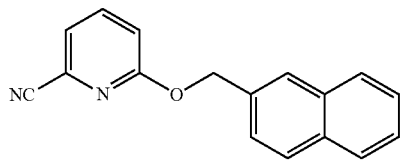 [SMILES: N#Cc1cccc(OCc2ccc3ccccc3c2)n1]

Naphthalen-2-ylmethanol (0.23 g, 1.4 mmol) was dissolved in THF (4.0 mL), and NaH, 60% in oil (0.032 g, 0.79 mmol) was added. After stirring at room temperature for 10-15 min, the solution was cooled to 0° C., and a solution of 6-chloropicolinonitrile (0.10 g, 0.72 mmol) in THF (3.0 mL) was added dropwise via syringe. The reaction mixture was heated overnight at 66° C. The reaction mixture was partitioned between EtOAc and water. The aqueous layer was reextracted with EtOAc, and combined organic layers were washed with brine, dried over $Na_2SO_4$, filtered and evaporated. The residue was purified by flash chromatography to provide 130A as a white solid (78 mg, 41.5%). MS (ESI) m/z 283.0 (M+Na).

Example 130. 130A was converted into the corresponding cyclopropylamine using the general procedure outlined above. The resulting amine was condensed with Intermediate 2 as described for Example 1 to provide the title compound. MS (ESI) m/z: 559.4 (M+H). $^1$H NMR (500 MHz, DMSO-d6) δ 7.96-7.82 (m, 5H), 7.50 (br t, J=7.2 Hz, 4H), 6.85 (s, 1H), 6.80-6.73 (m, 1H), 6.71 (br d, J=11.0 Hz, 2H), 6.60 (br d, J=7.9 Hz, 1H), 6.32 (br d, J=8.2 Hz, 1H), 5.39 (s, 2H), 4.44 (t, J=9.2 Hz, 1H), 3.73 (s, 3H), 3.45-3.34 (m, 1H), 3.29 (t, J=9.5 Hz, 1H), 1.42-1.28 (m, 2H), 1.06-0.91 (m, 2H). One proton not observed due to water suppression. HPLC retention time: 2.15 min (Method C).

Additional examples of compounds shown in Table 2 below were prepared using combinations of the procedures described in the above schemes and examples or modifications thereof known to one skilled in the art of organic synthesis.

TABLE 2

| Ex. No. | Structure[b] | Name | Obs (M + H) | RT (min)[a] |
|---|---|---|---|---|
| 11 | | 3-[1-(4-chlorophenyl)cyclopropyl]-1-[(3S,4R)-4-(2,6-difluoro-4-methoxyphenyl)-2-oxopyrrolidin-3-yl]urea | 436.1 | 1.51(D) |
| 12 | | 1-[(3S,4R)-4-(2,6-difluoro-4-methoxyphenyl)-2-oxopyrrolidin-3-yl]-3-[1-(3-methoxyphenyl)cyclopropyl]urea | 432.2 | 1.46(D) |

TABLE 2-continued

| Ex. No. | Name | Obs (M + H) | RT (min)[a] |
|---|---|---|---|
| 13 | 1-[(3S,4R)-4-(2,6-difluoro-4-methoxyphenyl)-2-oxopyrrolidin-3-yl]-3-[1-(3-fluorophenyl)cyclopropyl]urea | 420.3 | 1.41(D) |
| 14 | 1-[(3S,4R)-4-(2,6-difluoro-4-methoxyphenyl)-2-oxopyrrolidin-3-yl]-3-[1-(4-fluorophenyl)cyclopropyl]urea | 420.3 | 1.49(D) |
| 15 | 1-[(3S,4R)-4-(2,6-difluoro-4-methoxyphenyl)-2-oxopyrrolidin-3-yl]-3-[1-(2-fluorophenyl)cyclopropyl]urea | 420.2 | 1.4 (D) |
| 16 | 1-[(3S,4R)-4-(2,6-difluoro-4-methoxyphenyl)-2-oxopyrrolidin-3-yl]-3-[1-(pyridin-2-yl)cyclopropyl]urea | 403.2 | 0.81(D) |
| 17 | 1-[(3S,4R)-4-(2,6-difluoro-4-methoxyphenyl)-2-oxopyrrolidin-3-yl]-3-[1-(6-methylpyridin-2-yl)cyclopropyl]urea | 417.1 | 1.38(D) |

TABLE 2-continued

| Ex. No. | Structure[b] | Name | Obs (M + H) | RT (min)[a] |
|---|---|---|---|---|
| 18 | | 3-[1-(4-cyanophenyl)cyclopropyl]-1-[(3S,4R)-4-(2,6-difluoro-4-methoxyphenyl)-2-oxopyrrolidin-3-yl]urea | 427.3 | 1.22(C) |
| 19 | | 1-[(3S,4R)-4-(2,6-difluoro-4-methoxyphenyl)-2-oxopyrrolidin-3-yl]-3-{1-[3-(trifluoromethyl)phenyl]cyclopropyl}urea | 470.3 | 1.56(C) |
| 20 | | 1-[(3S,4R)-4-(2,6-difluoro-4-methoxyphenyl)-2-oxopyrrolidin-3-vl]-3-[1-(3-methylphenyl)cyclopropyl]urea | 416 | 1.45(D) |
| 21 | | 1-[(3S,4R)-4-(2,6-difluoro-4-methoxyphenyl)-2-oxopyrrolidin-3-yl]-3-[1-(4-methylpyridin-2-yl)cyclopropyl]urea | 417 | 1.41(D) |
| 22 | | 1-[(3S,4R)-4-(2,6-difluoro-4-methoxyphenyl)-2-oxopyrrolidin-3-yl]-3-[1-(4-methoxyphenyl)cyclopropyl]urea | 431.9 | 1.37(D) |

TABLE 2-continued

| Ex. No. | Structure | Name | Obs (M + H) | RT (min) |
|---|---|---|---|---|
| 23 | | 1-[(3S,4R)-4-(2,6-difluoro-4-methoxyphenyl)-2-oxopyrrolidin-3-yl]-3-{1-[5-(trifluoromethyl)pyridin-2-yl]cyclopropyl}urea | 471.2 | 1.5 (D) |
| 24 | | 3-[1-(3-chloro-phenyl)cyclopropyl]-1-[(3S,4R)-4-(2,6-difluoro-4-methoxyphenyl)-2-oxopyrrolidin-3-yl]urea | 436.2 | 1.48(D) |
| 25 | | 1-[(3S,4R)-4-(2,6-difluoro-4-methoxyphenyl)-2-oxopyrrolidin-3-yl]-3-[1-(6-fluoropyridin-2-yl)cyclopropyl]urea | 421.2 | 1.24(D) |
| 26 | | 1-[(3S,4R)-4-(2,6-difluoro-4-methoxyphenyl)-2-oxopyrrolidin-3-yl]-3-[1-(quinolin-2-yl)cyclopropyl]urea | 453.2 | 0.99(C) |
| 27 | | 3-[1-(3,5-dichloro-phenyl)cyclopropyl]-1-[(3S,4R)-4-(2,6-difluoro-4-methoxyphenyl)-2-oxopyrrolidin-3-yl]urea | 470.3 | 1.65(C) |

TABLE 2-continued

| Ex. No. | Structure[b] | Name | Obs (M + H) | RT (min)[a] |
|---|---|---|---|---|
| 28 | | 1-[(3S,4R)-4-(2,6-difluoro-4-methoxyphenyl)-2-oxopyrrolidin-3-yl]-3-[1-(4,6-dimethylpyrimidin-2-yl)cyclopropyl]urea | 431.9 | 1.01(C) |
| 29 | | 1-[(3S,4R)-4-(2,6-difluoro-4-methoxyphenyl)-2-oxopyrrolidin-3-yl]-3-[1-(isoquinolin-3-yl)cyclopropyl]urea | 453.1 | 1.02(C) |
| 30 | | 1-[(3S,4R)-4-(2,6-difluoro-4-methoxyphenyl)-2-oxopyrrolidin-3-yl]-3-[1-(4,6-dimethylpyridin-2-yl)cyclopropyl]urea | 430.9 | 1.36(D) |
| 31 | | 3-[1-(6-cyanopyridin-2-yl)cyclopropyl]-1-[(3S,4R)-4-(2,6-difluoro-4-methoxyphenyl)-2-oxopyrrolidin-3-yl]urea | 428.2 | 1.34(C) |
| 32 | | 1-[(3S,4R)-4-(2,6-difluoro-4-methoxyphenyl)-2-oxopyrrolidin-3-yl]-3-[1-(pyridazin-3-yl)cyclopropyl]urea | 404.2 | 0.86(D) |

TABLE 2-continued

| Ex. No. | Structure[b] | Name | Obs (M + H) | RT (min)[a] |
|---|---|---|---|---|
| 33 | | 1-[(3S,4R)-4-(2,6-difluoro-4-methoxyphenyl)-1-methyl-2-oxopyrrolidin-3-yl]-3-[1-(6-methylpyridin-2-yl)cyclopropyl]urea | 431.4 | 0.97(C) |
| 34 | | 1-[(3S,4R)-4-(2,6-difluoro-4-methoxyphenyl)-2-oxopyrrolidin-3-yl]-3-[1-(5-methylpyridin-2-yl)cyclopropyl)urea | 417.3 | 0.86(C) |
| 35 | | 1-[(3S,4R)-4-(2,6-difluoro-4-methoxyphenyl)-2-oxopyrrolidin-3-yl]-3-[1-(6-methoxy-1,3-benzothiazol-2-yl)cyclopropyl]urea | 489.4 | 1.33(C) |
| 36 | | 1-[(3S,4R)-4-(2,6-difluoro-4-methoxyphenyl)-2-oxopyrrolidin-3-yl]-3-{1-[3-fluoro-5-(trifluoromethyl)phenyl]cyclopropyl}urea | 489.1 | 1.68(D) |
| 37 | | 1-(1-(3-(2-(benzyloxy)ethoxy)phenyl)cyclopropyl)-3-((3S,4R)-4-(2,6-difluoro-4-methoxyphenyl)-2-oxopyrrolidin-3-yl)urea | 552.3 | 1.78(C) |

TABLE 2-continued

| Ex. No. | Structure[b] | Name | Obs (M + H) | RT (min)[a] |
|---|---|---|---|---|
| 38 | | 3-{1-[3,5-bis(trifluoromethyl)phenyl]cyclopropyl}-1-[(3S,4R)-4-(2,6-difluoro-4-methoxyphenyl)-2-oxopyrrolidin-3-yl]urea | 537.8 | 1.87(D) |
| 39 | | 1-[(3S,4R)-4-(2,6-difluoro-4-methoxyphenyl)-2-oxopyrrolidin-3-yl]-3-{1-[3-(trifluoromethoxy)phenyl]cyclopropyl}urea | 486.3 | 1.62(D) |
| 40 | | 3-[1-(4-chloro-3-metliylphenyl)cyclopropyl]-1-[(3S,4R)-4-(2,6-difluoro-4-methoxyphenyl)-2-oxopyrrolidin-3-yl]urea | 450.3 | 1.6 (D) |
| 41 | | 3-[1-(6-chloro-4-methylpyridin-2-yl)cyclopropyl]-1-[(3S,4R)-4-(2,6-difluoro-4-methoxyphenyl)-2-oxopyrrolidin-3-yl]urea | 451.2 | 1.45(D) |
| 42 | | 3-[1-(3,4-dichlorophenyl)cyclopropyl]-1-[(3S,4R)-4-(2,6-difluoro-4-methoxyphenyl)-2-oxopyrrolidin-3-yl]urea | 470.2 | 155 (D) |

TABLE 2-continued

| Ex. No. | Structure | Name | Obs (M + H) | RT (min) |
|---|---|---|---|---|
| 43 | | 1-[(3S,4R)-4-(2,6-difluoro-4-methoxyphenyl)-2-oxopyrrolidin-3-yl]-3-[1-(1,7-naphthyridin-2-yl)cyclopropyl]urea | 453.9 | 1.1 (D) |
| 44 | | 1-[(3S,4R)-4-(2,6-difluoro-4-methoxyphenyl)-2-oxopyrrolidin-3-yl]-3-[1-(6-methylpyrazin-2-yl)cyclopropyl]urea | 418.3 | 1.1 (C) |
| 45 | | 1-[(3S,4R)-4-(2,6-difluoro-4-methoxyphenyl)-2-oxopyrrolidin-3-yl]-3-(1-{1-methyl-1H-pyrrolo[3,2-b]pyridin-5-yl}cyclopropyl)urea | 456.4 | 1.13(D) |
| 46 | | 3-{1-[4-chloro-3-(trifluoromethoxy)phenyl]cyclopropyl}-1-[(3S,4R)-4-(2,6-difluoro-4-methoxyphenyl)-2-oxopyrrolidin-3-yl]urea | 540.3 | 1.77(D) |
| 47 | | 3-[1-(5-chloro-6-methylpyridin-2-yl)cyclopropyl]-1-[(3S,4R)-4-(2,6-difluoro-4-methoxyphenyl)-2-oxopyrrolidin-3-yl]urea | 451.2 | 1.47(D) |

TABLE 2-continued

| Ex. No. | Structure | Name | Obs (M + H) | RT (min) |
|---|---|---|---|---|
| 48 | | 3-[1-(6-chloropyridin-2-yl)cyclopropyl]-1-[(3S,4R)-4-(2-fluoro-4-methoxyphenyl)-2-oxopyrrolidin-3-yl]urea | 419 | (Method) |
| 49 | | 3-[1-(1-benzothiophen-5-yl)cyclopropyl]-1-[(3S,4R)-4-(2,6-difluoro-4-methoxyphenyl)-2-oxopyrrolidin-3-yl]urea | 457.9 | 1.55(D) |
| 50 | | 3-[1-(3-chloro-4-methylphenyl)cyclopropyl]-1-[(3S,4R)-4-(2,6-difluoro-4-methoxyphenyl)-2-oxopyrrolidin-3-yl]urea | 449.8 | 1.64(D) |
| 51 | | 3-[1-(2,2-difluoro-2H-1,3-benzodioxol-5-yl)cyclopropyl]-1-[(3S,4R)-4-(2,6-difluoro-4-methoxyphenyl)-2-oxopyrrolidin-3-yl]urea | 482.1 | 1.62(D) |
| 52 | | 3-[1-(2,4-dichloro-phenyl)cyclopropyl]-1-[(3S,4R)-4-(2,6-difluoro-4-methoxyphenyl)-2-oxopyrrolidin-3-yl]urea | 470.1 | 1.67(D) |

TABLE 2-continued

| Ex. No. | Structure | Name | Obs (M + H) | RT (min) |
|---|---|---|---|---|
| 53 | | 3-[1-(6-chloroquinolin-2-yl)cyclopropyl]-1-[(3S,4R)-4-(2,6-difluoro-4-methoxyphenyl)-2-oxopyrrolidin-3-yl]urea | 487.4 | 1.46(C) |
| 54 | | 3-11-(2-chloropyridin-4-yl)cyclopropyl-1-[(3S,4R)-4-(2,6-difluoro-4-methoxyphenyl)-2-oxopyrrolidin-3-yl]urea | 437 | 1.33(D) |
| 55 | | 3-[1-(6-chloro-1,3-benzoxazol-2-yl)cyclopropyl]-1-[(3S,4R)-4-(2,6-difluoro-4-methoxyphenyl)-2-oxopyrrolidin-3-yl]urea | 477.3 | 1.53(C) |
| 56 | | 3-[1-(1,3-benzothiazol-2-yl)cyclopropyl]-1-[(3S,4R)-4-(2,6-difluoro-4-methoxyphenyl)-2-oxopyrrolidin-3-yl]urea | 459.2 | 1.37(C) |
| 57 | | 1-[(3S,4R)-4-(2,6-difluoro-4-methoxyphenyl)-2-oxopyrrolidin-3-yl]-3-(1-{1-methyl-1H-pyrrolo[2,3-b]pyridin-3-yl}cyclopropyl)urea | 456.2 | 1.14(D) |

TABLE 2-continued

| Ex. No. | Structure[b] | Name | Obs (M + H) | RT (min)[a] |
|---|---|---|---|---|
| 58 | | 1-[(3S,4R)-4-(2,6-difluoro-4-methoxyphenyl)-2-oxopyrrolidin-3-yl]-3-[1-(1-methyl-1 H-indazol-6-yl)cyclopropyl]urea | 455.9 | 1.19(D) |
| 59 | | 3-[1-(5-chloro-1,3-benzoxazol-2-\l)cyclopropyll-1-[(3S,4R)-4-(2,6-difluoro-4-methoxyphenyl)-2-oxopyrrolidin-3-yl]urea | 477.1 | 1.47(D) |
| 60 | | 1-[(3S,4R)-4-(2,6-difluoro-4-methoxyphenyl)-2-oxopyrrolidin-3-yl]-3-[1-(naphthalen-2-yl)cyclopropyl]urea | 452.1 | 1.6 (D) |
| 61 | | 1-[(3S,4R)-4-(2,6-difluoro-4-methoxyphenyl)-2-oxopyrrolidin-3-yl]-3-[1-(5-phenyl-1,3-thiazol-2-yl)cyclopropyl]urea | 484.9 | 1.48(D) |
| 62 | | 3-{1-[3-chloro-4-(trifluoromethyl)phenyl]cyclopropyl}-1-[(3S,4R)-4-(2,6-difluoro-4-methoxyphenyl)-2-oxopyrrolidin-3-yl]urea | 503.8 | 1.71(D) |

TABLE 2-continued

| Ex. No. | Name | Obs (M + H) | RT (min)$^a$ |
|---|---|---|---|
| 63 | 1-[(3S,4R)-4-(2,6-difluoro-4-methoxyphenyl)-2-oxopyrrolidin-3-yl]-3-[1-(6-methoxynaphthalen-2-yl)cyclopropyl]urea | 482.1 | 1.54(D) |
| 64 | 3-[1-(1,3-benzothiazol-6-yl)cyclopropyl]-1-[(3S,4R)-4-(2,6-difluoro-4-methoxyphenyl)-2-oxopyrrolidin-3-yl]urea | 458.9 | 1.16(D) |
| 65 | 3-[1-(1,3-benzothiazol-5-yl)cyclopropyl]-1-[(3S,4R)-4-(2,6-difluoro-4-methoxyphenyl)-2-oxopyrrolidin-3-yl]urea | 459 | 1.21(D) |
| 66 | 1-[(3S,4R)-4-(2,6-difluoro-4-methoxyphenyl)-2-oxopyrrolidin-3-yl]-3-{1-[3-methyl-5-(trifluoromethyl)phenyl]cyclopropyl}urea | 484.1 | 1.69(D) |
| 67 | 1-[(3S,4R)-4-(2,6-difluoro-4-methoxyphenyl)-1-(2-hydroxyethyl)-2-oxopyrrolidin-3-yl]-3-[1-(quinolin-2-yl)cyclopropyl]urea | 497.4 | 4.60(D) |

TABLE 2-continued

| Ex. No. | Structure[b] | Name | Obs (M + H) | RT (min)[a] |
|---|---|---|---|---|
| 68 | | 3-[1-(3-chloro-4-fluorophenyl)cyclopropyl]-1-[(3S,4R)-4-(2,6-difluoro-4-methoxyphenyl)-2-oxopyrrolidm-3-yl]urea | 454.1 | 1.67(C) |
| 69 | | 1-[(3S,4R)-4-(2,6-difluoro-4-methoxyphenyl)-2-oxopyrrolidin-3-yl]-3-]1-(2-methyl-1,3-thiazol-4-yl)cyclopropyl]urea | 423.0 | 1.13(D) |
| 70 | | 1-[(3S,4R)-4-(2,6-difluoro-4-methoxyphenyl)-2-oxopyrrolidin-3-yl]-3-[1-(4-methyl-1,3-thiazol-2-yl)cyclopropyl]urea | 423.1 | 1.12(D) |
| 71 | | 1-[(3S,4R)-4-(2,6-difluoro-4-methoxyphenyl)-2-oxopyrrolidin-3-yl]-3-[1-(2,2-dimethyl-2H-chromen-6-yl)cyclopropyl]urea | 483.9 | 1.67(D) |
| 72 | | 1-[(3S,4R)-4-(2,6-difluoro-4-methoxyphenyl)-2-oxopyrrolidin-3-yl]-3-{1-[5-(trifluoromethoxy)-1,3-benzoxazol-2-yl]cyclopropyl}urea | 527.1 | 1.61(D) |

TABLE 2-continued

| Ex. No. | Structure[b] | Name | Obs (M + H) | RT (min)[a] |
|---|---|---|---|---|
| 73 | | 1-[(3S,4R)-4-(2,6-difluoro-4-methoxyphenyl)-2-oxopyrrolidin-3-yl]-3-{1-[3-methyl-5-(trifluoromethoxy)phenyl]cyclopropyl}urea | 500.1 | 1.77(D) |
| 74 | | 3-{1-[3-chloro-5-(trifluoromethoxy)phenyl]cyclopropyl}-1-[(3S,4R)-4-(2,6-difluoro-4-methoxyphenyl)-2-oxopyrrolidin-3-yl]urea | 519.9 | 1.82(D) |
| 75 | | -[(3S,4R)-4-(2,6-difluoro-4-methoxyphenyl)-2-oxopyrrolidin-3-yl]-3-{1-[6-(trifluoromethyl)-1,3-benzoxazol-2-yl]cyclopropyl}urea | 511.1 | 1.57(D) |
| 76 | | 1-[(3S,4R)-4-(2,6-difluoro-4-methoxyphenyl)-2-oxopyrrolidin-3-yl]-3-[1-(6-methyl-1,3-benzoxazol-2-yl)cyclopropyl]urea | 457.1 | 1.40(D) |
| 77 | | 1-(1-(6-chloropyridin-2-yl)cyclopropyl)-3-((3S,4R)-4-(4-methoxyphenyl)-2-oxopyrrolidin-3-yl)urea | 401.1 | 1.27(D) |

TABLE 2-continued

| Ex. No. | Name | Obs (M + H) | RT (min)[a] |
|---|---|---|---|
| 78 | 1-[(3S,4R)-4-(2,6-difluoro-4-methoxyphenyl)-2-oxopyrrolidin-3-yl]-3-(1-phenylcyclopropyl)urea | 402 | 1.37(C) |
| 79 | 3-[1-(5-chloropyridin-2-yl)cyclopropyl]-1-[(3S,4R)-4-(2,6-difluoro-4-methoxyphenyl)-2-o.\opyrrolidin-3-yl]urea | 437.2 | 1.34(D) |
| 80 | 1-((3S,4R)-4-(2,6-difluoro-4-(methoxy-d3)phenyl)-2-oxopyrrolidin-3-yl)-3-(1-(m-tolyl)cyclopropyl)urea | 419.1 | 1.46(D) |
| 81 | 3-[1-(7-chloro-1,3-benzothiazol-2-yl)cyclopropyl]-1-l(3S,4R)-4-(2.6-difluoro-4-methoxyphenyl)-2-oxopyrrolidin-3-yl]urea | 493.0 | 1.49(D) |
| 82 | 1-[(3S,4R)-4-(2,6-difluoro-4-methoxyphenyl)-2-oxopyrrolidin-3-yl]-3-{1-[6-(trifluoromethyl)-1,3-benzothiazol-2-yl]cyclopropyl}urea | 527.1 | 1.68(D) |

TABLE 2-continued

| Ex. No. | Structure[b] | Name | Obs (M + H) | RT (min)[a] |
|---|---|---|---|---|
| 83 | 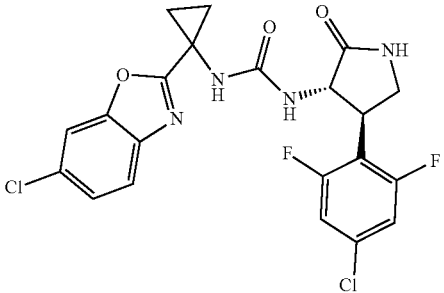 [SMILES: O=C(N[C@@H]1C(=O)NC[C@H]1c1c(F)cc(Cl)cc1F)NC1(c2nc3ccc(Cl)cc3o2)CC1] | 3-[1-(6-chloro-1,3-benzoxazol-2-yl)cyclopropyl]-1-]-(3S,4R)-4-(4-chloro-2,6-difluorophenyl)-2-oxopyrrolidin-3-yl]urea | 481.0 | 1.58(C) |
| 84 | 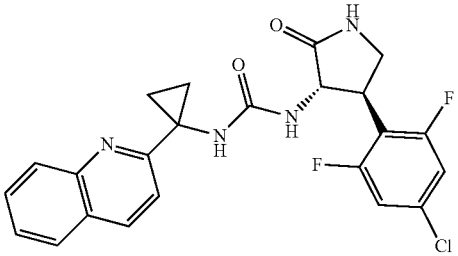 [SMILES: O=C(N[C@@H]1C(=O)NC[C@H]1c1c(F)cc(Cl)cc1F)NC1(c2ccc3ccccc3n2)CC1] | 1-[(3S,4R)-4-(4-chloro-2,6-difluorophenyl)-2-oxopyrrolidin-3-yl]-3-[1-(quinolin-2-yl)cyclopropyl]urea | 457.2 | 1.09(C) |
| 85 | 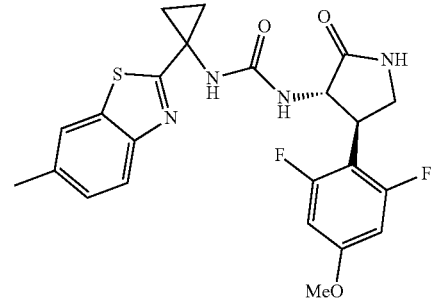 [SMILES: COc1cc(F)c([C@@H]2CNC(=O)[C@H]2NC(=O)NC2(c3nc4ccc(C)cc4s3)CC2)c(F)c1] | 1-[(3S,4R)-4-(2,6-difluoro-4-methoxyphenyl)-2-oxopyrrolidin-3-yl]-3-[1-(6-methyl-1,3-benzothiazol-2-yl)cyclopropyl]urea | 473.2 | 1.44(C) |
| 86 | 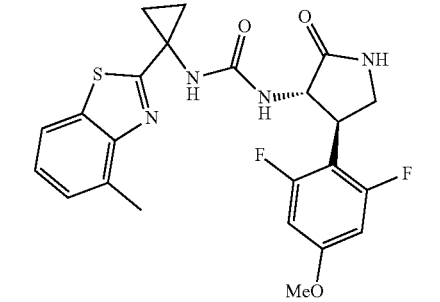 [SMILES: COc1cc(F)c([C@@H]2CNC(=O)[C@H]2NC(=O)NC2(c3nc4c(C)cccc4s3)CC2)c(F)c1] | 1-[(3S,4R)-4-(2,6-difluoro-4-methoxyphenyl)-2-oxopyrrolidin-3-yl]-3-[1-(4-methyl-1,3-benzothiazol-2-yl)cyclopropyl]urea | 472.9 | 1.59(C) |
| 87 | 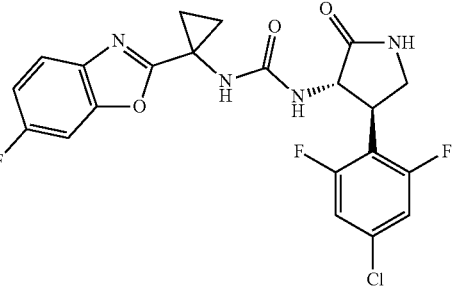 | 1-[(3S,4R)-4-(2,6-difluoro-4-methoxyphenyl)-2-oxopyrrolidin-3-yl]-3-[1-(6-fluoro-1,3-benzoxazol-2-yl)cyclopropyl]urea | 461.0 | 1.36(D) |

TABLE 2-continued

| Ex. No. | Structure[b] | Name | Obs (M + H) | RT (min)[a] |
|---|---|---|---|---|
| 88 | | 3-[1-(6-chloro-1,3-benzoxazol-2-yl)cyclopropyl]-1-[(3S,4R)-4-(6-fluoro-2,3-dihydro-1-benzofuran-5-yl)-2-oxopyrrolidin-3-yl]urea | 471.2 | 1.43(D) |
| 89 | | 1-[(3S,4R)-4-(6-fluoro-2,3-dihydro-1-benzofuran-5-yl)-2-oxopyrrolidin-3-yl]-3-{1-[3-(trifluoromethoxy)phenyl]cyclopropyl}urea | 480.0 | 1.58(D) |
| 90 | | 1-[(3S,4R)-4-(2,6-difluoro-4-methoxyphenyl)-2-oxopyrrolidin-3-yl]-3-[1-(4-methoxy-1,3-benzoxazol-2-yl)cyclopropyl]urea | 473.3 | 1.33(D) |
| 91 | | 3-[1-(6-chloropyridin-2-yl)cyclopropyl]-1-[(3S,4R)-4-[2-fluoro-4-(trifluoromethyl)phenyl]-2-oxopyrrolidin-3-yl]urea | 457.2 | 1.56(D) |
| 92 | | 1-[(3S,4R)-4-(6-fluoro-2,3-dihydro-1-bcn/.ofuran-5-yl)-2-oxopyrrolidin-3-yl]-3-[1-(quinolin-2-yl)cyclopropyl]urea | 447.3 | 0.98(C) |

TABLE 2-continued

| Ex. No. | Structure[b] | Name | Obs (M + H) | RT (min)[a] |
|---|---|---|---|---|
| 93 | | 1-[(3S,4R)-4-(6-fluoro-2,3-dihydro-1-benzofuran-5-yl)-2-oxopyrrolidin-3-yl]-3-[1-(6-methylpyridin-2-yl)cyclopropyl]urea | 411.2 | 1.22(D) |
| 94 | | 1-[(3S,4R)-1-(cyclopropyl-methyl)-4-(2,6-difluoro-4-methoxyphenyl)-2-oxopyrrolidin-3-yl]-3-[1-(6-methylpyridin-2-yl)cyclopropyl]urea | 471.3 | 1.29(C) |
| 95 | | 1-[(3S,4R)-4-(2,6-difluoro-4-methoxyphenyl)-2-oxo-1-propylpyrrolidin-3-yl]-3-[1-(quinolin-2-yl)cyclopropyl]urea | 495.0 | 1.38(C) |
| 96 | | 1-[(3S,4R)-4-(2,6-difluoro-4-methoxyphenyl)-2-oxopyrrolidin-3-yl]-3-{1-[4-(trifluoromethyl)-1,3-benzothiazol-2-yl]cyclopropyl}urea | 527.2 | 1.75(D) |

TABLE 2-continued

| Ex. No. | Structure[b] | Name | Obs (M + H) | RT (min)[a] |
|---|---|---|---|---|
| 97 | | 1-[(3S,4R)-1-(cyanomethyl)-4-(2,6-difluoro-4-methoxyphenyl)-2-oxopyrrolidin-3-yl]-3-[1-(3,5-dichlorophenyl)cyclopropyl]urea | 509.2 | 1.88(C) |
| 98 | | 3-[1-(3,4-dichlorophenyl)cyclopropyl]-1-[(3S,4R)-4-(2,6-difluoro-4-methoxyphenyl)-2-oxo-1-(3,3,3-trifluoropropyl)pyrrolidin-3-yl]urea | 566.2 | 1.97(C) |
| 99 | | 1-[(3S,4R)-4-(2,6-difluoro-4-methoxyphenyl)-2-oxopyrrolidin-3-yl]-3-[1-(8-fluoroquinolin-2-yl)cyclopropyl]urea | 471.2 | 1.42(C) |
| 100 | | 1-[(3S,4R)-4-(4-chloro-2,6-difluorophenyl)-2-oxopyrrolidin-3-yl]-3-[1-(5-chloro-6-methylpyridin-2-yl)cyclopropyl]urea | 455.2 | 2.07(D) |

TABLE 2-continued

| Ex. No. | Name | Obs (M + H) | RT (min)[a] |
|---|---|---|---|
| 101 | 3-[1-(3,5-dichlorophenyl)cyclopropyl]-1-[(3S,4R)-4-(2,6-difluoro-4-methoxyphenyl)-2-oxo-1-propylpyrrolidin-3-yl]urea | 512.1 | 2.07(D) |
| 102 | 1-[(3S,4R)-4-(2,6-difluoro-4-methoxyphenyl)-1-(1-hydroxy-2-methylpropan-2-yl)-2-oxopyrrolidin-3-yl]-3-[1-(6-methylpyridin-2-yl)cyclopropyl]urea | 489.3 | 1.12(C) |
| 103 | 1-[(3S,4R)-4-(2,6-difluoro-4-methoxyphenyl)-2-oxopyrrolidin-3-yl]-3-{1-[8-(2,2,2-trifluoroethoxy)quinolin-2-yl]cyclopropyl}urea | 551.2 | 1.70(D) |
| 104 | 1-[(3S,4R)-4-(2,6-difluoro-4-methoxyphenyl)-2oxo-1-(2,2,2-trifluoroethyl)pyrrolidin-3-yl]-3-[1-(quinolin-2-yl)cyclopropyl]urea | 535.3 | 1.43(C) |

TABLE 2-continued

| Ex. No. | Name | Obs (M + H) | RT (min)[a] |
|---|---|---|---|
| 105 | 3-[1-(3,5-dichlorophenyl)cyclopropyl]-1-[(3S,4R)-4-(2,6-difluoro-4-methoxyphenyl)-2-oxo-1-(2,2,2-trifluoroethyl)pyrrolidin-3-yl]urea | 552.2 | 2.07(C) |
| 106 | 1-[(3S,4R)-1-(cyanomethyl)-4-(2,6-difluoro-4-methoxyphenyl)-2-oxopyrrolidin-3-yl]-3-[1-(quinolin-2-yl)cyclopropyl]urea | 492.3 | 1.69(D) |
| 107 | 3-[1-(3,5-dichlorophenyl)cyclopropyl]-1-[(3S,4R)-4-(2,6-difluoro-4-methoxyphenyl)-1-(2-hydroxyethyl)-2-oxopyrrolidin-3-yl]urea | 514.2 | 1.71(D) |
| 108 | 1-[(3S,4R)-4-(2,6-difluoro-4-methoxyphenyl)-1-(2-methylpropyl)-2-oxopyrrolidin-3-yl]-3-[1-(6-methylpyridin-2-yl)cyclopropyl]urea | 473.3 | 1.40(C) |

TABLE 2-continued

| Ex. No. | Structure | Name | Obs (M + H) | RT (min) |
|---|---|---|---|---|
| 109 | | 1-[(3S,4R)-4-(4-bromo-2,6-difluorophenyl)-2-oxopyrrolidin-3-yl]-3-[1-(quinolin-2-yl)cyclopropyl]urea | 501.0 | 1.60(D) |
| 110 | | 1-[(3S,4R)-4-(2,6-difluoro-4-methoxyphenyl)-2-oxo-1-(2,2,2-trifluoroethyl)pyrrolidin-3-yl]-3-[1-(6-methylpyridin-2-yl)cyclopropyl]urea | 499.4 | 1.71(D) |
| 111 | | 1-[(3S,4R)-1-(cyanomethyl)-4-(2,6-difluoro-4-methoxyphenyl)-2-oxopyrrolidin-3-yl]-3-[1-(6-methylpyridin-2-yl)cyclopropyl]urea | 456.2 | 1.46(D) |
| 112 | | 1-[(3S,4R)-4-(2,6-difluoro-4-methoxyphenyl)-2-oxopyrrolidin-3-yl]-3-[1-(8-methylquinolin-2-yl)cyclopropyl]urea | 467.1 | 1.40(C) |

TABLE 2-continued

| Ex. No. | Structure[b] | Name | Obs (M + H) | RT (min)[a] |
|---|---|---|---|---|
| 113 | | 1-[(3S,4R)-4-(2,6-difluoro-4-methoxyphenyl)-2-oxopyrrolidin-3-yl]-3-[1-(8-methoxyquinolin-2-yl)cyclopropyl]urea | 483.2 | 1.08(C) |
| 114 | | 1-[(3S,4R)-4-(2,6-difluoro-4-methoxyphenyl)-2-oxopyrrolidin-3-yl]-3-{1-[3-(2-methylpropoxy)phenyl]cyclopropyl}urea | 474.3 | 1.77(D) |
| 115 | | 1-[(3S,4R)-4-(2,6-difluoro-4-methoxyphenyl)-1-1(5-methyl-1,3,4-oxadiazol-2-yl)methyl]-2-oxopyrrolidin-3-yl]-3-[1-(6-methylpyridin-2-yl)cyclopropyl]urea | 513.3 | 0.95(C) |
| 116 | | 1-[(3S,4R)-4-(2,6-difluoro-4-methoxyphenyl)-2-oxo-1-(3,3,3-trifluoropropyl)pyrrolidin-3-yl]-3-[1-(6-methylpyridin-2-yl)cyclopropyl]urea | 513.2 | 1.31(C) |

TABLE 2-continued

| Ex. No. | Name | Obs (M + H) | RT (min)a |
|---|---|---|---|
| 117 | 1-[(3S,4R)-4-(2,6-difluoro-4-methoxyphenyl)-1-(2-hydroxyethyl)-2-oxopyrrolidin-3-yl]-3-[1-(6-methylpyridin-2-yl)cyclopropyl]urea | 461.3 | 1.37(D) |
| 118 | 1-[(3S,4R)-4-(2,6-difluoro-4-methoxyphenyl)-1-(2-hydroxy-2-methylpropyl)-2-oxopyrrolidin-3-yl]-3-[1-(6-methylpyridin-2-yl)cyclopropyl]urea | 489.3 | 1.06(C) |
| 119 | 1-[(3S,4R)-4-(4-chloro-2,6-difluorophenyl)-1-[(5-methyl-1,3,4-oxadiazol-2-yl)methyl]-2-oxopyrrolidin-3-yl]-3-[1-(6-methylpyridin-2-yl)cyclopropyl]urea | 517.5 | 1.03(C) |
| 120 | 3-(1-{[1,1'-biphenyl]-3-yl}cyclopropyl)-1-[(3S,4R)-4-(2,6-difluoro-4-methoxyphenyl)-2-oxopyrrolidin-3-yl]urea | 478.0 | 1.72(C) |

TABLE 2-continued

| Ex. No. | Structure | Name | Obs (M + H) | RT (min) |
|---|---|---|---|---|
| 121 | | 3-(1-{3'-chloro-[1,1'-biphenyl]-3-yl}cyclopropyl)-1-[(3S,4R)-4-(2,6-difluoro-4-methoxyphenyl)-2-oxopyrrolidin-3-yl]urea | 512.0 | 2.00(D) |
| 122 | | 1-[(3S,4R)-4-(4-bromo-2,6-difluorophenyl)-2-oxopyrrolidin-3-yl]-3-[1-(6-methylpyridin-2-yl)cyclopropyl]urea | 466.0 | 1.49(D) |
| 123 | | 1-[(3S,4R)-4-(4-chloro-2,6-difluorophenyl)-2-oxopyrrolidin-3-yl]-3-[1-(3,5-dichlorophenyl)cyclopropyl]urea | 474.0 | 1.85(D) |
| 124 | | 1-[(3S,4R)-4-(4-chloro-2,6-difluorophenyl)-2-oxopyrrolidin-3-yl]-3-[1-(6-methylpyridin-2-yl)cyclopropyl]urea | 421.0 | 0.96(C) |

TABLE 2-continued

| Ex. No. | Structure[b] | Name | Obs (M + H) | RT (min)[a] |
|---|---|---|---|---|
| 125 | | 3-(1-{[1,1'-biphenyl]-4-yl}cyclopropyl)-1-[(3S,4R)-4-(2,6-difluoro-4-methoxyphenyl)-2-oxopyrrolidin-3-yl]urea | 478.2 | 1.85(D) |
| 126 | | 1-[(3S,4R)-2-oxo-4-(2,4,6-trifluorophenyl)pyrrolidin-3-yl]-3-[1-(quinolin-2-yl)cyclopropyl]urea | 441.3 | 1.54(D) |
| 127 | | 1-[(3S,4R)-4-(4-cyclopropyl-2,6-difluorophenyl)-2-oxopyrrolidin-3-yl]-3-[1-(quinolin-2-yl)cyclopropyl]urea | 463.2 | 1.33(C) |
| 128 | | 1-[(3S,4R)-4-(2,6-difluoro-4-methoxyphenyl)-2-oxopyrrolidin-3-yl]-3-(1-{3-[(1,2,3,4-tetrahydronaphthalen-2-yl)methoxy]phenyl}cyclopropyl)urea | 562.4 | 2.14(D) |

TABLE 2-continued

| Ex. No. | Structure | Name | Obs (M + H) | RT (min) |
|---|---|---|---|---|
| 129 | 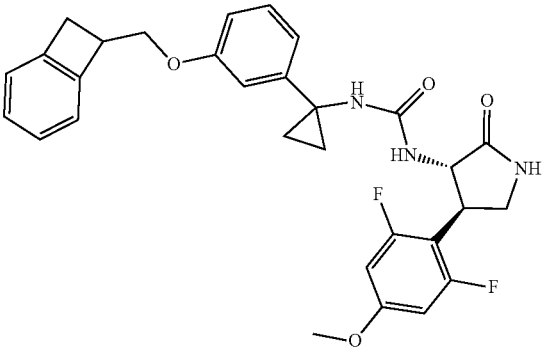 [SMILES: COc1cc(F)c([C@@H]2CNC(=O)[C@H]2NC(=O)NC2(c3cccc(OCC4Cc5ccccc54)c3)CC2)c(F)c1] | 3-{1-[3-({bicyclo[4.2.0]octa-1(6),2,4-trien-7-yl}methoxy)phenyl]cyclopropyl}-1-[(3S,4R)-4-(2,6-difluoro-4-methoxyphenyl)-2-oxopyrrolidin-3-yl]urea | 534.2 | 2.20(D) |
| 130 | 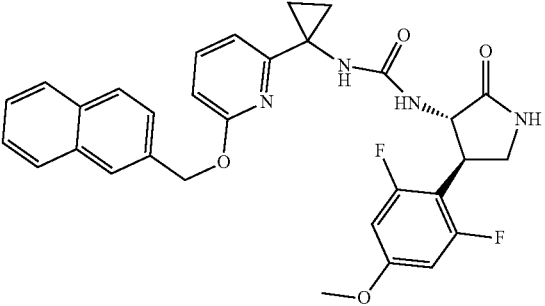 [SMILES: COc1cc(F)c([C@@H]2CNC(=O)[C@H]2NC(=O)NC2(c3cccc(OCc4ccc5ccccc5c4)n3)CC2)c(F)c1] | 1-[(3S,4R)-4-(2,6-difluoro-4-methoxyphenyl)-2-oxopyrrolidin-3-yl]-3-(1-{6-[(naphthalen-2-yl)methoxy]pyridin-2-yl}cyclopropyl)urea | 559.4 | 2.14(C) |
| 131 | 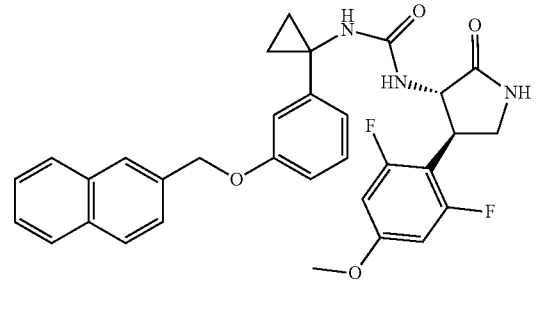 [SMILES: COc1cc(F)c([C@@H]2CNC(=O)[C@H]2NC(=O)NC2(c3cccc(OCc4ccc5ccccc5c4)c3)CC2)c(F)c1] | 1-[(3S,4R)-4-(2,6-difluoro-4-methoxyphenyl)-2-oxopyrrolidin-3-yl]-3-(1-{3-[(naphthalen-2-yl)methoxy]phenyl}cyclopropyl)urea | 558.3 | 2.00(C) |
| 132 | 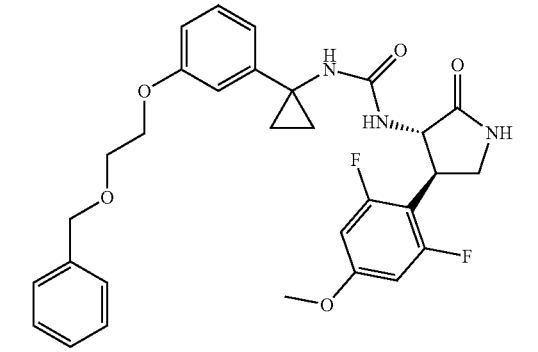 [SMILES: COc1cc(F)c([C@@H]2CNC(=O)[C@H]2NC(=O)NC2(c3cccc(OCCOCc4ccccc4)c3)CC2)c(F)c1] | 3-(1-{3-[2-(benzyloxy)ethoxy]phenyl}cyclopropyl)-1-[(3S,4R)-4-(2,6-difluoro-4-methoxyphenyl)-2-oxopyrrolidin-3-yl]urea | 552.0 | 1.78(D) |

TABLE 2-continued

| Ex. No. | Structure | Name | Obs (M + H) | RT (min) |
|---|---|---|---|---|
| 133 | | 1-[(3S,4R)-4-(2,6-difluoro-4-methoxyphenyl)-2-oxopyrrolidin-3-yl]-3-{1-[3-(4-phenyl-butoxy)phenyl]cyclopropyl}urea | 550.3 | 2.20(D) |
| 134 | | 3-(1-{6-[2-(benzyloxy)ethoxy]pyridin-2-yl}cyclopropyl)-1-[(3S,4R)-4-(2,6-difluoro-4-methoxyphenyl)-2-oxopyrrolidin-3-yl]urea | 553.2 | 1.97(D) |
| 135 | | 3-(1-{1-benzyl-1H-pyrrolo[2,3-b]pyridin-6-yl}cyclopropyl)-1-[(3S,4R)-4-(2,6-difluoro-4-methoxyphenyl)-2-oxopyrrolidin-3-yl]urea | 532.2 | 1.81(D) |
| 136 | | 3-{1-[3-(cyclohexylmethoxy)phenyl]cyclopropyl}-1-[(3S,4R)-4-(2,6-difluoro-4-methoxyphenyl)-2-oxopyrrolidin-3-yl]urea | 514.3 | 2.05(C) |

TABLE 2-continued

| Ex. No. | Structure[b] | Name | Obs (M + H) | RT (min)[a] |
|---|---|---|---|---|
| 137 | | 3-{1-[3-(cyclobutylmethoxy)phenyl]cyclopropyl}-1-[(3S,4R)-4-(2,6-difluoro-4-methoxyphenyl)-2-oxopyrrolidin-3-yl]urea | 486.3 | 1.85(D) |
| 138 | | 1-[(3S,4R)-4-(2,6-difluoro-4-methoxyphenyl)-2-oxopyrrolidin-3-yl]-3-(1-{6-[2-(2,2,2-trifluoroethoxy)ethoxy]pyridin-2-yl}cyclopropyl)urea | 545.1 | 1.62(D) |
| 139 | | 3-{1-[3-({bicyclo[4.2.0]octa-1(6),2,4-trien-7-yl}methoxy)phenyl]cyclopropyl}-1-[(3S,4R)-4-(2,6-difluoro-4-methoxyphenyl)-2-oxopyrrolidin-3-yl]urea | 534.2 | 1.91(D) |
| 140 | | 3-[1-(1-benzyl-1H-indazol-6-yl)cyclopropyl]-1-[(3S,4R)-4-(2,6-difluoro-4-methoxyphenyl)-2-oxopyrrolidin-3-yl]urea | 523.3 | 1.70(D) |

TABLE 2-continued

| Ex. No. | Structure[b] | Name | Obs (M + H) | RT (min)[a] |
|---|---|---|---|---|
| 141 | | 1-[(3S,4R)-4-(2,6-difluoro-4-methoxyphenyl)-2-oxopyrrolidin-3-yl]-3-[1-(3-phenoxyphenyl)cyclopropyl]urea | 494.3 | 1.93(D) |
| 142 | | 3-[1-(2-benzyl-2H-indazol-6-yl)cyclopropyl]-1-[(3S,4R)-4-(2,6-difluoro-4-methoxyphenyl)-2-oxopyrrolidin-3-yl]urea | 532.3 | 1.66(D) |

[a]Analytical method shown in parentheses
[b]NMR data for representative compounds in Table 2:

Example 11: $^1$H NMR (500 MHz, DMSO-d$_6$) δ 7.92 (br s, 1H), 7.22 (br d, J=8.2 Hz, 2H), 7.00 (br d, J=7.9 Hz, 2H), 6.90 (s, 1H), 6.73 (br d, J=10.7 Hz, 2H), 6.25 (br d, J=8.5 Hz, 1H), 4.44 (br s, 1H), 3.77 (s, 4H), 3.49-3.22 (m, 2H), 1.10 (br s, 4H).

Example 12: $^1$H NMR (500 MHz, DMSO-d6) δ 7.92 (br s, 1H), 7.14-7.05 (m, 1H), 6.84 (s, 1H), 6.75-6.64 (m, 3H), 6.62 (br s, 1H), 6.58 (br d, J=7.3 Hz, 1H), 6.21 (br d, J=8.5 Hz, 1H), 4.46 (br t, J=9.5 Hz, 1H), 3.76 (s, 4H), 3.69 (s, 3H), 3.37 (br s, 1H), 3.28 (br t, J=9.3 Hz, 1H), 1.14-1.02 (m, 4H).

Example 13: $^1$H NMR (500 MHz, DMSO-d6) δ 7.95 (br s, 1H), 7.26-7.16 (m, 1H), 6.97-6.87 (m, 2H), 6.85-6.78 (m, 2H), 6.71 (br d, J=11.0 Hz, 2H), 6.29 (br d, J=8.4 Hz, 1H), 4.44 (br t, J=9.6 Hz, 1H), 3.75 (s, 3H), 3.41-3.37 (m, 1H), 3.34-3.26 (m, 1H), 3.17 (d, J=5.2 Hz, 1H), 1.22-1.03 (m, 4H).

Example 14: $^1$H NMR (500 MHz, DMSO-d6) δ 7.92 (br s, 1H), 7.09-6.94 (m, 4H), 6.88 (s, 1H), 6.72 (br d, J=11.0 Hz, 2H), 6.23 (br d, J=8.2 Hz, 1H), 4.44 (br t, J=9.5 Hz, 1H), 3.76 (s, 4H), 3.39 (br d, J=8.9 Hz, 1H), 3.29 (br t, J=9.3 Hz, 1H), 1.07 (br s, 4H).

Example 16: $^1$H NMR (500 MHz, DMSO-d$_6$) δ 8.37 (br d, J=3.4 Hz, 1H), 7.94 (br s, 1H), 7.64-7.52 (m, 1H), 7.20 (br d, J=7.3 Hz, 1H), 7.09 (br d, J=4.9 Hz, 1H), 6.94 (s, 1H), 6.74 (br d, J=11.0 Hz, 2H), 6.35 (br d, J=8.5 Hz, 1H), 4.47 (br t, J=9.5 Hz, 1H), 3.76 (s, 4H), 3.45-3.12 (m, 2H), 1.38 (br s, 1H), 1.12-0.90 (m, 2H).

Example 17: $^1$H NMR (500 MHz, DMSO-d$_6$) δ 7.95 (br s, 1H), 7.51-7.43 (m, 1H), 6.99 (br s, 1H), 6.97-6.88 (m, 2H), 6.74 (br d, J=10.9 Hz, 2H), 6.34 (br d, J=8.3 Hz, 1H), 4.46 (br t, J=9.3 Hz, 1H), 3.85-3.70 (m, 4H), 3.44-3.33 (m, 1H), 3.33-3.24 (m, 1H), 2.35 (s, 3H), 1.36 (br d, J=18.1 Hz, 2H), 1.08-0.91 (m, 2H).

Example 18: $^1$H NMR (500 MHz, DMSO-d$_6$) δ 7.94 (br. s., 1H), 7.62 (d, J=8.2 Hz, 2H), 7.12 (d, J=7.9 Hz, 2H), 7.00 (s, 1H), 6.73 (d, J=10.9 Hz, 2H), 6.34 (d, J=8.4 Hz, 1H), 4.43 (br t, J=9.4 Hz, 1H), 3.76 (s, 3H), 3.61-3.56 (m, 1H), 3.39 (br t, J=8.9 Hz, 1H), 3.35-3.24 (m, 1H), 1.28-1.14 (m, 4H).

Example 20: $^1$H NMR (500 MHz, DMSO-d$_6$) δ 7.92 (br s, 1H), 7.11-7.02 (m, 1H), 6.91 (br d, J=7.3 Hz, 1H), 6.86 (br s, 1H), 6.83-6.75 (m, 2H), 6.71 (br d, J=10.7 Hz, 2H), 6.21 (br d, J=8.2 Hz, 1H), 4.45 (br t, J=9.5 Hz, 1H), 3.76 (s, 4H), 3.41 (br s, 1H), 3.28 (br t, J=9.3 Hz, 1H), 2.23 (s, 3H), 1.08 (br s, 4H).

Example 22: $^1$H NMR (500 MHz, DMSO-d$_6$) δ 7.91 (br s, 1H), 6.92 (br d, J=7.8 Hz, 2H), 6.82 (br s, 1H), 6.76-6.66 (m, 4H), 6.19 (br d, J=8.3 Hz, 1H), 4.44 (br t, J=9.6 Hz, 1H), 3.79 (br s, 3H), 3.69 (s, 3H), 3.64-3.49 (m, 1H), 3.39 (br t, J=9.0 Hz, 1H), 3.28 (br t, J=9.6 Hz, 1H), 1.12-0.94 (m, 4H).

Example 23: $^1$H NMR (500 MHz, DMSO-d$_6$) δ 8.75 (br s, 1H), 7.96 (br s, 2H), 7.35 (br s, 1H), 7.17 (br s, 1H), 6.76 (br d, J=11.1 Hz, 2H), 6.51 (br s, 1H), 4.46 (br d, J=10.4 Hz, 1H), 3.75 (s, 4H), 3.46-3.34 (m, 1H), 3.35-3.23 (m, 1H), 1.53-1.37 (m, 2H), 1.16 (br s, 2H).

Example 24: $^1$H NMR (500 MHz, DMSO-d$_6$) δ 7.92 (br. s., 1H), 7.27-7.18 (m, 1H), 7.18-7.07 (m, 1H), 7.07 (s, 1H), 6.97-6.86 (m, 3H), 6.70 (d, J=10.7 Hz, 2H), 6.27 (d, J=8.5 Hz, 1H), 4.43 (t, J=9.6 Hz, 1H), 3.89 (s, 1H), 3.80-3.63 (m, 3H), 3.44-3.24 (m, 1H), 3.16 (d, J=5.2 Hz, 1H), 1.20-1.03 (m, 4H).

Example 25: ¹H NMR (500 MHz, DMSO-d₆) δ 7.91 (br. s., 1H), 7.76 (q, J=7.9 Hz, 1H), 7.10 (br. s., 1H), 6.99 (s, 1H), 6.84 (d, J=6.1 Hz, 1H), 6.71 (d, J=11.0 Hz, 2H), 6.39 (d, J=8.9 Hz, 1H), 4.43 (t, J=9.5 Hz, 1H), 3.73 (s, 3H), 3.41-3.34 (m, 1H), 3.30 (t, J=9.6 Hz, 1H), 3.16 (d, J=4.9 Hz, 1H), 1.31 (br. s., 2H), 1.08 (br. s., 2H).

Example 26: ¹H NMR (500 MHz, DMSO-d₆) δ 8.23 (br d, J=8.2 Hz, 1H), 7.93 (br d, J=8.2 Hz, 1H), 7.85 (br d, J=8.2 Hz, 1H), 7.71 (br t, J=7.5 Hz, 1H), 7.53 (br t, J=7.4 Hz, 1H), 7.46-7.40 (m, 1H), 7.32-7.03 (m, 2H), 6.73 (br d, J=10.8 Hz, 2H), 6.49 (br d, J=7.7 Hz, 1H), 4.56-4.41 (m, 1H), 3.63 (br s, 4H), 3.44-3.36 (m, 1H), 3.30 (br s, 1H), 1.67-1.52 (m, 2H), 1.18 (br s, 2H).

Example 27: ¹H NMR (500 MHz, DMSO-d₆) δ 7.88 (br. s., 1H), 7.28 (s, 1H), 7.06-6.92 (m, 3H), 6.65 (d, J=10.7 Hz, 2H), 6.33 (d, J=8.5 Hz, 1H), 4.52-4.35 (m, 1H), 3.82-3.59 (m, 4H), 3.38 (br. s., 1H), 3.28 (s, 1H), 1.23-1.04 (m, 4H).

Example 28: ¹H NMR (500 MHz, DMSO-d₆) δ 7.90 (br. s., 1H), 6.92 (s, 1H), 6.76-6.59 (m, 3H), 6.36-6.25 (m, 1H), 4.55-4.41 (m, 1H), 3.72 (s, 3H), 3.46-3.33 (m, 1H), 3.29-3.18 (m, 1H), 3.15 (d, J=5.1 Hz, 1H), 2.24 (s, 6H), 1.45-1.28 (m, 2H), 1.15-1.01 (m, 2H).

Example 29: ¹H NMR (500 MHz, DMSO-d₆) δ 9.13 (s, 1H), 8.03 (d, J=8.2 Hz, 1H), 7.93 (br. s., 1H), 7.82-7.67 (m, 2H), 7.66-7.50 (m, 2H), 7.02 (s, 1H), 6.69 (d, J=10.7 Hz, 2H), 6.41 (d, J=8.5 Hz, 1H), 4.47 (d, J=10.4 Hz, 1H), 3.71 (s, 3H), 3.39-3.20 (m, 1H), 1.90 (br. s., 2H), 1.48 (br. s., 2H), 1.19-1.04 (m, 2H).

Example 30: ¹H NMR (500 MHz, DMSO-d₆) δ 8.02 (br s, 1H), 7.33-7.14 (m, 3H), 7.14-6.98 (m, 1H), 6.80-6.64 (m, 2H), 4.51-4.28 (m, 1H), 3.82-3.70 (m, 4H), 3.47-3.34 (m, 1H), 3.34-3.20 (m, 1H), 2.48 (br s, 3H), 2.34 (br s, 3H), 1.50-1.35 (m, 2H), 1.25-1.05 (m, 2H).

Example 31: ¹H NMR (500 MHz, DMSO-d₆) δ 7.98-7.92 (m, 1H), 7.92-7.83 (m, 1H), 7.79-7.73 (m, 1H), 7.55-7.44 (m, 1H), 7.11 (s, 1H), 6.75 (br d, J=10.7 Hz, 2H), 6.46 (d, J=8.5 Hz, 1H), 4.45 (br t, J=9.8 Hz, 1H), 3.76 (s, 4H), 3.47-3.13 (m, 2H), 1.42 (br d, J=3.4 Hz, 2H), 1.14 (br s, 2H).

Example 33: ¹H NMR (500 MHz, DMSO-d₆) δ ppm 7.61 (br t, J=7.74 Hz, 1H), 7.11 (br d, J=7.49 Hz, 1H), 7.04-7.08 (m, 1H), 7.02 (br s, 1H), 6.73 (br d, J=10.94 Hz, 2H), 6.45 (br d, J=7.41 Hz, 1H), 4.45 (br t, J=9.34 Hz, 1H), 3.74 (s, 3H), 3.56 (br d, J=7.57 Hz, 1H), 3.44-3.52 (m, 1H), 3.39 (br t, J=9.13 Hz, 1 H), 2.78 (s, 3H), 2.39 (s, 3H), 1.39 (br d, J=10.18 Hz, 2H), 1.06 (br s, 2H).

Example 34: ¹H NMR (500 MHz, DMSO-d₆) δ 8.20 (s, 1H), 7.95 (br s, 1H), 7.40 (br d, J=7.6 Hz, 1H), 7.08 (br d, J=4.9 Hz, 1H), 6.93 (s, 1H), 6.75 (br d, J=11.1 Hz, 2H), 6.33 (br d, J=8.4 Hz, 1H), 4.46 (br t, J=9.5 Hz, 1H), 3.76 (s, 3H), 3.65-3.57 (m, 1H), 3.46-3.36 (m, 1H), 3.30 (br t, J=9.4 Hz, 1H), 2.22 (s, 3H), 1.33 (br d, J=15.7 Hz, 2H), 1.07-0.96 (m, 2H)

Example 35: ¹H NMR (500 MHz, DMSO-d6) δ 7.98 (br s, 1H), 7.67 (d, J=8.9 Hz, 1H), 7.50 (br s, 1H), 7.39 (br s, 1H), 7.01 (dd, J=8.9, 2.4 Hz, 1H), 6.75 (br d, J=10.9 Hz, 2H), 6.50 (br s, 1H), 4.54 (br t, J=8.8 Hz, 1H), 3.82 (s, 3H), 3.83-3.74 (m, 1H), 3.72 (s, 3H), 3.47-3.36 (m, 1H), 3.30 (br t, J=9.8 Hz, 1H), 1.65-1.41 (m, 2H), 1.26 (br s, 2H).

Example 36: ¹H NMR (500 MHz, DMSO-d₆) δ 7.95 (br s, 1H), 7.39 (br d, J=8.1 Hz, 1H), 7.21 (br s, 1H), 7.13 (br d, J=10.0 Hz, 1H), 7.07 (s, 1H), 6.67 (br d, J=10.9 Hz, 2H), 6.38 (br d, J=8.3 Hz, 1H), 4.43 (br t, J=9.6 Hz, 1H), 3.74 (s, 4H), 3.44-3.34 (m, 1H), 3.28 (br t, J=9.4 Hz, 1H), 1.32-1.09 (m, 4H).

1H NMR (500 MHz, DMSO-d6) δ ppm 7.92 (br s, 1H) 7.32-7.37 (m, 4H) 7.24-7.31 (m, 2H) 7.09 (t, J=7.93 Hz, 1H) 6.83 (s, 1H) 6.69 (br d, J=10.68 Hz, 3H) 6.56-6.65 (m, 2H) 6.19 (br d, J=8.54 Hz, 1H) 4.55 (s, 2H) 4.44 (br t, J=9.61 Hz, 1H) 4.05-4.12 (m, 2H) 3.74-3.78 (m, 2H) 3.73 (s, 3H) 3.23-3.31 (m, 1H) 1.00-1.16 (m, 4H). Two protons obscured by water suppression.

Example 38: ¹H NMR (500 MHz, DMSO-d₆) δ 7.92 (s, 1H), 7.82 (s, 1H), 7.65 (s, 2H), 7.14 (s, 1H), 6.64 (d, J=11.0 Hz, 2H), 6.41 (d, J=8.5 Hz, 1H), 4.48-4.31 (m, 1H), 3.74 (s, 3H), 3.59-3.47 (m, 1H), 3.44-3.07 (m, 2H), 1.32 (br s, 2H), 1.20 (br d, J=5.5 Hz, 2H).

Example 39: ¹H NMR (500 MHz, DMSO-d₆) δ 7.94 (br s, 1H), 7.32 (br t, J=8.2 Hz, 1H), 7.09 (br d, J=7.7 Hz, 1H), 6.97 (br s, 3H), 6.68 (br d, J=10.9 Hz, 2H), 6.32 (br d, J=8.4 Hz, 1H), 4.43 (br t, J=9.6 Hz, 1H), 3.74 (s, 3H), 3.43-3.35 (m, 1H), 3.28 (br t, J=9.7 Hz, 1H), 3.17 (br d, J=5.0 Hz, 1H), 1.15 (br s, 4H).

Example 40: ¹H NMR (500 MHz, DMSO-d₆) δ 7.93 (br s, 1H), 7.18 (br d, J=8.3 Hz, 1H), 6.98 (br s, 1H), 6.90 (br s, 1H), 6.80 (br d, J=6.5 Hz, 1H), 6.71 (br d, J=10.9 Hz, 2H), 6.26 (br d, J=8.2 Hz, 1H), 4.43 (br t, J=9.6 Hz, 1H), 3.74 (s, 3H), 3.39 (br t, J=9.1 Hz, 1H), 3.34-3.23 (m, 1H), 3.16 (br d, J=5.0 Hz, 1H), 2.23 (s, 3H), 1.09 (br s, 4H).

Example 41: ¹H NMR (500 MHz, DMSO-d₆) δ 7.94 (br s, 1H), 7.06 (br s, 2H), 7.00 (br s, 1H), 6.71 (br d, J=10.9 Hz, 2H), 6.42 (br d, J=8.3 Hz, 1H), 4.43 (br t, J=9.2 Hz, 1H), 3.74 (s, 3H), 3.48-3.36 (m, 1H), 3.29 (br t, J=9.3 Hz, 1H), 3.16 (br d, J=4.0 Hz, 1H), 2.24 (s, 3H), 1.32 (br s, 2H), 1.07 (br s, 2H).

Example 42: ¹H NMR (500 MHz, DMSO-d₆) δ 7.93 (s, 1H), 7.42 (d, J=8.5 Hz, 1H), 7.25 (d, J=1.8 Hz, 1H), 7.00-6.91 (m, 2H), 6.71 (br d, J=10.7 Hz, 2H), 6.30 (d, J=8.5 Hz, 1H), 4.44 (br t, J=9.8 Hz, 1H), 3.76 (s, 3H), 3.76 (m, 1H), 3.41 (m, 1H), 3.29 (m, 1H), 1.24-1.05 (m, 4H).

Example 43: ¹H NMR (500 MHz, DMSO-d₆) δ 9.17 (s, 1H), 8.51 (d, J=5.49 Hz, 1H), 8.25 (d, J=8.54 Hz, 1H), 7.93 (br s, 1H), 7.84 (d, J=5.49 Hz, 1H), 7.65 (br d, J=8.54 Hz, 1H), 7.16 (s, 1H), 6.72 (br d, J=10.68 Hz, 2H), 6.47 (d, J=8.54 Hz, 1H), 4.46 (br t, J=9.61 Hz, 1H), 3.76-3.84 (m, 1H), 3.74 (s, 3H), 3.40 (br t, J=9.46 Hz, 1H), 3.30 (br t, J=9.61 Hz, 1H), 1.53-1.75 (m, 2H), 1.20 (br s, 2 H).

Example 44: ¹H NMR (500 MHz, DMSO-d₆) δ 8.29 (br s, 2H), 7.30-7.10 (m, 1H), 7.05 (d, J=5.5 Hz, 2H), 6.71 (br d, J=10.7 Hz, 2H), 6.43 (br d, J=8.2 Hz, 1H), 4.44 (br t, J=9.8 Hz, 1H), 3.89 (s, 1H), 3.82-3.72 (m, 3H), 3.51-3.36 (m, 1H), 3.35-3.26 (m, 1H), 2.39 (s, 3H), 1.43-1.29 (m, 2H), 1.13-1.04 (m, 2H).

Example 45: ¹H NMR (500 MHz, DMSO-d₆) δδ 7.91-7.86 (m, 1H), 7.64 (br d, J=8.9 Hz, 1H), 7.52-7.44 (m, 1H), 7.10-7.03 (m, 1H), 6.98-6.92 (m, 1H), 6.72 (br d, J=11.0 Hz, 2H), 6.43-6.36 (m, 1H), 6.35-6.28 (m, 1H), 4.69-4.35 (m, 1H), 3.80-3.66 (m, 1H), 3.76 (s, 3H), 3.45-3.34 (m, 1H), 3.34-3.25 (m, 1H), 1.92-1.89 (m, 3H), 1.46-1.29 (m, 2H), 1.10-0.96 (m, 2H).

Example 46: ¹H NMR (500 MHz, DMSO-d₆) δ 7.90 (s, 1H), 7.46 (d, J=8.5 Hz, 1H), 7.15 (s, 1H), 7.08-6.87 (m, 2H), 6.66 (br d, J=10.7 Hz, 2H), 6.33 (d, J=8.5 Hz, 1H), 4.43 (br t, J=9.8 Hz, 1H), 3.84-3.55 (m, 1H), 3.74 (s, 3H), 3.39 (br t, J=9.3 Hz, 1H), 3.33-3.22 (m, 1H), 1.27-1.01 (m, 4H).

Example 47: ¹H NMR (500 MHz, DMSO-d₆) δ 7.93 (br s, 1H), 7.62 (d, J=8.2 Hz, 1H), 7.03 (br d, J=7.3 Hz, 1H), 6.96 (br s, 1H), 6.75 (br d, J=10.7 Hz, 2H), 6.34 (d, J=8.5 Hz, 1H), 4.55-4.25 (m, 1H), 3.77 (s, 3H), 3.77 (1H, m), 3.30 (m, 1H), 3.16 (m, 1H), 2.43 (s, 3H), 1.46-1.28 (m, 2H), 1.05 (br s, 2H).

Example 49: ¹H NMR (500 MHz, DMSO-d₆) δ 7.90 (br s, 1H), 7.80 (d, J=8.5 Hz, 1H), 7.69 (d, J=5.2 Hz, 1H), 7.57 (s, 1H), 7.38-7.21 (m, 1H), 7.10-6.88 (m, 2H), 6.71-6.64 (m, 2H), 6.29-6.22 (m, 1H), 4.44 (br t, J=9.6 Hz, 1H), 3.73 (s, 3H), 3.61-3.51 (m, 1H), 3.40 (br t, J=9.2 Hz, 1H), 3.33-3.24 (m, 1H), 1.94-1.86 (m, 1H), 1.15 (br d, J=5.5 Hz, 4H).

Example 50: $^1$H NMR (500 MHz, DMSO-d$_6$) δ 7.91 (br s, 1H), 7.15 (d, J=7.9 Hz, 1H), 7.05 (s, 1H), 6.89 (s, 1H), 6.84 (br d, J=7.6 Hz, 1H), 6.70 (br d, J=11.0 Hz, 2H), 6.23 (d, J=8.5 Hz, 1H), 4.49-4.39 (m, 1H), 3.75 (s, 3H), 3.54-3.44 (m, 1H), 3.43-3.35 (m, 1H), 3.28 (br t, J=9.5 Hz, 1H), 2.25 (s, 3H), 1.15-0.97 (m, 4H).

Example 51: $^1$H NMR (500 MHz, DMSO-d$_6$) δ 7.91 (s, 1H), 7.18 (d, J=8.5 Hz, 1H), 7.02 (s, 1H), 6.97-6.91 (m, 1H), 6.85 (br d, J=7.9 Hz, 1H), 6.67 (br d, J=11.0 Hz, 2H), 6.27 (d, J=8.5 Hz, 1H), 4.42 (br t, J=9.8 Hz, 1H), 3.74 (s, 3H), 3.62 (br d, J=8.5 Hz, 1H), 3.39 (s, 1H), 3.35-3.25 (m, 1H), 1.16-1.01 (m, 4H).

Example 52: $^1$H NMR (500 MHz, DMSO-d6) δ 7.94 (br s, 1H), 7.57-7.43 (m, 2H), 7.25 (br d, J=7.9 Hz, 1H), 6.75 (s, 1H), 6.66 (br d, J=10.7 Hz, 2H), 6.16 (br d, J=8.2 Hz, 1H), 4.36 (br t, J=9.5 Hz, 1H), 3.76 (s, 3H), 3.60 (br d, J=9.2 Hz, 1H), 3.39 (br d, J=8.5 Hz, 1H), 3.24 (br t, J=9.0 Hz, 1H), 1.05-0.90 (m, 4H).

Example 53: $^1$H NMR (500 MHz, DMSO-d$_6$) δ 8.18 (br d, J=8.85 Hz, 1H) 8.03 (d, J=1.83 Hz, 1H) 7.89-7.98 (m, 1H) 7.82 (d, J=9.16 Hz, 1H) 7.67 (dd, J=9.00, 2.29 Hz, 1H) 7.48 (br d, J=8.54 Hz, 1H) 7.12 (s, 1H) 6.73 (br d, J=10.68 Hz, 2H) 6.45 (br d, J=8.54 Hz, 1H) 4.46 (br t, J=9.46 Hz, 1H) 3.76-3.85 (m, 1H) 3.74 (s, 3H) 3.41 (br t, J=8.70 Hz, 1H) 3.23-3.34 (m, 1H) 1.49-1.67 (m, 2H) 1.10-1.25 (m, 2H)

Example 54: $^1$H NMR (500 MHz, DMSO-d$_6$) δ 8.17 (d, J=5.5 Hz, 1H), 7.94 (br s, 1H), 7.04 (br d, J=18.9 Hz, 2H), 6.94-6.89 (m, 1H), 6.72 (br d, J=10.7 Hz, 2H), 6.45-6.35 (m, 1H), 4.50-4.37 (m, 1H), 3.76 (s, 3H), 3.56-3.37 (m, 1H), 3.34-3.23 (m, 1H), 3.17 (m, 1H), 1.33-1.16 (m, 4H).

Example 55: $^1$H NMR (500 MHz, DMSO-d$_6$) δ 7.92 (s, 1H), 7.63 (s, 1H), 7.55 (d, J=8.54 Hz, 1H), 7.34 (dd, J=8.70, 1.68 Hz, 1H), 7.16 (s, 1H), 6.66 (br d, J=10.99 Hz, 2H), 6.45-6.60 (m, 1H), 4.44 (br t, J=9.46 Hz, 1H), 3.67-3.73 (m, 1H), 3.65 (s, 3H), 3.39 (br t, J=8.70 Hz, 1H), 3.22-3.35 (m, 1H), 1.46-1.58 (m, 2H), 1.26 (m, J=10.70 Hz, 2H).

Example 56: $^1$H NMR (500 MHz, DMSO-d$_6$) δ 7.98-7.90 (m, 2H), 7.79 (d, J=7.9 Hz, 1H), 7.49-7.39 (m, 2H), 7.39-7.29 (m, 1H), 6.72 (br d, J=11.0 Hz, 2H), 6.52 (br d, J=7.0 Hz, 1H), 4.61-4.44 (m, 1H), 3.71 (s, 3H), 3.65-3.48 (m, 1H), 3.45-3.37 (m, 1H), 3.37-3.26 (m, 1H), 1.72-1.45 (m, 2H), 1.31 (br s, 2H).

Example 57: $^1$H NMR (500 MHz, DMSO-d$_6$) δ 8.20 (br d, J=3.7 Hz, 1H), 7.99 (s, 1H), 7.92 (s, 1H), 7.24 (br s, 1H), 7.02-6.85 (m, 2H), 6.66 (br d, J=11.0 Hz, 2H), 6.13 (br d, J=8.2 Hz, 1H), 4.48 (br t, J=9.5 Hz, 1H), 3.75 (s, 3H), 3.71 (s, 3H), 3.50-3.42 (m, 1H), 3.41-3.32 (m, 1H), 3.26 (br t, J=9.6 Hz, 1H), 1.19-0.87 (m, 4H).

Example 58: $^1$H NMR (500 MHz, DMSO-d$_6$) δ 7.93 (s, 2H), 7.57 (d, J=8.5 Hz, 1H), 7.33 (s, 1H), 6.99 (s, 1H), 6.78 (br d, J=8.5 Hz, 1H), 6.66 (br d, J=10.7 Hz, 2H), 6.28 (br d, J=8.5 Hz, 1H), 4.45 (br t, J=9.6 Hz, 1H), 3.96 (s, 3H), 3.74 (s, 3H), 3.68-3.56 (m, 1H), 3.40 (br s, 1H), 3.33-3.21 (m, 1H), 1.30-1.04 (m, 4H).

Example 59: $^1$H NMR (500 MHz, DMSO-d$_6$) δ 7.94 (s, 1H) 7.68 (s, 1H) 7.59 (d, J=8.54 Hz, 1H) 7.37 (br d, J=8.24 Hz, 1H) 7.19 (s, 1H) 6.68 (d, J=11.00 Hz, 2H) 6.53 (d, J=8.50 Hz, 1H) 4.47 (t, J=9.60 Hz, 1H) 3.74-3.82 (m, 1H) 3.73 (s, 3H) 3.40 (br t, J=8.85 Hz, 1H) 3.23-3.33 (m, 1H) 1.47-1.60 (m, 2H) 1.26 (m, J=12.50 Hz, 2H).

Example 60: $^1$H NMR (500 MHz, DMSO-d$_6$) δ 0.96-7.88 (m, 1H), 7.82 (d, J=7.9 Hz, 1H), 7.73 (br dd, J=14.5, 8.4 Hz, 2H), 7.56 (br s, 1H), 7.51-7.35 (m, 2H), 7.10 (br d, J=8.5 Hz, 1H), 6.98 (s, 1H), 6.67 (br d, J=10.4 Hz, 2H), 6.31 (br d, J=8.5 Hz, 1H), 4.46 (br t, J=9.5 Hz, 1H), 3.77-3.60 (m, 4H), 3.41 (br t, J=8.5 Hz, 1H), 3.34-3.24 (m, 1H), 1.30-1.05 (m, 4H).

Example 61: $^1$H NMR (500 MHz, DMSO-d$_6$) δ 7.93 (br s, 1H), 7.88 (s, 1H), 7.54-7.49 (m, 2H), 7.45 (br t, J=7.6 Hz, 2H), 7.37-7.26 (m, 2H), 6.60 (br d, J=10.7 Hz, 2H), 6.50 (br d, J=7.9 Hz, 1H), 4.51 (br s, 1H), 3.78-3.63 (m, 1H), 3.60 (s, 3H), 3.41 (br t, J=9.5 Hz, 1H), 3.29 (br t, J=9.5 Hz, 1H), 1.53-1.35 (m, 2H), 1.22 (br s, 2H).

Example 62: $^1$H NMR (500 MHz, DMSO-d$_6$) δ 7.91 (br s, 1H), 7.62 (br d, J=8.2 Hz, 1H), 7.27 (s, 1H), 7.12-6.99 (m, 2H), 6.68 (br d, J=11.0 Hz, 2H), 6.37 (br d, J=8.5 Hz, 1H), 4.44 (br t, J=9.0 Hz, 1H), 3.74 (s, 1H), 3.70-3.56 (m, 3H), 3.44-3.35 (m, 1H), 3.30 (br t, J=9.3 Hz, 1H), 1.32-1.12 (m, 4H).

Example 63: $^1$H NMR (500 MHz, DMSO-d$_6$) δ 7.93 (br s, 1H), 7.65 (t, J=9.8 Hz, 2H), 7.51 (s, 1H), 7.24 (d, J=1.5 Hz, 1H), 7.17-7.03 (m, 2H), 6.94 (s, 1H), 6.70 (br d, J=11.0 Hz, 2H), 6.28 (br d, J=8.5 Hz, 1H), 4.47 (br t, J=9.6 Hz, 1H), 3.85 (s, 3H), 3.73 (s, 3H), 3.46 (br d, J=5.8 Hz, 2H), 3.29 (br t, J=9.5 Hz, 1H), 1.25-1.08 (m, 4H).

Example 64: $^1$H NMR (500 MHz, DMSO-d$_6$) δ 9.30 (s, 1H), 8.01-7.87 (m, 2H), 7.82 (s, 1H), 7.18 (br d, J=8.5 Hz, 1H), 7.04 (s, 1H), 6.71 (br d, J=11.1 Hz, 2H), 6.34 (br d, J=8.6 Hz, 1H), 4.44 (br s, 1H), 3.95-3.77 (m, 1H), 3.82-3.69 (m, 3H), 3.29 (br s, 1H), 3.20-3.05 (m, 1H), 1.23-1.10 (m, 4H).

Example 65: $^1$H NMR (500 MHz, DMSO-d$_6$) δ 9.35 (s, 1H), 7.98 (br d, J=8.5 Hz, 2H), 7.79 (s, 1H), 7.18 (br d, J=8.2 Hz, 1H), 7.11-6.99 (m, 1H), 6.69 (br d, J=10.9 Hz, 2H), 6.34 (br d, J=8.2 Hz, 1H), 4.44 (br t, J=9.6 Hz, 1H), 3.73 (s, 3H), 3.53-3.47 (m, 2H), 3.29 (br s, 1H), 1.23-1.09 (m, 4H).

Example 66: $^1$H NMR (500 MHz, DMSO-d$_6$) δ 7.95 (br s, 1H), 7.28 (br s, 1H), 7.14 (br d, J=17.8 Hz, 2H), 7.00 (s, 1H), 6.68 (br d, J=11.0 Hz, 2H), 6.31 (br d, J=8.5 Hz, 1H), 4.45 (br d, J=9.3 Hz, 1H), 3.75 (s, 3H), 3.55-3.47 (m, 2H), 3.31-3.22 (m, 1H), 2.32 (s, 3H), 1.32-1.03 (m, 4H).

Example 67: $^1$H NMR (500 MHz, CD$_3$CN) 6 ppm 8.12 (d, J=8.53 Hz, 1H) 7.84 (d, J=7.70 Hz, 1H) 7.82 (d, J=8.25 Hz, 1H) 7.61-7.72 (m, 1H) 7.44-7.54 (m, 2H) 6.54 (br d, J=10.45 Hz, 2H) 6.01-6.16 (m, 1H) 5.75 (br d, J=7.70 Hz, 1H) 4.48-4.62 (m, 1H) 3.76-3.85 (m, 1H) 3.75 (s, 3H) 3.57-3.65 (m, 2H) 3.54 (br d, J=9.08 Hz, 2H) 3.29-3.41 (m, 2H) 1.19-1.33 (m, 4H).

Example 68: $^1$H NMR (500 MHz, DMSO-d$_6$) δ 7.89 (br s, 1H), 7.25-7.13 (m, 2H), 6.95 (s, 2H), 6.68 (br d, J=10.7 Hz, 2H), 6.29 (br d, J=8.5 Hz, 1H), 4.42 (br t, J=9.6 Hz, 1H), 3.74 (br d, J=10.1 Hz, 4H), 3.44-3.35 (m, 1H), 3.33-3.22 (m, 1H), 1.18-1.01 (m, 4H).

Example 69: $^1$H NMR (500 MHz, DMSO-d$_6$) δ 7.91 (br s, 1H), 6.89 (s, 1H), 6.70 (br d, J=11.0 Hz, 2H), 6.66 (br s, 1H), 6.32 (br d, J=8.2 Hz, 1H), 4.46 (br d, J=9.8 Hz, 1H), 3.86-3.65 (m, 4H), 3.45-3.36 (m, 1H), 3.31 (br d, J=9.5 Hz, 1H), 2.55 (s, 3H), 1.22 (s, 2H), 1.00 (br s, 2H).

Example 70: $^1$H NMR (500 MHz, DMSO-d$_6$) δ 7.91 (br s, 1H), 7.22 (s, 1H), 6.90 (s, 1H), 6.68 (br d, J=11.0 Hz, 2H), 6.40 (br d, J=8.2 Hz, 1H), 4.47 (br t, J=9.8 Hz, 1H), 3.83-3.66 (m, 4H), 3.41 (br t, J=9.2 Hz, 1H), 3.29 (br t, J=9.5 Hz, 1H), 2.22 (s, 3H), 1.47-1.30 (m, 2H), 1.16 (br s, 2H).

Example 71: $^1$H NMR (500 MHz, DMSO-d6) δ 7.91 (br s, 1H), 6.82-6.64 (m, 5H), 6.55 (br d, J=8.9 Hz, 1H), 6.27 (d, J=9.8 Hz, 1H), 6.20 (br d, J=8.2 Hz, 1H), 5.72 (d, J=9.8 Hz, 1H), 4.44 (br t, J=9.6 Hz, 1H), 3.75 (s, 3H), 3.63-3.48 (m, 1H), 3.45-3.35 (m, 1H), 3.29 (s, 1H), 1.33 (s, 6H), 1.01 (br s, 4H).

Example 72: $^1$H NMR (500 MHz, DMSO-d$_6$) δ 7.83 (s, 1H) 7.66 (d, J=8.75 Hz, 1H) 7.60 (s, 1H) 7.31 (br d, J=8.33

Hz, 1H) 7.09 (s, 1H) 6.65 (br d, J=10.69 Hz, 2H) 6.47-6.47 (m, 1H) 4.46 (br t, J=9.38 Hz, 1H) 3.73-3.81 (m, 1H) 3.73 (s, 3H) 3.41 (br t, J=9.17 Hz, 1H) 3.23-3.34 (m, 1H) 1.55 (br s, 2H) 1.21-1.28 (m, 2H).

Example 74: $^1$H NMR (500 MHz, DMSO-$d_6$) δ 7.82 (s, 1H), 7.23 (s, 1H), 7.14 (s, 1H), 7.00 (s, 1H), 6.93 (s, 1H), 6.66 (br d, J=10.6 Hz, 2H), 6.25 (d, J=8.3 Hz, 1H), 4.45 (dd, J=10.3, 8.7 Hz, 1H), 3.83-3.72 (m, 4H), 3.42 (s, 1H), 3.36-3.18 (m, 1H), 1.30-1.18 (m, 4H).

Example 75: $^1$H NMR (500 MHz, DMSO-$d_6$) δ 7.96-8.01 (m, 1H) 7.91-7.96 (m, 1H) 7.80 (br d, J=8.24 Hz, 1H) 7.68 (br d, J=8.24 Hz, 1H) 7.23 (s, 1H) 6.66 (br d, J=10.99 Hz, 2H) 6.49-6.61 (m, 1H) 4.47 (br t, J=9.31 Hz, 1H) 3.71 (s, 3H) 3.75 (br d, J=9.77 Hz, 1H) 3.33-3.51 (m, 1H) 3.26 (br t, J=9.46 Hz, 1H) 1.58 (brs, 2H) 1.24-1.36 (m, 2H).

Example 76: $^1$H NMR (500 MHz, DMSO-$d_6$) δ 7.94 (s, 1H) 7.43 (d, J=8.24 Hz, 1H) 7.32 (s, 1H) 7.15 (s, 1H) 7.12 (br d, J=8.24 Hz, 1H) 6.68 (br d, J=10.99 Hz, 2H) 6.48 (br d, J=8.24 Hz, 1H) 4.47 (br t, J=9.61 Hz, 1H) 3.72 (s, 3H) 3.66-3.81 (m, 1H) 3.39-3.49 (m, 1H) 3.26 (br t, J=9.46 Hz, 1H) 2.42 (s, 3H) 1.48 (br s, 2H) 1.13-1.28 (m, 2H).

Example 78: $^1$H NMR (500 MHz, DMSO-$d_6$) δ 7.94 (br s, 1H), 7.26-7.16 (m, 2H), 7.11 (br d, J=7.2 Hz, 1H), 6.99 (br d, J=7.4 Hz, 2H), 6.85 (br s, 1H), 6.72 (br d, J=11.0 Hz, 2H), 6.25 (br d, J=8.3 Hz, 1H), 4.44 (br t, J=9.6 Hz, 1H), 3.75 (s, 3H), 3.52-3.45 (m, 1H), 3.43-3.35 (m, 1H), 3.33-3.26 (m, 1H), 1.09 (br d, J=8.9 Hz, 4H).

Example 79: $^1$H NMR (500 MHz, DMSO-$d_6$) δ 8.40 (s, 1H), 7.93 (br s, 1H), 7.70 (br d, J=8.5 Hz, 1H), 7.20 (br d, J=7.9 Hz, 1H), 7.01 (s, 1H), 6.75 (br d, J=11.0 Hz, 2H), 6.37 (br d, J=8.5 Hz, 1H), 4.45 (br t, J=9.5 Hz, 1H), 3.76 (s, 4H), 3.49-3.35 (m, 1H), 3.35-3.25 (m, 1H), 1.44-1.29 (m, 2H), 1.08 (br s, 2H).

Example 80: $^1$H NMR (500 MHz, DMSO-$d_6$) δ ppm 7.91 (br s, 1H) 7.02-7.16 (m, 1H) 6.90 (br d, J=7.63 Hz, 1H) 6.85 (s, 1H) 6.80 (s, 1H) 6.78 (br d, J=7.93 Hz, 1H) 6.70 (br d, J=10.68 Hz, 2H) 6.19 (br d, J=8.54 Hz, 1H) 4.44 (br t, J=9.61 Hz, 1H) 3.71-3.83 (m, 1H) 3.36-3.48 (m, 1H) 3.27 (br t, J=9.46 Hz, 1H) 2.22 (s, 3H) 1.07 (br s, 4H).

Example 81: 1H NMR (500 MHz, DMSO-$d_6$) δ 7.99 (br s, 1H), 7.83-7.76 (m, 1H), 7.53 (s, 1H), 7.50-7.44 (m, 2H), 6.69 (br d, J=10.8 Hz, 2H), 6.62 (br d, J=5.9 Hz, 1H), 4.50 (br s, 1H), 3.93-3.77 (m, 1H), 3.72 (s, 3H), 3.45-3.37 (m, 1H), 3.35-3.15 (m, 1H), 1.70-1.56 (m, 2H), 1.35 (br s, 2H)

Example 82: 1H NMR (500 MHz, DMSO-$d_6$) δ 8.23 (br d, J=8.2 Hz, 1H), 8.16 (s, 1H), 8.00 (br s, 1H), 7.69 (br d, J=8.4 Hz, 1H), 7.51 (s, 1H), 6.75 (br d, J=10.9 Hz, 2H), 6.58 (br d, J=6.8 Hz, 1H), 4.55 (br t, J=8.8 Hz, 1H), 3.85-3.74 (m, 1H), 3.72 (s, 3H), 3.31 (br d, J=9.6 Hz, 1H), 3.18 (d, J=5.2 Hz, 1H), 1.75-1.54 (m, 2H), 1.36 (br s, 2H)

Example 83: $^1$H NMR (500 MHz, DMSO-$d_6$) δ ppm 8.02 (s, 1H) 7.72 (s, 1H) 7.60 (d, J=8.24 Hz, 1H) 7.34-7.41 (m, 1H) 7.29 (br d, J=8.54 Hz, 2H) 7.24 (s, 1H) 6.54 (br d, J=7.93 Hz, 1H) 4.48 (br t, J=9.31 Hz, 1H) 3.73-3.85 (m, 1H) 3.29 (br t, J=9.46 Hz, 1H) 1.52 (br s, 3H) 1.16-1.32 (m, 2H).

Example 85: $^1$H NMR (500 MHz, DMSO-$d_6$) δ 7.96 (br s, 1H), 7.73 (s, 1H), 7.67 (d, J=8.2 Hz, 1H), 7.38 (s, 1H), 7.24 (br d, J=8.2 Hz, 1H), 6.74 (br d, J=10.7 Hz, 2H), 6.49 (br d, J=7.6 Hz, 1H), 4.56 (br t, J=9.6 Hz, 1H), 3.82-3.66 (m, 4H), 3.62-3.40 (m, 1H), 3.36-3.12 (m, 1H), 2.43 (s, 3H), 1.74-1.41 (m, 2H), 1.29 (br s, 2H).

Example 86: $^1$H NMR (500 MHz, DMSO-$d_6$) δ 7.96 (br s, 1H), 7.76 (br t, J=4.4 Hz, 1H), 7.40 (s, 1H), 7.24 (d, J=4.9 Hz, 2H), 6.73 (br d, J=11.0 Hz, 2H), 6.53-6.45 (m, 1H), 4.55 (br t, J=9.6 Hz, 1H), 3.88-3.75 (m, 1H), 3.72 (s, 3H), 3.30 (br t, J=9.9 Hz, 1H), 3.21-3.12 (m, 1H), 2.54 (s, 3H), 1.77-1.46 (m, 2H), 1.30 (br s, 2H).

Example 87: $^1$H NMR (500 MHz, DMSO-$d_6$) δ ppm 7.94 (s, 1H) 7.59 (dd, J=8.70, 5.04 Hz, 1H) 7.49 (dd, J=8.39, 2.29 Hz, 1H) 7.15-7.22 (m, 2H) 6.68 (br d, J=10.99 Hz, 2H) 6.49 (br d, J=8.24 Hz, 1H) 4.46 (br t, J=9.61 Hz, 1H) 3.72 (s, 1H) 3.67-3.83 (m, 1H) 3.22-3.31 (m, 2H) 1.44-1.56 (m, 2H) 1.13-1.30 (m, 2H).

Example 88: $^1$H NMR (500 MHz, CD$_3$CN) δ ppm 7.52 (br d, J=8.53 Hz, 1H) 7.48-7.51 (m, 1H) 7.32 (dd, J=8.39, 1.79 Hz, 1H) 7.25 (br d, J=7.70 Hz, 1H) 6.48 (d, J=11.00 Hz, 1H) 6.29 (br s, 1H) 6.16 (br s, 1H) 5.67 (br d, J=5.23 Hz, 1H) 4.56 (t, J=8.67 Hz, 3H) 3.71 (br d, J=9.63 Hz, 1H) 3.52 (br t, J=8.94 Hz, 1H) 3.21 (br t, J=9.63 Hz, 1H) 2.95-3.15 (m, 2H) 1.51-1.70 (m, 2H) 1.36 (br s, 2H).

Example 89: $^1$H NMR (400 MHz, DMSO-$d_6$) δ 7.82 (s, 1H), 7.37-7.26 (m, 2H), 7.09 (d, J=7.6 Hz, 1H), 7.03 (s, 2H), 6.90 (s, 1H), 6.60 (d, J=11.2 Hz, 1H), 6.22 (d, J=8.6 Hz, 1H), 4.55 (t, J=8.7 Hz, 3H), 4.44-4.38 (m, 1H), 4.09 (d, J=4.9 Hz, 1H), 3.64 (d, J=8.3 Hz, 1H), 3.15-3.00 (m, 4H), 1.17 (d, J=4.6 Hz, 4H).

Example 90: $^1$H NMR (500 MHz, DMSO-$d_6$) δ ppm 7.92 (s, 1H) 7.18-7.28 (m, 1H) 7.07-7.18 (m, 2H) 6.86 (d, J=8.24 Hz, 1H) 6.65 (br d, J=10.99 Hz, 2H) 6.47 (br d, J=8.54 Hz, 1H) 4.44 (br t, J=9.46 Hz, 1H) 3.89 (s, 3H) 3.71 (s, 3H) 3.39 (br t, J=8.85 Hz, 1H) 3.21-3.31 (m, 1H) 3.08-3.20 (m, 1H) 1.48 (br s, 2H) 1.20 (br d, J=13.73 Hz, 2H).

Example 91: $^1$H NMR (400 MHz, DMSO-$d_6$) δ 7.95 (s, 1H), 7.79 (t, J=7.5 Hz, 1H), 7.65 (t, J=7.8 Hz, 2H), 7.56 (d, J=8.1 Hz, 1H), 7.20 (d, J=7.8 Hz, 2H), 7.02 (s, 1H), 6.40 (d, J=8.8 Hz, 1H), 4.58-4.44 (m, 1H), 3.85 (d, J=10.5 Hz, 1H), 3.54-3.47 (m, 1H), 3.29-3.25 (m, 1H), 1.36 (d, J=11.5 Hz, 2H), 1.09 (br. s., 2H).

Example 92: $^1$H NMR (500 MHz, DMSO-d6) δ ppm 8.13 (d, J=8.85 Hz, 1H) 7.88 (br d, J=8.24 Hz, 1H) 7.76-7.85 (m, 2H) 7.66 (br t, J=7.63 Hz, 1H) 7.42-7.53 (m, 2H) 7.31 (br d, J=7.32 Hz, 1H) 7.06 (s, 1H) 6.65 (br d, J=10.68 Hz, 1H) 6.36 (br d, J=8.85 Hz, 2H) 4.54 (br t, J=8.54 Hz, 2H) 4.43 (br t, J=10.07 Hz, 1H) 3.25 (dt, J=10.76, 5.46 Hz, 1H) 3.12-3.20 (m, 2H) 2.94-3.11 (m, 2H) 1.48-1.70 (m, 2H) 1.17 (brs, 2H).

Example 93: $^1$H NMR (400 MHz, DMSO-$d_6$) δ 7.82 (s, 1H), 7.45 (t, J=7.7 Hz, 1H), 7.34 (d, J=7.8 Hz, 1H), 7.06 (d, J=7.6 Hz, 1H), 6.95 (d, J=7.8 Hz, 1H), 6.85 (s, 1H), 6.64 (d, J=11.0 Hz, 1H), 6.24 (d, J=9.0 Hz, 1H), 4.56 (t, J=8.7 Hz, 3H), 4.47-4.33 (m, 1H), 3.65 (d, J=10.5 Hz, 1H), 3.17-3.02 (m, 4H), 2.35 (s, 3H), 1.47-1.27 (m, 2H), 1.09-0.95 (m, 2H).

Example 94. $^1$H NMR (500 MHz, DMSO-$d_6$) δ 7.30 (t, J=7.8 Hz, 1H), 6.84 (d, J=7.0 Hz, 1H), 6.77 (d, J=7.6 Hz, 1H), 6.72 (s, 1H), 6.56 (d, J=11.0 Hz, 2H), 6.21 (d, J=8.5 Hz, 1H), 4.34 (t, J=9.5 Hz, 1H), 3.64-3.50 (m, 4H), 3.40 (t, J=9.0 Hz, 1H), 3.36-3.19 (m, 1H), 3.07 (dd, J=13.9, 6.9 Hz, 1H), 2.83-2.73 (m, 1H), 2.16 (s, 3H), 1.27-1.05 (m, 2H), 0.90-0.78 (m, 2H), 0.76-0.66 (m, 1H), 0.33-0.22 (m, 2H), 0.02 (dd, J=11.3, 4.6 Hz, 2H).

Example 95. $^1$H NMR (500 MHz, DMSO-$d_6$) δ 8.16 (d, J=8.7 Hz, 1H), 7.89 (d, J=8.0 Hz, 1H), 7.81 (d, J=8.4 Hz, 1H), 7.67 (t, J=7.7 Hz, 1H), 7.52-7.40 (m, 2H), 7.01 (s, 1H), 6.71 (d, J=10.8 Hz, 2H), 6.41 (d, J=8.4 Hz, 1H), 4.53 (t, J=9.5 Hz, 1H), 3.88-3.67 (m, 4H), 3.55-3.46 (m, 1H), 3.47-3.31 (m, 2H), 3.14 (dt, J=13.4, 6.8 Hz, 1H), 1.66-1.54 (m, 2H), 1.56-1.48 (m, 2H), 1.21-1.12 (m, 2H), 0.86 (t, J=7.3 Hz, 3H).

Example 96. $^1$H NMR (500 MHz, DMSO-$d_6$) δ 8.26 (br d, J=8.2 Hz, 1H), 7.94 (br s, 1H), 7.79 (d, J=7.6 Hz, 1H), 7.56-7.46 (m, 2H), 6.71 (br d, J=11.0 Hz, 2H), 6.59 (br d, J=8.2 Hz, 1H), 4.54 (br t, J=10.1 Hz, 1H), 3.77-3.59 (m, 4H), 3.41 (br t, J=9.3 Hz, 1H), 3.34-3.24 (m, 1H), 1.66 (br d, J=9.5 Hz, 1H), 1.57 (br s, 1H), 1.36 (br s, 2H).

Example 97. ¹H NMR (500 MHz, DMSO-$d_6$) δ 7.32 (s, 1H), 7.13 (s, 1H), 7.03 (s, 2H), 6.71 (d, J=10.7 Hz, 2H), 6.51 (d, J=8.5 Hz, 1H), 4.52-4.34 (m, 3H), 3.94-3.80 (m, 1H), 3.76 (s, 3H), 3.66-3.55 (m, 1H), 3.47 (t, J=9.5 Hz, 1H), 1.27-1.07 (m, 4H).

Example 98. ¹H NMR (500 MHz, DMSO-$d_6$) δ 7.43 (d, J=8.5 Hz, 1H), 7.24 (d, J=1.5 Hz, 1H), 7.02 (s, 1H), 6.96 (br d, J=8.2 Hz, 1H), 6.73 (br d, J=11.0 Hz, 2H), 6.38 (br d, J=8.5 Hz, 1H), 4.49 (br t, J=9.5 Hz, 1H), 3.81-3.70 (m, 4H), 3.65 (dt, J=14.1, 7.1 Hz, 2H), 3.53 (br t, J=8.7 Hz, 1H), 3.46-3.33 (m, 1H), 2.93 (q, J=7.3 Hz, 1H), 2.61-2.56 (m, 1H), 1.21-1.07 (m, 4H).

Example 99. ¹H NMR (500 MHz, DMSO-$d_6$) δ 8.24 (br d, J=8.5 Hz, 1H), 7.93 (br s, 1H), 7.74 (br d, J=7.0 Hz, 1H), 7.57-7.42 (m, 3H), 7.14 (s, 1H), 6.73 (br d, J=11.0 Hz, 2H), 6.45 (br d, J=8.5 Hz, 1H), 4.47 (br t, J=9.6 Hz, 1H), 3.84-3.77 (m, 1H), 3.74 (s, 3H), 3.30 (br t, J=9.5 Hz, 1H), 3.17 (d, J=4.9 Hz, 1H), 1.66-1.51 (m, 2H), 1.17 (br s, 2H).

Example 100. ¹H NMR (500 MHz, DMSO-$d_6$) δ 7.98 (br s, 1H), 7.62 (d, J=8.2 Hz, 1H), 7.34 (br d, J=8.5 Hz, 2H), 7.03 (s, 1H), 7.00-6.94 (m, 1H), 6.41 (br d, J=8.5 Hz, 1H), 4.48 (br t, J=9.6 Hz, 1H), 3.70-3.58 (m, 1H), 3.51-3.40 (m, 1H), 3.34 (br t, J=9.5 Hz, 1H), 2.42 (s, 3H), 1.47-1.27 (m, 2H), 1.04 (br s, 2H).

Example 101. ¹H NMR (500 MHz, DMSO-$d_6$) δ 7.29 (s, 1H), 7.05 (d, J=1.6 Hz, 2H), 6.90 (s, 1H), 6.66 (d, J=10.7 Hz, 2H), 6.31 (d, J=8.3 Hz, 1H), 4.47 (t, J=9.2 Hz, 1H), 3.76 (s, 3H), 3.75-3.66 (m, 1H), 3.54-3.46 (m, 1H), 3.41-3.26 (m, 2H), 3.17-3.07 (m, 1H), 1.57-1.46 (m, 2H), 1.21-1.09 (m, 4H), 0.85 (t, J=7.3 Hz, 3H).

Example 102. ¹H NMR (500 MHz, DMSO-$d_6$) δ 7.63 (d, J=15.3 Hz, 1H), 7.13-7.05 (m, 2H), 6.97 (s, 1H), 6.71 (d, J=11.0 Hz, 2H), 6.37 (br d, J=8.9 Hz, 1H), 4.53 (t, J=9.6 Hz, 1H), 3.75 (s, 1H), 3.66 (s, 3H), 3.56 (s, 1H), 3.50-3.41 (m, 1H), 3.04-2.98 (m, 3H), 2.41 (s, 3H), 1.40 (br s, 2H), 1.27 (br d, J=5.2 Hz, 6H), 1.07 (br d, J=7.3 Hz, 2H).

Example 103. ¹H NMR (500 MHz, DMSO-$d_6$) δ 8.15 (d, J=8.8 Hz, 1H), 7.79 (s, 1H), 7.61 (d, J=8.1 Hz, 1H), 7.47 (d, J=8.7 Hz, 1H), 7.41 (t, J=7.9 Hz, 1H), 7.30 (d, J=7.6 Hz, 1H), 7.01 (s, 1H), 6.67 (br d, J=10.7 Hz, 2H), 6.34 (br d, J=8.4 Hz, 1H), 4.88 (q, J=8.9 Hz, 2H), 4.47 (br t, J=9.6 Hz, 1H), 3.84-3.75 (m, 1H), 3.74 (s, 3H), 3.45-3.40 (m, 1H), 3.31 (br t, J=9.6 Hz, 1H), 1.64-1.52 (m, 2H), 1.20-1.13 (m, 2H).

Example 104. ¹H NMR (500 MHz, DMSO-$d_6$) δ 8.19 (d, J=8.5 Hz, 1H), 7.91 (d, J=7.9 Hz, 1H), 7.82 (d, J=8.2 Hz, 1H), 7.69 (d, J=7.3 Hz, 1H), 7.55-7.42 (m, 2H), 7.34-7.26 (m, 1H), 6.79 (d, J=11.0 Hz, 2H), 6.70 (d, J=8.5 Hz, 1H), 4.61-4.47 (m, 1H), 4.28 (br dd, J=15.3, 10.1 Hz, 1H), 4.00 (br dd, J=15.7, 9.6 Hz, 1H), 3.77 (s, 4H), 3.67 (t, J=9.2 Hz, 1H), 3.61-3.49 (m, 1H), 1.68-1.51 (m, 2H), 1.27-1.12 (m, 2H).

Example 105. ¹H NMR (500 MHz, DMSO-$d_6$) δ 7.29 (s, 1H), 7.04 (s, 2H), 6.99 (s, 1H), 6.67 (d, J=10.4 Hz, 2H), 6.42 (d, J=8.3 Hz, 1H), 4.49 (t, J=9.4 Hz, 1H), 4.30-4.17 (m, 1H), 4.05-3.91 (m, 1H), 3.85 (br d, J=9.3 Hz, 1H), 3.76 (s, 3H), 3.69-3.60 (m, 1H), 3.59-3.53 (m, 1H), 1.27-1.07 (m, 4H).

Example 106. ¹H NMR (500 MHz, DMSO-$d_6$) δ 8.22 (d, J=8.9 Hz, 1H), 7.93 (d, J=7.9 Hz, 1H), 7.84 (d, J=8.5 Hz, 1H), 7.70 (t, J=7.3 Hz, 1H), 7.52 (t, J=7.3 Hz, 1H), 7.45 (d, J=8.9 Hz, 1H), 7.27 (d, J=5.8 Hz, 1H), 6.76 (d, J=10.7 Hz, 2H), 6.62 (d, J=8.5 Hz, 1H), 4.54-4.33 (m, 3H), 3.88 (s, 1H), 3.76 (s, 3H), 3.67-3.59 (m, 1H), 3.54-3.43 (m, 1H), 1.67-1.54 (m, J=17.7 Hz, 2H), 1.22-1.15 (m, 2H).

Example 107. ¹H NMR (500 MHz, DMSO-$d_6$) δ 7.30 (s, 1H), 7.07 (s, 2H), 7.06-7.00 (m, 2H), 6.68 (d, J=10.6 Hz, 2H), 6.45-6.38 (m, 1H), 4.52 (t, J=9.4 Hz, 1H), 3.77 (s, 3H), 3.71 (q, J=9.5 Hz, 1H), 3.62-3.47 (m, 4H), 3.43-3.35 (m, 1H), 3.28 (br s, 1H), 3.21-3.15 (m, 1H), 1.21-1.09 (m, 4H).

Example 108. ¹H NMR (500 MHz, DMSO-$d_6$) δ 7.63 (t, J=7.6 Hz, 1H), 7.16-7.04 (m, 3H), 6.99 (br s, 1H), 6.73 (d, J=11.0 Hz, 2H), 4.51 (t, J=9.0 Hz, 1H), 3.75 (s, 4H), 3.55-3.45 (m, 1H), 3.40 (t, J=9.3 Hz, 1H), 3.21-3.13 (m, 1H), 2.94 (br dd, J=13.3, 6.9 Hz, 1H), 2.41 (s, 3H), 1.90 (dt, J=13.7, 6.8 Hz, 1H), 1.47-1.33 (m, 2H), 1.12-1.02 (m, J=5.5 Hz, 2H), 0.84 (br dd, J=19.7, 6.6 Hz, 6H).

Example 110. ¹H NMR (500 MHz, DMSO-$d_6$) δ 7.62 (t, J=7.8 Hz, 1H), 7.14-7.04 (m, 3H), 6.74 (d, J=11.0 Hz, 2H), 6.57 (d, J=8.5 Hz, 1H), 4.51 (t, J=9.6 Hz, 1H), 4.25 (dd, J=14.8, 9.9 Hz, 1H), 3.97 (dd, J=15.3, 9.5 Hz, 1H), 3.89-3.81 (m, 1H), 3.75 (s, 1H), 3.64 (s, 3H), 3.54 (t, J=9.5 Hz, 1H), 2.40 (s, 3H), 1.48-1.34 (m, 2H), 1.13-1.01 (m, 2H).

Example 111. ¹H NMR (500 MHz, DMSO-$d_6$) δ 7.49 (t, J=7.8 Hz, 1H), 7.09-6.98 (m, 2H), 6.96 (d, J=7.3 Hz, 1H), 6.77 (d, J=10.7 Hz, 2H), 6.52 (d, J=8.2 Hz, 1H), 4.51-4.37 (m, 3H), 3.95-3.83 (m, 1H), 3.77 (s, 3H), 3.64-3.47 (m, 2H), 2.35 (s, 3H), 1.46-1.30 (m, 2H), 1.09-0.97 (m, 2H).

Example 112. ¹H NMR (500 MHz, DMSO-$d_6$) δ 8.10 (d, J=8.6 Hz, 1H), 7.82 (br s, 1H), 7.71 (br d, J=8.2 Hz, 1H), 7.52 (br d, J=6.7 Hz, 1H), 7.44 (br d, J=8.5 Hz, 1H), 7.37 (t, J=7.5 Hz, 1H), 7.01 (s, 1H), 6.70 (br d, J=10.7 Hz, 2H), 6.35 (br d, J=8.6 Hz, 1H), 4.49 (t, J=9.1 Hz, 1H), 3.81-3.73 (m, 4H), 3.45-3.39 (m, 1H), 2.60 (s, 3H), 1.67-1.54 (m, 2H), 1.22-1.12 (m, 2H). One proton on the lactam ring not observed due to water suppression.

Example 113. ¹H NMR (500 MHz, DMSO-$d_6$) δ 8.09 (br d, J=8.7 Hz, 1H), 7.81 (br s, 1H), 7.47 (br d, J=8.6 Hz, 1H), 7.44-7.35 (m, 2H), 7.12 (br d, J=7.2 Hz, 1H), 6.99 (s, 1H), 6.70 (br d, J=10.6 Hz, 2H), 6.35 (br d, J=8.2 Hz, 1H), 4.48 (br t, J=9.6 Hz, 1H), 3.93 (s, 3H), 3.84-3.77 (m, 1H), 3.76 (s, 3H), 3.44-3.36 (m, 1H), 3.31 (br s, 1H), 1.63-1.51 (m, 2H), 1.14 (br s, 2H)

Example 114. ¹H NMR (500 MHz, DMSO-$d_6$) δ 7.91 (br s, 1H), 7.08 (t, J=7.8 Hz, 1H), 6.83 (s, 1H), 6.74-6.64 (m, 3H), 6.62 (br s, 1H), 6.57 (br d, J=7.6 Hz, 1H), 6.19 (d, J=8.5 Hz, 1H), 4.43 (t, J=9.5 Hz, 1H), 3.75 (s, 3H), 3.68 (d, J=6.1 Hz, 2H), 3.27 (br t, J=9.5 Hz, 1H), 1.98 (tt, J=13.2, 6.6 Hz, 1H), 1.15-1.01 (m, 4H), 0.97 (d, J=6.4 Hz, 6H). Two protons on the lactam ring not observed due to water suppression.

Example 115. ¹H NMR (500 MHz, DMSO-$d_6$) δ 7.48 (t, J=7.6 Hz, 1H), 7.06-6.92 (m, 3H), 6.75 (d, J=11.0 Hz, 2H), 6.48 (d, J=8.5 Hz, 1H), 4.79 (d, J=16.2 Hz, 1H), 4.64 (d, J=16.5 Hz, 1H), 4.57 (t, J=9.6 Hz, 1H), 3.91-3.80 (m, 1H), 3.76 (s, 3H), 3.59 (t, J=9.2 Hz, 1H), 3.45-3.41 (m, 1H), 2.49 (s, 3H), 2.35 (s, 3H), 1.45-1.31 (m, 2H), 1.07-0.98 (m, 2H).

Example 116. ¹H NMR (500 MHz, DMSO-$d_6$) δ 7.55-7.45 (m, 1H), 7.04-6.92 (m, 3H), 6.74 (d, J=10.7 Hz, 2H), 6.42 (d, J=8.5 Hz, 1H), 4.60-4.43 (m, 1H), 3.76 (s, 3H), 3.69-3.57 (m, 1H), 3.56-3.46 (m, 3H), 3.45-3.33 (m, 1H), 2.95-2.86 (m, 1H), 2.61-2.56 (m, 1H), 2.36 (s, 3H), 1.38 (br d, J=8.5 Hz, 2H), 1.03 (br s, 2H).

Example 117. ¹H NMR (500 MHz, DMSO-$d_6$) δ 7.54 (t, J=7.7 Hz, 1H), 7.23 (s, 1H), 7.13 (s, 1H), 7.09 (d, J=7.9 Hz, 1H), 7.05-6.99 (m, 1H), 6.70 (d, J=10.7 Hz, 2H), 4.56 (t, J=9.2 Hz, 1H), 3.89 (s, 1H), 3.77 (s, 3H), 3.75-3.65 (m, 1H), 3.62-3.48 (m, 4H), 3.47-3.35 (m, 1H), 3.32-3.22 (m, 1H), 2.38 (s, 3H), 1.46-1.35 (m, 2H), 1.11-0.98 (m, 2H).

Example 118. ¹H NMR (500 MHz, DMSO-$d_6$) δ 7.47 (t, J=7.6 Hz, 1H), 7.04 (d, J=7.7 Hz, 1H), 6.94 (d, J=7.6 Hz, 1H), 6.80 (s, 1H), 6.70 (d, J=10.8 Hz, 2H), 6.30 (d, J=8.4 Hz, 1H), 4.56 (t, J=9.3 Hz, 1H), 3.81-3.70 (m, 4H), 3.68-3.60 (m, 2H), 3.06 (br s, 1H), 3.04-2.98 (m, 1H), 2.35 (s, 3H), 1.44-1.32 (m, 2H), 1.24 (br s, 1H), 1.13 (s, 3H), 1.09 (s, 3H), 1.06-0.95 (m, 2H).

Example 119. ¹H NMR (500 MHz, DMSO-d₆) δ 7.49 (t, J=7.6 Hz, 1H), 7.35 (d, J=8.5 Hz, 2H), 7.02 (s, 1H), 6.96 (d, J=7.6 Hz, 2H), 6.53 (d, J=8.2 Hz, 1H), 4.78 (br d, J=16.5 Hz, 1H), 4.68-4.53 (m, 2H), 3.69-3.60 (m, 2H), 3.60-3.48 (m, 1H), 2.98 (s, 3H), 2.34 (s, 3H), 1.36 (d, J=15.6 Hz, 2H), 1.08-0.90 (m, 2H).

Example 120. ¹H NMR (500 MHz, DMSO-d₆) δ 7.81 (s, 1H), 7.61 (d, J=7.7 Hz, 2H), 7.44 (t, J=7.5 Hz, 2H), 7.41-7.33 (m, 3H), 7.30 (t, J=7.7 Hz, 1H), 7.04 (d, J=7.7 Hz, 1H), 6.83 (s, 1H), 6.61 (d, J=10.6 Hz, 2H), 6.17 (d, J=8.2 Hz, 1H), 4.46 (t, J=9.4 Hz, 1H), 3.74 (s, 3H), 3.84-3.70 (m, 1H), 3.46-3.37 (m, 1H), 3.36-3.24 (m, 1H), 1.29-1.05 (m, 4H).

Example 121. ¹H NMR (500 MHz, DMSO-d₆) δ 7.90 (s, 1H), 7.66 (s, 1H), 7.62-7.55 (m, 1H), 7.52-7.44 (m, 1H), 7.41 (d, J=8.2 Hz, 2H), 7.36-7.27 (m, 2H), 7.06-7.00 (m, 1H), 7.00-6.87 (m, 1H), 6.60 (d, J=10.7 Hz, 1H), 6.28 (d, J=8.5 Hz, 1H), 4.43 (br t, J=9.6 Hz, 1H), 3.71 (s, 2H), 3.27 (br t, J=9.5 Hz, 1H), 1.21 (br s, 3H), 1.18-1.06 (m, 2H). Two protons on the lactam ring obscured due to water suppression.

Example 123. ¹H NMR (500 MHz, DMSO-d₆) δ 7.98 (br s, 1H), 7.39-7.20 (m, 3H), 7.09-6.93 (m, 3H), 6.36 (d, J=8.5 Hz, 1H), 4.46 (t, J=9.5 Hz, 1H), 3.87-3.76 (m, 1H), 3.31 (t, J=9.5 Hz, 1H), 1.19 (br s, 2H), 1.15-1.02 (m, 2H). one proton on the lactam ring obscured due to water suppression.

Example 125. ¹H NMR (500 MHz, DMSO-d₆) δ 7.91 (br s, 1H), 7.60 (d, J=7.6 Hz, 2H), 7.48-7.41 (m, 3H), 7.37-7.30 (m, 1H), 7.09-7.01 (m, 2H), 6.89 (s, 2H), 6.72 (d, J=11.0 Hz, 2H), 6.25 (d, J=8.5 Hz, 1H), 4.47 (t, J=9.9 Hz, 1H), 3.71 (s, 3H), 3.43-3.37 (m, 1H), 3.33-3.26 (m, 1H), 1.19-1.06 (m, 4H). One proton on the lactam ring obsured by water suppression.

Example 127. ¹H NMR (500 MHz, DMSO-d₆) δ ppm 8.14 (br d, J=8.85 Hz, 1H) 7.94 (br s, 1H) 7.90 (br d, J=8.24 Hz, 1H) 7.80 (br d, J=8.24 Hz, 1H) 7.67 (br t, J=7.63 Hz, 1H) 7.49 (br t, J=7.32 Hz, 1H) 7.38 (br d, J=7.63 Hz, 1H) 7.09 (s, 1H) 6.82 (br d, J=10.38 Hz, 2H) 6.43 (br d, J=8.54 Hz, 1H) 4.50 (br t, J=9.00 Hz, 1H) 3.78-3.89 (m, 1H) 3.31 (br t, J=9.31 Hz, 1H) 1.85-1.98 (m, 1H) 1.46-1.67 (m, 2H) 1.08-1.19 (m, 2H) 0.88-1.02 (m, 2H) 0.68 (br s, 2H). One proton on the lactam ring obscured by water suppression.

Example 128. ¹H NMR (500 MHz, DMSO-d₆) δ 7.77 (br s, 1H), 7.13-7.04 (m, 5H), 6.75 (s, 1H), 6.73-6.67 (m, 2H), 6.67-6.56 (m, 3H), 6.11 (d, J=8.3 Hz, 1H), 4.43 (t, J=9.3 Hz, 1H), 3.90 (br d, J=6.0 Hz, 2H), 3.73 (s, 3H), 3.81-3.70 (m, 1H), 2.96-2.87 (m, 1H), 2.85-2.75 (m, 2H), 2.62-2.56 (m, J=10.8 Hz, 1H), 2.23-2.12 (m, 1H), 2.07-1.95 (m, J=12.8 Hz, 1H), 1.57-1.42 (m, 1H), 1.15-1.00 (m, 4H). Two protons on the lactam ring obscured by water suppression.

Example 129. ¹H NMR (500 MHz, DMSO-d₆) δ 7.79 (br s, 1H), 7.27-7.15 (m, 3H), 7.14-7.05 (m, 2H), 6.78-6.68 (m, 3H), 6.64 (br d, J=10.4 Hz, 3H), 6.10 (br d, J=8.2 Hz, 1H), 4.44 (t, J=9.4 Hz, 1H), 4.25-4.11 (m, J=7.1 Hz, 3H), 3.94-3.82 (m, 1H), 3.75 (s, 3H), 3.79-3.71 (m, 1H), 3.40 (t, J=9.2 Hz, 1H), 3.38-3.31 (m, 1H), 2.95 (d, J=13.9 Hz, 1H), 1.15-1.01 (m, 4H). Two protons on the lactam ring obscured by water suppression.

Example 130. ¹H NMR (500 MHz, DMSO-d₆) δ 7.96-7.82 (m, 5H), 7.50 (br t, J=7.2 Hz, 4H), 6.85 (s, 1H), 6.80-6.73 (m, 1H), 6.71 (br d, J=11.0 Hz, 2H), 6.60 (br d, J=7.9 Hz, 1H), 6.32 (br d, J=8.2 Hz, 1H), 5.39 (s, 2H), 4.44 (t, J=9.2 Hz, 1H), 3.73 (s, 3H), 3.45-3.34 (m, 1H), 3.29 (t, J=9.5 Hz, 1H), 1.42-1.28 (m, 2H), 1.06-0.91 (m, 2H). One protos on the lactam ring obscured by water suppression.

Example 132. ¹H NMR (500 MHz, DMSO-d₆) δ ppm 7.92 (br s, 1H) 7.32-7.37 (m, 4H) 7.24-7.31 (m, 2H) 7.09 (t, J=7.93 Hz, 1H) 6.83 (s, 1H) 6.69 (br d, J=10.68 Hz, 3H) 6.56-6.65 (m, 2H) 6.19 (br d, J=8.54 Hz, 1H) 4.55 (s, 2H) 4.44 (br t, J=9.61 Hz, 1H) 4.05-4.12 (m, 2H) 3.74-3.78 (m, 2H) 3.73 (s, 3H) 3.23-3.31 (m, 1H) 1.00-1.16 (m, 4H). Two protons from the lactam ring obscured due to water suppression.

Example 133. ¹H NMR (500 MHz, DMSO-d₆) δ 7.90 (br s, 1H), 7.31-7.23 (m, 2H), 7.23-7.19 (m, 2H), 7.19-7.13 (m, 1H), 7.07 (t, J=7.9 Hz, 1H), 6.82 (s, 1H), 6.71-6.61 (m, 3H), 6.58 (br s, 1H), 6.56 (br d, J=7.9 Hz, 1H), 6.18 (br d, J=8.2 Hz, 1H), 4.42 (br t, J=9.5 Hz, 1H), 3.91 (br s, 2H), 3.73 (s, 3H), 3.29-3.23 (m, 1H), 2.63 (br s, 2H), 1.70 (br s, 4H), 1.15-0.99 (m, 4H). Two protons on the lactam ring obscured by water suppression.

Example 134. ¹H NMR (500 MHz, DMSO-d₆) δ 7.90 (br s, 1H), 7.48 (t, J=7.5 Hz, 1H), 7.38-7.21 (m, 5H), 6.87 (s, 1H), 6.81-6.73 (m, 1H), 6.71 (d, J=11.0 Hz, 2H), 6.51 (d, J=7.9 Hz, 1H), 6.31 (d, J=8.5 Hz, 1H), 4.49 (s, 2H), 4.47-4.37 (m, 1H), 4.28 (s, 2H), 3.73 (s, 2H), 3.72-3.67 (m, 1H), 3.60-3.51 (m, 3H), 3.41-3.35 (m, 1H), 3.34-3.24 (m, 1H), 1.45-1.28 (m, 2H), 1.09-0.94 (m, 2H).

Example 135. ¹H NMR (500 MHz, DMSO-d₆) δ 7.93 (br s, 1H), 7.76 (d, J=8.2 Hz, 1H), 7.49 (d, J=3.4 Hz, 1H), 7.32-7.18 (m, 5H), 7.10-6.97 (m, 1H), 6.94 (s, 1H), 6.73 (br d, J=10.7 Hz, 2H), 6.45-6.38 (m, 1H), 6.34 (br d, J=8.5 Hz, 1H), 5.32 (s, 2H), 4.48 (br t, J=9.8 Hz, 1H), 3.76 (s, 3H), 3.45-3.37 (m, 1H), 3.34-3.26 (m, 1H), 1.54-1.35 (m, 2H), 1.15-1.01 (m, 2H). One proton on the lactam ring obscured by water suppression.

Example 136. ¹H NMR (500 MHz, DMSO-d₆) δ 7.90 (br s, 1H), 7.07 (t, J=7.9 Hz, 1H), 6.83 (s, 1H), 6.72-6.62 (m, 3H), 6.59 (br s, 1H), 6.55 (d, J=7.3 Hz, 1H), 6.19 (br d, J=8.5 Hz, 1H), 4.42 (t, J=9.6 Hz, 1H), 3.74 (s, 2H), 3.70 (d, J=6.1 Hz, 2H), 3.26 (t, J=9.6 Hz, 1H), 1.78 (br d, J=12.2 Hz, 2H), 1.74-1.59 (m, 4H), 1.32-1.13 (m, 4H), 1.12-0.95 (m, 6H). Two protons on the lactam ring obscured by water suppression.

Example 137. ¹H NMR (500 MHz, DMSO-d₆) δ 7.78 (br s, 1H), 7.08 (t, J=7.9 Hz, 1H), 6.73 (s, 1H), 6.68-6.62 (m, J=11.5 Hz, 4H), 6.60 (br d, J=7.6 Hz, 1H), 6.09 (d, J=8.4 Hz, 1H), 4.44 (t, J=9.5 Hz, 1H), 3.92-3.85 (m, 2H), 3.76 (s, 2H), 3.80-3.69 (m, 1H), 3.41 (br d, J=9.4 Hz, 1H), 2.74-2.61 (m, 1H), 2.13-2.00 (m, J=9.0 Hz, 2H), 1.95-1.86 (m, 2H), 1.86-1.76 (m, 2H), 1.12-1.03 (m, 4H). Two protons on the lactam ring obscured by water suppression.

Example 138. ¹H NMR (500 MHz, DMSO-d₆) δ 7.93 (br s, 1H), 7.51 (t, J=7.8 Hz, 1H), 6.88 (s, 1H), 6.78 (br d, J=6.7 Hz, 1H), 6.73 (d, J=11.0 Hz, 2H), 6.53 (d, J=7.9 Hz, 1H), 6.31 (d, J=8.5 Hz, 1H), 4.46 (br t, J=9.6 Hz, 1H), 4.32-4.24 (m, 2H), 4.10 (q, J=9.3 Hz, 2H), 3.90-3.84 (m, 2H), 3.75 (s, 3H), 1.39 (br d, J=6.7 Hz, 2H), 1.02 (br s, 2H). Three protons on the lactam ring obscured by water suppression.

Example 139. ¹H NMR (500 MHz, DMSO-d₆) δ 7.79 (br s, 1H), 7.27-7.15 (m, 3H), 7.14-7.05 (m, 2H), 6.78-6.68 (m, 3H), 6.64 (br d, J=10.4 Hz, 3H), 6.10 (br d, J=8.2 Hz, 1H), 4.44 (t, J=9.4 Hz, 1H), 4.25-4.11 (m, J=7.1 Hz, 3H), 3.94-3.82 (m, 1H), 3.75 (s, 3H), 3.79-3.71 (m, 1H), 3.40 (t, J=9.2 Hz, 1H), 3.38-3.31 (m, 1H), 2.95 (d, J=13.9 Hz, 1H), 1.15-1.01 (m, 4H). Two protons on the lactam ring obscured by water suppression.

Example 140. ¹H NMR (500 MHz, DMSO-d₆) δ 7.99 (s, 1H), 7.96-7.86 (m, 1H), 7.58 (br d, J=8.2 Hz, 1H), 7.40 (br s, 1H), 7.31-7.20 (m, 3H), 7.18 (br d, J=7.0 Hz, 2H), 6.96 (s, 1H), 6.78 (br d, J=8.5 Hz, 1H), 6.66 (d, J=11.0 Hz, 2H), 6.27 (d, J=8.5 Hz, 1H), 5.64-5.48 (m, 2H), 4.45 (t, J=9.6 Hz, 1H), 3.72 (s, 3H), 3.68-3.63 (m, J=6.4 Hz, 1H), 3.50-3.35 (m, 1H), 3.34-3.24 (m, 1H), 1.25-1.08 (m, 4H).

Example 141. $^1$H NMR (500 MHz, DMSO-d$_6$) δ 7.91 (s, 1H), 7.36 (t, J=7.8 Hz, 2H), 7.19 (t, J=7.9 Hz, 1H), 7.14-7.06 (m, 1H), 6.95 (d, J=7.9 Hz, 2H), 6.87 (s, 1H), 6.80 (d, J=7.6 Hz, 1H), 6.75 (s, 1H), 6.72-6.61 (m, 3H), 6.22 (d, J=8.2 Hz, 1H), 4.42 (t, J=9.6 Hz, 1H), 3.73 (s, 3H), 3.28 (br t, J=9.8 Hz, 1H), 1.09 (br s, 4H). Two protons on the lactam ring obscured by water suppression.

Example 142. $^1$H NMR (500 MHz, DMSO-d$_6$) δ 8.33 (s, 1H), 8.35-8.27 (m, 1H), 7.88 (br s, 1H), 7.52 (d, J=8.9 Hz, 1H), 7.37-7.21 (m, 6H), 6.89 (s, 1H), 6.73 (br d, J=8.9 Hz, 1H), 6.70-6.59 (m, 2H), 6.19 (br d, J=8.5 Hz, 1H), 5.57 (s, 2H), 4.42 (br t, J=9.5 Hz, 1H), 3.68 (s, 3H), 3.47-3.33 (m, 1H), 3.32-3.22 (m, 1H), 1.17-1.01 (m, 4H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of formula I

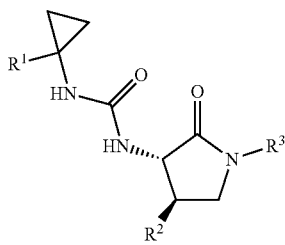

where:
R$^1$ is phenyl, biphenyl, dihydrobenzofuranyl, benzodioxolyl, chromenyl, naphthalenyl, pyrrolyl, furanyl, thienyl, pyrazolyl, isoxazolyl, isothiazolyl, imidazolyl, oxazolyl, thiazolyl, (phenyl)thiazolyl, triazolyl, oxadiazolyl, thiadiazolyl, pyridinyl, pyridazinyl, pyrimidinyl, pyrazinyl, indolyl, azaindolyl, benzofuranyl, benzothiophenyl, indazolyl, benzimidazolyl, benzoxazolyl, benzothiazolyl, pyrrolopyridinyl, furopyridinyl, thienopyridinyl, oxazolopyridinyl, thiazolopyridinyl, quinolinyl, isoquinolinyl, or naphthyridinyl, and is substituted with 0-3 substituents selected from cyano, halo, alkyl, benzyl, haloalkyl, alkoxy, haloalkoxy, phenylcyclohexyloxy, (trifluoroalkoxy)alkoxy, tetrahydronaphthylalkoxy, bicyclo[4.2.0]octa-1,3,5-trien-7-ylalkoxy, naphthylalkoxy, phenylalkoxy, biphenylalkoxy, (2,3-dihydro-1H-inden-2-yl)methoxy, (cycloalkyl)alkoxy, ((phenyl)alkoxy)alkoxy, and phenoxy;
R$^2$ is phenyl, pyridinyl, or dihydrobenzofuranyl, and is substituted with 0-3 substituents selected from cyano, halo, alkyl, haloalkyl, cycloalkyl, alkoxy, deuteroalkoxy, and haloalkoxy; and
R$^3$ is hydrogen, alkyl, hydroxyalkyl, alkoxyalkyl, haloalkyl, (cycloalkyl)alkyl, cyanoalkyl, arylalkyl or heteroarylalkyl;
or a pharmaceutically acceptable salt thereof.

2. A compound of claim 1 where:
R$^1$ is phenyl, dihydrobenzofuranyl, benzodioxolyl, chromenyl, naphthalenyl, pyrrolyl, furanyl, thienyl, pyrazolyl, isoxazolyl, isothiazolyl, imidazolyl, oxazolyl, thiazolyl, (phenyl)thiazolyl, triazolyl, oxadiazolyl, thiadiazolyl, pyridinyl, pyridazinyl, pyrimidinyl, pyrazinyl, indolyl, benzofuranyl, benzothiophenyl, indazolyl, benzimidazolyl, benzoxazolyl, benzothiazolyl, pyrrolopyridinyl, furopyridinyl, thienopyridinyl, oxazolopyridinyl, thiazolopyridinyl, quinolinyl, isoquinolinyl, or naphthyridinyl, and is substituted with 0-3 substituents selected from cyano, halo, alkyl, haloalkyl, alkoxy, haloalkoxy, and ((phenyl)alkoxy)alkoxy;
R$^2$ is phenyl, pyridinyl, or dihydrobenzofuranyl, and is substituted with 1-3 substituents selected from cyano, halo, alkyl, haloalkyl, alkoxy, and haloalkoxy; and
R$^3$ is hydrogen, alkyl, hydroxyalkyl, haloalkyl, cycloalkylalkyl, cyanoalkyl, arylalkyl or heteroarylalkyl;
or a pharmaceutically acceptable salt thereof.

3. A compound of claim 1 where:
R$^1$ is phenyl, benzodioxolyl, chromenyl, naphthalenyl, oxazolyl, thiazolyl, (phenyl)thiazolyl, pyridinyl, pyridazinyl, pyrimidinyl, pyrazinyl, benzothiophenyl, benzoxazolyl, benzothiazolyl, indazolyl, pyrrolopyridinyl, quinolinyl, isoquinolinyl, or naphthyridinyl, and is substituted with 0-3 substituents selected from cyano, halo, alkyl, haloalkyl, alkoxy, and haloalkoxy;
R$^2$ is phenyl, pyridinyl, or dihydrobenzofuranyl and is substituted with 1-3 substituents selected from halo and alkoxy; and
R$^3$ is hydrogen, alkyl, hydroxyalkyl, haloalkyl, cycloalkylalkyl, cyanoalkyl, arylalkyl or heteroarylalkyl;
or a pharmaceutically acceptable salt thereof.

4. A compound of claim 1 where R$^1$ is phenyl, dihydrobenzofuranyl, benzodioxolyl, chromenyl, naphthalenyl, oxazolyl, thiazolyl, (phenyl)thiazolyl, pyridinyl, pyridazinyl, pyrimidinyl, pyrazinyl, benzothiophenyl, indazolyl, benzoxazolyl, benzothiazolyl, pyrrolopyridinyl, quinolinyl, isoquinolinyl, or naphthyridinyl, and is substituted with 0-3 substituents selected from cyano, halo, alkyl, haloalkyl, alkoxy, and haloalkoxy;
R$^2$ is phenyl or dihydrobenzofuranyl, and is substituted with 1-3 substituents selected from cyano, halo, alkyl, haloalkyl, alkoxy, and haloalkoxy; and
R$^3$ is hydrogen, alkyl, hydroxyalkyl, haloalkyl, cycloalkylalkyl, cyanoalkyl, arylalkyl or heteroarylalkyl;
or a pharmaceutically acceptable salt thereof.

5. A compound of claim 1 where R$^1$ is phenyl, pyrrolyl, furanyl, thienyl, pyrazolyl, isoxazolyl, isothiazolyl, imidazolyl, oxazolyl, thiazolyl, (phenyl)thiazolyl, triazolyl, oxadiazolyl, thiadiazolyl, pyridinyl, pyridazinyl, pyrimidinyl, or pyrazinyl, and is substituted with 0-3 substituents selected from cyano, halo, alkyl, haloalkyl, alkoxy, and haloalkoxy.

6. A compound of claim 1 where R$^1$ is dihydrobenzofuranyl, benzodioxolyl, chromenyl, naphthalenyl, indolyl, benzofuranyl, benzothiophenyl, indazolyl, benzimidazolyl, benzoxazolyl, benzothiazolyl, pyrrolopyridinyl, furopyridinyl, thienopyridinyl, oxazolopyridinyl, thiazolopyridinyl, quinolinyl, isoquinolinyl, or naphthyridinyl, and is substituted with 0-3 substituents selected from cyano, halo, alkyl, haloalkyl, alkoxy, and haloalkoxy.

7. A compound of claim 1 R$^1$ is phenyl, dihydrobenzofuranyl, benzodioxolyl, chromenyl, naphthalenyl, oxazolyl, thiazolyl, (phenyl)thiazolyl, pyridinyl, pyridazinyl, pyrimidinyl, pyrazinyl, benzothiophenyl, indazolyl, benzoxazolyl, benzothiazolyl, pyrrolopyridinyl, quinolinyl, isoquinolinyl, or naphthyridinyl, and is substituted with 0-3 substituents selected from cyano, halo, alkyl, haloalkyl, alkoxy, and haloalkoxy.

8. A compound of claim 1 where $R^2$ is phenyl or dihydrobenzofuranyl, and is substituted with 1-3 substituents selected from cyano, halo, alkyl, haloalkyl, alkoxy, and haloalkoxy.

9. A compound of claim 1 where $R^3$ is hydrogen, alkyl, hydroxyalkyl, haloalkyl, cycloalkylalkyl, cyanoalkyl, arylalkyl or heteroarylalkyl.

10. A compound of claim 1 where $R^3$ is hydrogen, alkyl, or hydroxyalkyl.

11. A composition comprising a compound of claim 1, or a pharmaceutically acceptable salt thereof, and a pharmaceutically acceptable carrier, diluent, or excipient.

12. The method for treating post myocardial infarction comprising administering a therapeutically effective amount of a compound of claim 1 to a patient in need thereof.

* * * * *